US008722361B2

(12) United States Patent
Clark et al.

(10) Patent No.: US 8,722,361 B2
(45) Date of Patent: May 13, 2014

(54) PRODUCTION OF RECOMBINANT PROTEINS IN CILIATES AND USES THEREOF

(75) Inventors: Theodore G. Clark, Ithaca, NY (US); Ashot Papoyan, Lansing, NY (US); Aaron Turkewitz, Chicago, IL (US)

(73) Assignees: Tetragenetics, Inc., Cambridge, MA (US); The University of Chicago, Chicago, IL (US)

( * ) Notice: Subject to any disclaimer, the term of this patent is extended or adjusted under 35 U.S.C. 154(b) by 0 days.

(21) Appl. No.: 13/257,903

(22) PCT Filed: Mar. 22, 2010

(86) PCT No.: PCT/US2010/028165
§ 371 (c)(1),
(2), (4) Date: Jan. 9, 2012

(87) PCT Pub. No.: WO2010/108182
PCT Pub. Date: Sep. 23, 2010

(65) Prior Publication Data
US 2012/0107343 A1 May 3, 2012

Related U.S. Application Data

(60) Provisional application No. 61/162,059, filed on Mar. 20, 2009, provisional application No. 61/162,030, filed on Mar. 20, 2009, provisional application No. 61/255,186, filed on Oct. 27, 2009.

(51) Int. Cl.
*C07K 14/44* (2006.01)
(52) U.S. Cl.
CPC ..................................... *C07K 14/44* (2013.01)
USPC ...................................................... 435/69.1
(58) Field of Classification Search
CPC ........................... C07K 14/44; C07K 2319/01
USPC ....................................................... 435/69.1
See application file for complete search history.

(56) References Cited

U.S. PATENT DOCUMENTS

| | | | |
|---|---|---|---|
| 4,584,278 A * | 4/1986 | Knauf ............................ 436/542 |
| 2002/0002848 A1 | 1/2002 | Lin | |
| 2005/0106164 A1 | 5/2005 | Gaertig et al. | |

OTHER PUBLICATIONS

Somers et al. 2002; A panel of candidate tumor antigens in colorectal cancer revealed by the serological selection of phage displayed cDNA expression library. J. Immunol. 169(5): 2772-2780.*
Igietseme et al. 2006; Combination vaccines: design strategies and future trends. Expert Rev. Vaccines 5(6): 739-745.*
Arregui et al., "Cilliate contributions to bioaggregation: laboratory assays with axenis cultures of *Tetrahymena thermophila*," International Microbiology, vol. 10, pp. 91-96 (2007).
Becker et al., "The Secretory pathway of Protists: Spatial and functional Organization and evolution," Microbiological Reviews, vol. 60, pp. 697-721 (1996).
Bowman et al., "Genomic and proteomic evidence for a second family of dense core granule cargo proteins in *Tetrahymena thermophila*," J. Eukaryot Microbiol, vol. 52, pp. 291-297 (2005).
Chilcoat et al., "Granule lattice protein 1 (Grl1 p), an acidic calcium-binding protein in *Tetrahymena thermophila* dense-core secretory granules, influences granule size, shape, content organization, and release but not protein sorting or condensation," The Journal of Cell Biology, vol. 135, pp. 1775-1787 (1996).
Cowan et al, "Genetic, genomic and functional analysis of the granule lattice proteins in tetrahymena secretory granules," Molecular Biology, of the Cell, vol. 16, pp. 4046-4060 (2005).
Verbsky et al., "Proteolytic processing and Ca21-binding activity of dense-core vesicle polypetides in *Tetrahymena*," Molecular Biology of the Cell, vol. 9, pp. 497-511 (1998).
Weide et al., "Secretion of functional human enzymes by *Tetrahymena thermophila*," BMC Biotechnology, vol. 6, pp. 1-9 (2006).
International Search Report and Written Opinion mailed on Sep. 7, 2010 for International Application No. PCT/US10/28165 filed Mar. 22, 2010.
Bowman, Grant R. et al. "Core Formation and the Acquisition of Fusion Competence are Linked During Secretory Granule Maturation in *Tetrahymena*." Traffic. Blackwell Munksgaard. Jan. 10, 2005. vol. 6, No. 4, pp. 303-323.
Bradshaw, Niels R. et al. "Proprotein Processing within Secretory Dense Core Granules of *Tetrahymena thermophila*." The Journal of Biological Chemistry. JBC Papers in Press. Feb. 7, 2003. vol. 278, No. 6, pp. 4087-4095.
European Search Report for European Patent Application No. 10754235.9 mailed Dec. 12, 2012. 7 pages.
Gaertig, Jacek et al. "Surface Display of a Parasite Antigen in the Ciliate *Tetrahymena thermophila*." Natue Biotechnology. Nature Publishing Group, New York. May 17, 1999. vol. 17, No. 5, pp. 462-465.
Jayaram, Jyothi et al. "An Alternative Platform for Rapid Production of Effective Subunit Vaccines." International BioPharm: The Science& Business for Biopharmaceuticals. Supplement Oct. 2010. 8 pages.
Peterson, David S. et al. "The Circumsporozoite Protein of *Plasmodium falciparum* is Expressed and Localized to the Cell Surface in the Free-living Ciliate *Tetrahymena thermophila*." Molecular & Biochemical Parasitology. Elsevier Science B.V. Jul. 1, 2002.
Turkewitz, Aaron P. "Out with a Bang! *Tetrahymena* as a Model System to Study Secretory Granule Biogenesis." Traffic. Blackwell Munksgaard. Oct. 24, 2003. vol. 5, pp. 63-68.

* cited by examiner

*Primary Examiner* — Karen Cochrane Carlson
(74) *Attorney, Agent, or Firm* — Wilmer Cutler Pickering

(57) ABSTRACT

This invention is directed to methods for recombinant polypeptide production and, in particular, methods and products for the production and purification of recombinant proteins in ciliates.

21 Claims, 26 Drawing Sheets

Construct # 1

Construct #2

Construct # 3

A

H5ΔTMD^ProGrl1  [SP][H5][His]—TEV↓—[Pro-Grl1]

MGSKKIVLLFAIVSLVKSDQICIGYHANNSTEQVDTIMEKNVTVTHAQDILEKTHNGKLCDLD
GVKPLILRDCSVAGWLLGNPMCDEFINVPEWSYIVEKANPVNDLCYPGDFNDYEELKHLLSRIN
HFEKIQIIPKSSWSSHEASLGVSSACPYQGKSSFFRNVVWLIKKNSTYPTIKRSYNNTHQEDLLVL
WGIHHPNDAAEQTKLYQNPTTYISVGTSTLNQRLVPRIATRSKVNGQSGRMEFFWTILKPNDAI
NFESNGNFIAPEYAYKIVKKGDSTIMKSELEYGNCHTKCQTPMGAINSSMPFHNIHPLTIGECPK
YVKSHRLVLATGLRNSPQRERRRKKRGLFGAIAGFIEGGWQGMVDGWYGYHHSNEQGSGYA
ADKESTQKAIDGVTNKVNSIIDKMNTQFEAVGREFNNLERRIENLNKKMEDGFLDVWTYNAEL
LVLMENERTLDFHDSNVKNLYDKVRLQLRDNAKELGNGCFEFYHKCDNECMESVRNGTYDY
PQYSEEARLKREEIS*HHHHHHHHHH*ENLYFQG*FWQSRRRGSVTIDQAANLLNDLLADSQQNLS
DLQAAVANKEPLIQGVIAGLESDIANTQAECADIQGTLDADQASLDEAKAYVAWLQDETAAW
HKQIDNLLNERCQQFGNVIEGLENDKIAIAILQFLEAQRQHEESPSFLQKEIFNEELTEFISTY
FTGWYQQLALLRKEYVN*DDYSVNPDYSTGDRTADKIGSGHIDNDKGDIDVADFQEGERKG
VYQVKQELLDLLNNLEQTIEAKIQQAQDEVSNSAAADFKSKLEHKIQVYERELAKVQ
QTVAALTATVAQDHENVNNCHSQEAAIQANLDAANQDYANEKATFEHKQANLQKEIENFI
KVIAYYDDNVQNAGEDLKERVEDYSDGNFDDAATYERQVPNIDFIN

Bold Underlined: H5N1 HA Signal peptide
Black Text: H5N1 HA ΔTMD
*Underlined Bold Italicised text*: 10x His tag
Undelined Text: TEV Protease cleavage site
*Bold Italics Text: Grl1 Pro-domain*
Bold Text: Mature Grl1

H5ΔTMD[PrePro]

MGSMKKLLVVLFGFLALAAA *TWQSEKEGSYTIDQAAWILLNDLLADSQQW ISDLQAAVAWKEKPLLQGVIAGLESDLAWKQAECADLQGTLDADQASLDEA EAYVA VLQDRIAAWHKQIDDLLWPRCQQWGNYIEGLKWDKLALALLQFLE AQIQWKESFSFLQKKWFNKELTKFISVKTGNVQQLALLEKEYVKA*DQICIG YHANNSTEQVDTIMEKNVTVTHAQDILEKTHNGKLCDLDGVKPLILRDCS VAGWLLGNPMCDEFINVPEWSYIVEKANPVNDLCYPGDFNDYEELKHLIS RINHFEKIQIIPKSSWSSHEASLGVSSACPYQGKSSFFRNVVWLIKKNSTYPTI KRSYNNTNQEDLLVLWGIHHPNDAAEQTKLYQNPTTYISVGTSTLNQRLVP RIATRSKVNGQSGRMEFFWTILKPNDAINFESNGNFIAPEYAYKIVKKGDST IMKSELEYGNCNTKCQTPMGAINSSMPFHNIHPLTIGECPKYVKSNRLVLAT GLRNSPQRERRRKKRGLFGAIAGFIEGGWQGMVDGWYGYHHSNEQGSGY AADKESTQKAIDGVTNKVNSIIDKMNTQFEAVGREFNNLERRIENLNKKME DGFLDVWTYNAELLVLMENERTLDFHDSNVKNLYDKVRLQLRDNAKELG NGCFEFYHKCDNECMESVRNGTYDYPQYSEEARLKREEIS*HHHHHHHHHH*

Bold Underlined: Grf1 signal (pre) peptide

*Bold Italics Text: Grf1 Pro-domain*

Black Text: H5N1 HA ΔTMD

*Bold underlined italicised Text*: 10 x His tag

Figure 9A

B

Immunofluorescence showing mucocyst localization

C anti-HA Western (fractionated samples)

CL: Cell lysate
SN: Supernatant
M: Mucus

A

H5ΔTMD^(Igr1)  [Igr1] — TEV — [H5] [His]

**MGSRKIILLLAIISLALCQELIVEKVAGQY NSGQKFAKS V QNSQ V NDYQDFAIY
G V FKIDSSYQIAE VSTGFHFTSNQDKDVTNASAPGDRVLAF VVIGNTLHNPTY
SLARGNTNYYENLSFAAGDTNK N AFIYVTHGSSQQAQYVVYLLPSSGVVTKKI
ASITHKTSTFYQINVGQSFSFKYFPGSF VRLSLIAGPNAYRESGFEQFQNIQPDV
VPSCPILFTGCNYSGKGDSLCQSSPSYNVTA VNSIYLPANFTATLHDQANYAGK
KIVYSQSIECITQLN** VAYLISTHAITIEDETKT VLRRN N RRN EMLYFQGDQICIGY
HAH NSTEQ VDTI NEKN VTVTHAQDILERTH NGKLCDLDG VKPLILRDCS VAG V LL
GNP NC DEFINVPE VSYIVEKA NPV N DLCYPGDF ND YEELK HLLSRINHFEKIQIIPKS
S NSSHEASLGVSSACPYQG KSSFFRNVV N LIKK NST YPTIKRSYN N THQEDLLVL N
GIH HPND AAEQ TKLYQHPTT YISVGTSTLNQRL VPRIATKSK VNGQSGR KEFF NTIL
KPND AINHFESNGNFIAPEYA Y KIVKKGDSTI NKSELEYG NCN TKCQTP NGAINSSNP
FHNIHPLTIGNCPKYV KSNRLVLATGLRNSPQRERNRK KRGLFGAIAGFIEGG N QG N
VDG NYGY HESNHEQGSGY AAD KESTQKAIDGVTHK V NSIIDKNNTQFEA VGREFN
NLERRIENLNKK NEDGFLDV NTYN AELLVLNE NERTLDFN DSN VKNLYDKVRLQ
LRDN AKELGN GCFEFYHKCDNECNESVRN GTYDYPQ YSEEARLKREES *HHHH*
*HHH*

Bold Underlined: Igr1 Signal peptide

Bold Text: Mature Igr1

Underlined Text: TEV Protease cleavage site

Black Text: H5N1 HA ΔTMD

Italicized Text: 10 x His tag

Immunofluorescence showing
mucocyst localization

C     anti-HA Western (fractionated samples)

CL: Cell lysate
SN: Supernatant
M: Mucus

A

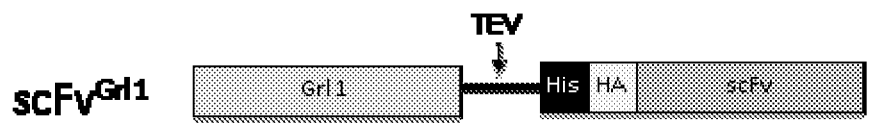

MGSIKLLVVLFGFLALAAA TWQSKEEGSVTIDQAAELLEDLLADSQQ
ELSDLQAAVAEEEPLLQGVLAGLESELAEEQAECADLQGTLDADQAS
LEEAEAVYAVLQDELAAEEEQIDDLLEERCQQWGEVLEGLEEDELAL
ALLQFLEAQIQEEESPSFLQEEVFEEELTEELSIVETGEVQQLALLEEE
VVEEDDYSVEPDYSTGDETADEIGSHIDEDEGDIDVADFQEGEEK
GVVQVKQELLDLLEELEQTIEAEIQQAQEDEVESESAAADFESKL
EEEIQVVEEELAKWQQTVAALTATVAQDEEEVEECESQEAAIQA
ELDAAEQDYAEEEATFEEEQAELQEEIEIEIEVIAYYDDEVQEAGE
DLEEEVEDYSDGEFDDAATYEEEQVPEEDFIEEELYFQGHHHHH
C VPYDVPDYELDIQMTQSPSSISASVGDRVTITCRASQDIEHYLH WYQ
QKPGKAPKLLIVYTSRLLPGVPSEFSGSGSGTDYTLTISSQEQEDIATYY
CQQGETLPVTFGQGTKVEIKRTGGGGSGGGGSGGGGSGGGSEVQL
VESGGGLVQPGGSLRLSCADSGVAFSSSEEEVVRQAPGKGLEVVGR
IVPGDGDTEVEGEFEGRATISADESSSTAVLQMESLRAEDTAVYCA
RSGLLRYAEDYVGQGTLVTVSS

Bold Underlined: Grl1 Signal (pre) peptide
Bold Italics Text: Grl1 Pro-domain
Bold Text: Mature Grl1
Underlined Text: TEV Protease cleavage site
Bold, Italicized underlined Text: 6 x His tag
Black Text: scFv

Immunofluorescence showing
mucocyst localization

C anti-HA Western (fractionated samples)

CL: Cell lysate
SN: Supernatant
M: Mucus

A pfs48/45^Grl4  

MGSRYAALFLLALISFHAVYA *VSLRESSDAMFTSFALEHLRFTGLESPT
AFQLTSAVELHLTTCGLVDDVIDL VFQAQEDVAHRWVALQAEYTAFRGA
LEDQIHTTTQQLHEEHDRLA VVHDAIDALHGQIDSLHTQLAHL VQQLQH
LQAEEDAIHQAEEVDVETYEVHFQRDEHVSLAVLEQHQHLLALQQFGHA
FLQVSHEEHHLHHFESHFTQALVQLSTH*DEQRLAEVISHLQTIQAAI
QASVIEDAHGEVADKQRYDALIQHIATIHAQTQQQLADAQQALSDA
EASLAQFVQEQGHLQQQIAVHEGILADAQAALAHTIATVEAHIQEG
QEALAAIHLALDVLQQHQSDLQGVEDFSHAYHAYQAGHSTDAGDD
AGDDSGVEGEAFDHTEKVISSHEGRSAHVHVRVLKYPHHILFTHLTHD
LFTYLPKTYHESHFVSHVLEVELHDGELFVLACHLIHKKCFQEGKEKAL
YKSHKIIYHKHLTIFKAPFVVTSKDVHTECTCKFKHHHYKIVLKPKYEK
KVIHGCHFSSHVSSKHTFTDSLDISLVDDSAHISCHVHLSEFKYHHLVGL
HCPGDIIPDCFFQVYQPESEELEPSHIVVLDSQIHIGDIEYVEDAEGDDKI
KLFGIVGSIPKTTSFTCICKKDKISAYHTVTID<u>HHHHHH</u>*CFAGTVVDDGT
STHFVALASECTRCQAHFVASRTSGFAAGTDTCTBCSKRLTSGATAHVYAEAT
QRAQCAS<u>YFYDFFDYA</u>*

<u>Bold Underlined: GrH Signal (pre) peptide</u>

*Bold Italics Text: GrH Pro-domain*

Bold Text: Mature GrH

Plain Text: pfs48/45

<u>Underlined Text</u>: 6 x His tag

*Italicized Text: I-Antigen C-terminal domain*

<u>*Bold, Italicked underlined Text: HA-tag*</u>

Immunofluorescence showing mucocyst localization

C

A pfs48/45^PrePro 

MGSIKILLVVLFGFLALAAATIQSEEEGSYTIDQAAILLIDILA
DSQQILSDLQAAVAIKEPLLQGVIAGLESDLAIKQAECADLQG
TLDADQASLDEAKAYVAVIQDEIAAIKQIDDLLIRRCQQIGI
YIEGLKIDELALALLQFLEAQIQIEESFSFLQKIIFIKKLTRFL
SIYKTGIYQQLALLEKEYVIADITEKVISSIEGRSAIVHVRVLKY
PHHILFTHLTHDLFTYLPKTYHESHFVSHVLEVELHDGELFVLACELI
HKKCFQEGKEKALYKSHKIIYHKILTIFKAPFYVTSKDVITECTCKF
KHHIYKIVLKPKYEKKVIHGCHFSSHVSSKHTFTDSLDISLVDDSAH
ESCHVHISEPKYHHLVGLHCPGDIIPDCFFQVYQPESHELEPSHIVYL
DSQIHIGDIEYYEDAEGDDKIKLFGIVGSIPKTTSFTCICKKDKKSAY
KTVTIDHHHHHH *CPAGTFPDDGTSTHFVALASECTRCQAIFYASRTSG
FAAGTDTCTECSRKLTSGATAKFYAEATQKAQCAS*___*YFYDFPDYA*

Underlined: Sril Signal (pre) peptide

Bold Text: Sri4 Pro-domain

Plain Text: pfs48/45

Underlined Text: 6 x His tag

*Italicized Text: I-Antigen C-terminal domain*

___*Bold, Italicized underlined Text: HA-tag*

PRODUCTION OF RECOMBINANT PROTEINS IN CILIATES AND USES THEREOF

This application is a U.S. National Phase application under 35 U.S.C. §371 of International Patent Application No. PCT/US2010/28165 filed Mar. 22, 2010, which claims priority to provisional U.S. Application Ser. No. 61/162,059, filed on Mar. 20, 2009, provisional U.S. Application Ser. No. 61/162,030, filed on Mar. 20, 2009 and provisional U.S. Application Ser. No. 61/255,186, filed on Oct. 27, 2009, which are each herein incorporated by reference in their entirety.

FIELD OF THE INVENTION

The invention relates to recombinant protein production and, in particular, methods and products for the production and purification of recombinant proteins in ciliates.

BACKGROUND OF THE INVENTION

Recombinant proteins are useful for a wide range of applications including, but not limited to, chemical and biological defense and the treatment and prevention of disease. Production of genetically engineered vaccine antigens, therapeutic proteins (including antibodies and antibody fragments), industrial enzymes, biopolymers, and bioremediation agents now constitute a multibillion dollar-per-year industry. There is also a large market for recombinant proteins in basic research (Pavlou and Reichert (2004); Langer (2005)).

Current platforms for the production of recombinant proteins are limited to a relatively small number of cell-based systems that include bacteria, fungi, and insect and mammalian tissue culture cells. Although bacteria can offer high yield and low cost alternatives for production of mammalian proteins, cell culture systems based on higher organisms (e.g., insect cells or mammalian cell systems) generally provide proteins having greater fidelity to the natural proteins in terms of protein folding and/or post-translational processing (e.g., glycosylation). Whole transgenic plants and animals have also been harnessed for the production of recombinant proteins, but the long development time from gene to final product can be a major drawback with these multicellular organisms, and purification of the recombinant proteins can be difficult and yield may be low.

Unicellular eukaryotes (e.g., *Saccharomyces cerevisiae* and *Pichia pastoris*) grow rapidly in inexpensive media and share some common pathways of protein folding, post-translational modification and protein targeting with more advanced organisms such as mammalian cells. Although the use of such unicellular eukaryotes for heterologous protein expression systems is known in the art, their rigid cell walls are an impediment to downstream protein purification.

After production of a desired recombinant protein within cells, the first step in isolating the protein is typically lysis of the cells. Lysis causes a forced mixing with the myriad of other cellular components, including proteases, which greatly complicates purification. In addition, lysis is problematic in expression systems that use microbial cells having rigid cell walls because the cell walls can impede downstream purification.

Although there are known methods, such as conventional chromatographic techniques (e.g., ion-exchange and affinity chromatography), for separating a desired protein from a mixture of proteins and/or cellular debris, such techniques can be inefficient and can require successive rounds of isolation over expensive column matrices to obtain highly purified products. These drawbacks add to manufacturing costs. Purification of recombinant proteins is a key factor in production costs, and even the most efficient systems consume between 25% and 80% of capital costs in the purification process (Frankel (2000)).

Most eukaryotic cells are capable of constitutive secretion. This is a process whereby proteins are delivered to the extracellular space via cargo vesicles that traffic to the cell surface by way of the endoplasmic reticulum (ER) and Golgi (Burgess and Kelly (1987)). This pathway has been harnessed for the production of recombinant gene products in a variety of systems and has significant advantages for protein purification because the process of secretion separates proteins of interest from the bulk of contaminating cellular material and obviates the need for cell lysis. Nonetheless, constitutive secretion has drawbacks as well. Typically, the process is slow and requires days to weeks to generate sufficient yields of a recombinant polypeptide for commercial use. In addition, thermal denaturation and the presence of proteolytic enzymes released into the culture medium can adversely affect the uniformity and function of the final protein product.

While most cells (including eukaryotic microbes) secrete proteins constitutively, there are some specialized cells that also store proteins in cortical secretory organelles (granules), which they discharge in a stimulus-dependent or regulated fashion (Burgess and Kelly (1987); Miller and Moore (1990); Gundelfinger et al. (2003)). In contrast with constitutive secretion, regulated secretion is triggered by the presence of chemical mediators known as secretagogues. Such mediators cause increased levels of intracellular calcium ($Ca^{++}$) which, in turn, trigger fusion of cortical granules with the plasma membrane and release of the granules contents into the surrounding extracellular space. Depending on the level of the stimulus, regulated secretion can be an all or none phenomenon. In some cases, relatively large amounts of protein can be released within a period on the order of milliseconds. The principal advantage of regulated secretion is that recombinant proteins can be harvested rapidly, thus speeding the manufacturing process, and improving the quality of the final product, particularly when long incubation times have deleterious effects on protein function.

Stimulus-dependent secretion has been intensively studied in specialized mammalian cells such as neurons, β-cells of the pancreas, and mast cells, and methods for the production of recombinant proteins that rely on regulated secretion have been described in the prior art (e.g., U.S. Pat. Nos. 6,087,129; 6,110,707; 6,194,176; Grampp et al. (1992); Chen et al. (1995); Yang and Hsieh (2001)). These methods are drawn to the use of mammalian cells, and require that the gene for a protein that normally occupies the secretory granules (for example, insulin) be deleted and replaced by a gene for the recombinant protein (for example, prolactin) engineered to traffic to the same organelles. In all cases, the released proteins must be purified from culture supernatants using conventional chromatographic techniques following the addition of secretagogues to the growth media.

The use of mammal cells for the preparation of recombinant polypeptides can be further complicated by high costs and safety issues arising from the risks of mycoplasma or viral infections of the cell lines.

Therefore, there remains a need in the art for improved methods for rapid, high-fidelity and cost-effective production and purification of recombinant polypeptides.

SUMMARY OF THE INVENTION

In one aspect, the invention provides methods for producing a desired heterologous polypeptide in a culture of ciliates, by (a) expressing a fusion protein comprising the heterologous polypeptide and a polypeptide comprising at least one mucocyst-targeting polypeptide in the ciliates; (b) stimulating regulated secretion from mucocysts of the ciliates, whereby an extracellular matrix is formed by the secretion; (c) separating the extracellular matrix from the ciliates; and (d) isolating the fusion protein from the extracellular matrix (e.g. a recombinant soluble protein) in a ciliate by targeting the heterologous polypeptide to mucocysts as a fusion protein with a mucocyst-targeting sequence or endogenous soluble mucocyst-targeted protein, stimulating regulated secretion from the mucocysts, and purifying the heterologous fusion protein from the resulting extra-cellular matrix produced by the mucocyst discharge. In each embodiment, the fusion protein comprises a polypeptide which targets the fusion protein to the mucocysts, and which includes a sequence which is cleaved by a protease endogenous to the mucocysts. As a result, all or some of the mucocyst-targeting sequences are removed from the heterologous polypeptide in vivo, enhancing its solubility, and facilitating its separation from the extracellular matrix produced by discharge of the mucocysts.

In another aspect, the invention provides isolated nucleic acids having a sequence encoding a fusion protein comprising: (a) at least one mucocyst-targeting polypeptide; (b) a heterologous polypeptide; and (c) a cleavable linker between the mucocyst-targeting polypeptide and the heterologous polypeptide.

In another aspect, the invention provides transgenic ciliates comprising: a nucleic acid having a sequence encoding: (a) at least one mucocyst-targeting polypeptide; (b)
a heterologous polypeptide; and (c) a cleavable linker between the mucocyst-targeting polypeptide and the heterologous polypeptide.

In another aspect, the invention provides protein preparations comprising:
(a) an extracellular matrix formed by regulated secretion by ciliates; and (b) a fusion protein encoded by the ciliates.

In another aspect, the invention provides vaccine preparations comprising:
(a) an extracellular matrix formed by regulated secretion by ciliates; and (b) a fusion protein encoded by the ciliates; wherein the fusion protein comprises an immunogenic polypeptide.

In another aspect, the invention provides vaccine preparations comprising:
(a) an extracellular matrix formed by regulated secretion by ciliates; and (b) at least two fusion proteins encoded by the ciliates; wherein the fusion proteins comprise different immunogenic polypeptides derived from the same pathogen or tumor cell.

In another aspect, the invention provides vaccine preparations comprising:
(a) an extracellular matrix formed by regulated secretion by ciliates; and (b) at least two fusion proteins encoded by the ciliates; wherein the fusion proteins comprise different immunogenic polypeptides derived from different pathogens and/or tumor cells.

In another aspect, the invention provides vaccine preparations comprising:
(a) an extracellular matrix formed by regulated secretion by ciliates; and (b) at least two different fusion proteins encoded by the ciliates; wherein one of the fusion proteins comprises an immunogenic polypeptide derived from a pathogen and/or tumor cell; and one of the fusion proteins comprises an immunostimulatory polypeptide or a receptor that binds an immunostimulatory polypeptide, designed to enhance the B- and/or T-cell response to the co-expressed immunogenic polypeptide(s).

Thus, in one aspect, the present invention provides methods for the production of a heterologous soluble polypeptide by a ciliate by (a) transforming the ciliate with a nucleic acid encoding a fusion protein including (i) a mucocyst-targeting polypeptide of a mucocyst-targeted protein which is cleaved by a protease endogenous to the mucocyst, and (ii) a heterologous polypeptide, such that expression of the fusion protein results in trafficking of the fusion protein to mucocysts within the ciliate and cleavage of the mucocyst-targeting polypeptide to release the heterologous soluble polypeptide within the mucocysts, (b) stimulating regulated secretion from the mucocysts of the ciliate, such that an extracellular matrix is formed, and (c) separating the heterologous soluble polypeptide from the extracellular matrix and the ciliates.

In some embodiments of this aspect, the mucocyst-targeted protein is a Grl protein, including a Grl-1 protein, such as a Grl-2 protein a Grl-3 protein, a Grl-4 protein, a Grl-5 protein, a Grl-6 protein, a Grl-7 protein, a Grl-8 protein, a Grl-9 protein or a Grl-10 protein, and in some embodiments the mucocyst-targeting domain comprises a pro-domain of a Grl protein. In other embodiments, the mucocyst-targeted protein is a β/γ crystalline domain containing protein.

In some embodiments of this aspect, the fusion protein also includes an endoplasmic reticulum-targeting polypeptide N-terminal to the mucocyst-targeting polypeptide. In some of these embodiments, the endoplasmic reticulum-targeting polypeptide is a pre-domain of a Grl protein, in some it is heterologous to said mucocyst-targeting polypeptide, and in some it is derived from an exogenous protein.

In another aspect, the invention provides methods for the production of a heterologous soluble polypeptide by a ciliate, by (a) transforming the ciliate with a nucleic acid encoding a first fusion protein including (i) a heterologous polypeptide, and (ii) at least a mucocyst-targeting polypeptide of a mucocyst-targeted protein, such that expression of the first fusion protein results in trafficking of the first fusion protein to mucocysts within the ciliate, and such that an endogenous protease within the mucocysts cleaves a cleavage site within the mucocyst-targeting polypeptide and removes any sequences C-terminal to the cleavage site, thereby producing a second fusion protein within the mucocysts, (b) stimulating regulated secretion from the mucocysts of the ciliate, such that an extracellular matrix is formed, and (c) separating the heterologous polypeptide from the extracellular matrix and the ciliates.

In some embodiments of this aspect, the mucocyst-targeted protein is a Grl protein, including a Grl-1 protein, such as a Grl-2 protein a Grl-3 protein, a Grl-4 protein, a Grl-5 protein, a Grl-6 protein, a Grl-7 protein, a Grl-8 protein, a Grl-9 protein or a Grl-10 protein, and in some embodiments the mucocyst-targeting domain comprises a pro-domain of a Grl protein. In other embodiments, the mucocyst-targeted protein is a β/γ crystalline domain containing protein.

In some embodiments of this aspect, the fusion protein also includes an endoplasmic reticulum-targeting polypeptide N-terminal to the mucocyst-targeting polypeptide. In some of these embodiments, the endoplasmic reticulum-targeting polypeptide is a pre-domain of a Grl protein, in some it is heterologous to said mucocyst-targeting polypeptide, and in some it is derived from an exogenous protein.

In some embodiments of this aspect, the fusion protein also includes a second protease cleavage site between the heterologous polypeptide and the mucocyst-targeting polypeptide. In these embodiments, the method can also include the additional step of reacting said second fusion protein with a second protease which cleaves said second protease cleavage site after either step (b) or step (c).

In another aspect, the invention provides methods for the production of a heterologous soluble polypeptide by a ciliate by (a) transforming the ciliate with a nucleic acid encoding a fusion protein including (i) a soluble polypeptide endogenous to the mucocyst, (ii) a protease cleavage site, and (iii) a heterologous polypeptide, such that expression of the fusion protein results in trafficking of the fusion protein to mucocysts within the ciliate, (b) stimulating regulated secretion from the mucocysts of the ciliate, such that an extracellular matrix is formed by the secretion, (c) separating the fusion protein from the extracellular matrix and the ciliates, and (d) obtaining the heterologous soluble polypeptide from the fusion protein.

In some embodiments of this aspect, the mucocyst-targeted protein is an Igr protein. In some embodiments, the mucocyst-targeted protein is a granule tip protein. In other embodiments, the mucocyst-targeted protein is a β/γ crystalline domain containing protein. In other embodiments, the mucocyst-targeted protein is a C-terminal crystallin fold containing protein.

In some embodiments of this aspect, step (d) of the methods include reacting the heterologous soluble polypeptide with a protease which cleaves the protease cleavage site.

In some embodiments of this aspect, the fusion protein further comprises an endoplasmic reticulum-targeting polypeptide N-terminal to the heterologous polypeptide. In some of these embodiments, expression of the fusion protein results in trafficking of the fusion protein to mucocysts within the ciliate and cleavage of the endoplasmic reticulum-targeting polypeptide. In some of these embodiments, the endoplasmic reticulum-targeting polypeptide is a pre-domain of a Grl protein, in some embodiments it is heterologous to the endogenous soluble polypeptide, and in some embodiments it is exogenous to the ciliate.

In another aspect, the invention provides nucleic acids having a sequence encoding any of the fusion proteins described above. These nucleic acids can be isolated linear DNA molecules or can be integrated into various vectors for molecular cloning or transformation. The nucleic acids can also include regulatory regions such as promoters, terminators and enhancers to which the coding sequences are operably joined, as well as reporter an/or selectable marker genes.

In another aspect, the invention provides transgenic ciliates transformed with any of the nucleic acids of the invention.

In another aspect, the invention provides protein preparations produced by any of the methods of the invention. These protein preparations include crude preparations resulting from regulated secretion by the ciliates of the invention with minimal purification, as well as substantially pure preparations of the desired soluble heterologous polypeptides.

These and other aspects of the invention will be apparent to those of ordinary skill in the art in view of the following detailed description and examples.

Figure 6:
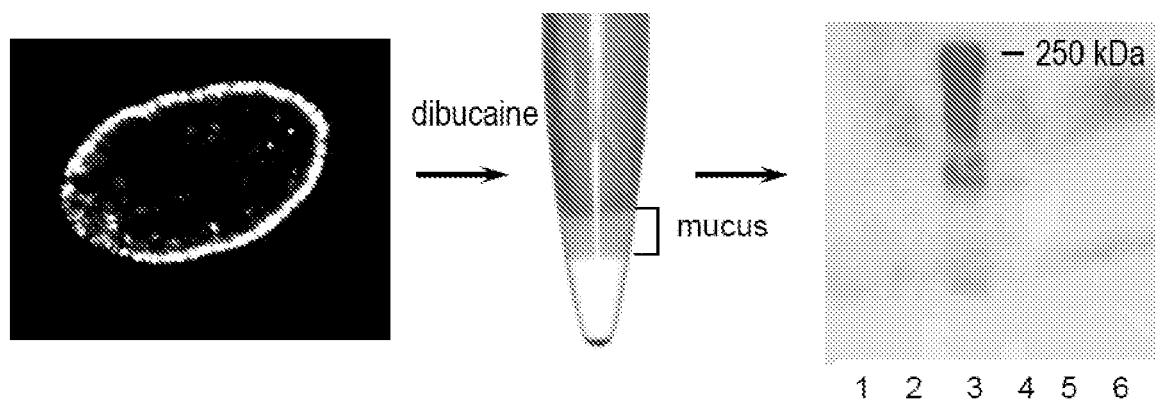

FIG. 6. Western blot of the recombinant Grl1p:H5 protein secreted from *T. thermophila* in response to dibucaine. Cells transformed with the gene for the GrlP1:H5 fusion protein were fixed, permeabilized and reacted sequentially with the mouse mAb 5C5 against the H5 hemagglutinin followed by goat anti-mouse IgG coupled to Texas Red. The panel at the left shows an immunofluorescence confocal image localizing the chimeric protein to cortical mucocysts. Live cells expressing the chimeric protein were harvested by low-speed centrifugation and the spent culture medium retained. Cells were then washed in buffer and induced to secrete their mucocyst contents by treatment with 20 mM dibucaine. After low speed centrifugation, the cell pellet, mucus layer and supernatant fractions (center panel) were separated, and equivalent volumes from each sample fractionated by SDS-PAGE under non-reducing conditions. Proteins were then transferred to a nitrocellulose filter and subjected to Western blotting with mAb 5C5 (right hand panel). Lanes 2 and 3 (right-hand panel) contain protein from the cell pellet and mucus layer, respectively, following the addition of dibucaine to washed cells. Lane 4 represents the spent culture medium from cells expressing the Grl:H5 fusion protein. Lane 5 represents the soluble supernatant fraction from non-dibucaine treated cells after the removal of cells by low-speed centrifugation. Lane 6 represents the soluble supernatant fraction of dibucaine-treated samples after removal of cells and mucus by low speed centrifugation. The only fraction containing detectable protein is the mucus itself (lane 3). Note that the size of the fusion protein on Western blots (~250 kDa) is appreciably larger than its predicted size (80 kDa).

Figure 7:
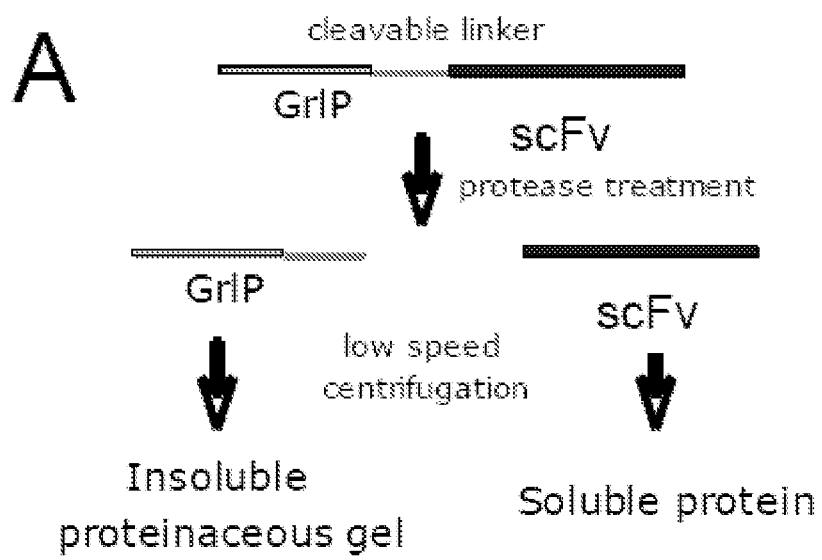
Figure 7:
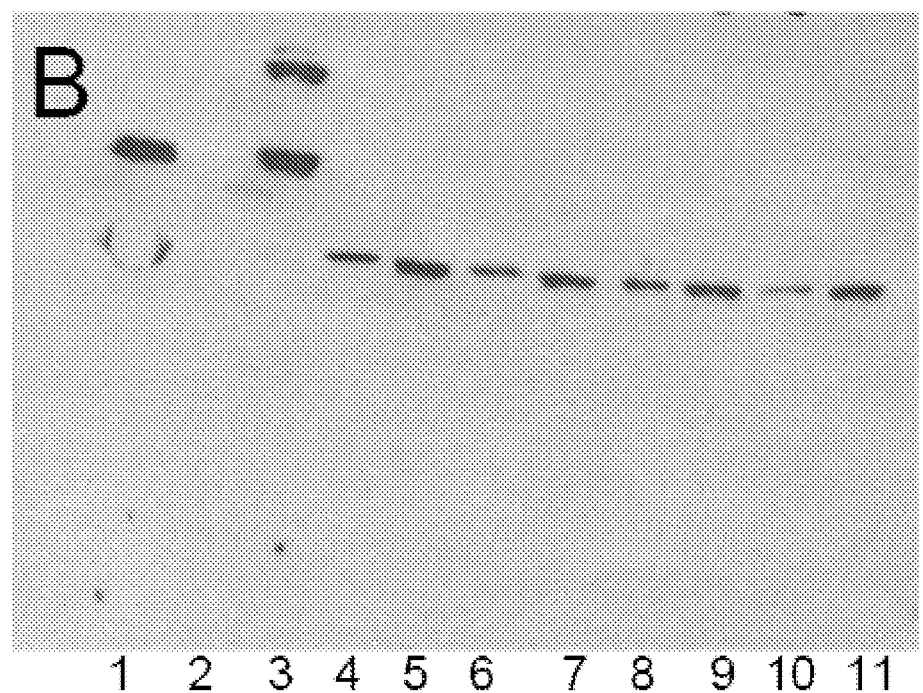

FIG. 7. Release of a recombinant polypeptide from the mucocyst gel matrix by treatment with a site-specific protease. As diagramed in panel A (top), a cleavable linker (the TEV protease cleavage site) was engineered between Grl1p and the C-terminal single-chain antibody Fv fragment (scFv) shown in FIG. 4B. Following regulated secretion stimulated by dibucaine, the mucocyst gel matrix would be expected to contain the recombinant polypeptide (as in FIG. 6 with the chimeric Grl1p:H5 protein). However, treatment of the gel matrix with TEV might be expected to cleave the protein and release the C-terminal scFv fragment into the supernatant as a soluble protein (Panel A). Panel B shows a Western blot that tracks the fate of the recombinant scFv fragment in various fractions following stimulus-dependent secretion from cells using antibodies against an HA-epitope tag engineered into the protein (see FIG. 4). Lanes 1 and 2 contain proteins from cell pellet and high-speed supernatant fractions, respectively, of cell cultures treated with dibucaine to release mucus. Lane 3 contains protein in the mucus fraction obtained after stimulus-dependent secretion. The presence of two bands in lane 3 may be due to incomplete processing of the pro-domain of the Grl1:FscFv fusion protein which would result in two proteins that differ by approximately 18 kDa in size. Lanes 4-11 show the high-speed (soluble) supernatant (even lanes) and insoluble mucus proteins following treatment of mucus with TEV protease for 1 (lanes 4 and 5), 2 (lanes 6 and 7), 3 (lanes 8 and 9) and 5 (lanes 10 and 11) hours. Note the appearance of soluble scFv fragments in all TEV-treated samples. It is estimated that 30-40% of the chimeric scFv protein appears in the soluble phase under the conditions used in this experiment. The resulting His-tagged protein could be readily purified on a Ni-NTA resin following release from the mucocyst gel.

Figure 8B:
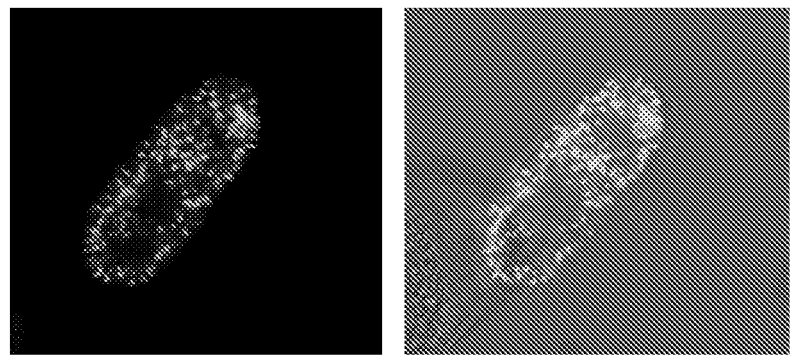
Figure 8C:
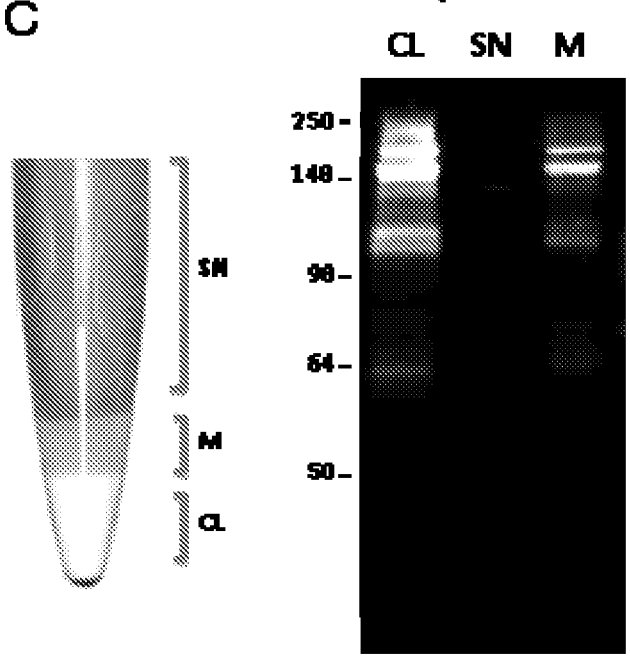

FIG. 8. Mucocyst targeting of H5ΔTMD$^{ProGrl1}$. Shown in FIG. 8A H5ΔTMD$^{ProGrl1}$ construct design and a schematic representation of the gene product and the corresponding amino acid sequence. This construct consists of the H5N1 hemagglutinin protein sequence (plain text) including the N-terminal signal peptide (bold and underlined text) but lacking the carboxy-terminal transmembrane domain. Immediately carboxy-terminal of the H5N1 hemagglutinin sequence is a 10× His tag (bold, italicized and underlined text) and a TEV protease site (plain underlined text). Immediately carboxy-terminal of the TEV protease site is the Grl1 sequence comprising the pro-domain (bold italicized text) and the mature sequence (bold text) but lacking the pre-domain. FIG. 8B show trafficking of H5ΔTMD$^{ProGrl1}$ to secretory granules in *Tetrahymena*. As described herein *Tetrahymena* cells harboring H5ΔTMD$^{ProGrl1}$ expression constructs were induced with CdCl$_2$, fixed and localization of fusion protein determined by immunofluorescence (left panel). Right panel shows a merged image of light and dark field views. FIG. 8C shows H5ΔTMD$^{ProGrl1}$ fusion gene is expressed, targeted to *Tetrahymena* mucocysts and recovered in the mucus phase following regulated secretion. As described herein *Tetrahymena* strains harboring H5ΔTMD$^{ProGrl1}$ expression constructs were induced with CdCl$_2$ and then treated with dibucaine to stimulate regulated exocytosis. Three phases (CL, cell lysate; SN, supernatant; M, mucus) were harvested and analyzed by anti-hemagglutinin Western analysis using the conformation specific 5C5 anti-hemagglutinin antibody. At left is an actual representation of the three phases isolated following centrifugation. H5ΔTMD$^{ProGrl1}$ is predominantly associated with the harvested mucus fraction.

Figure 9B:
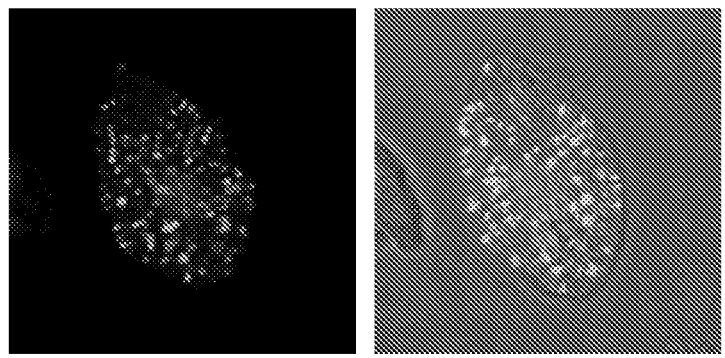
Figure 9C:
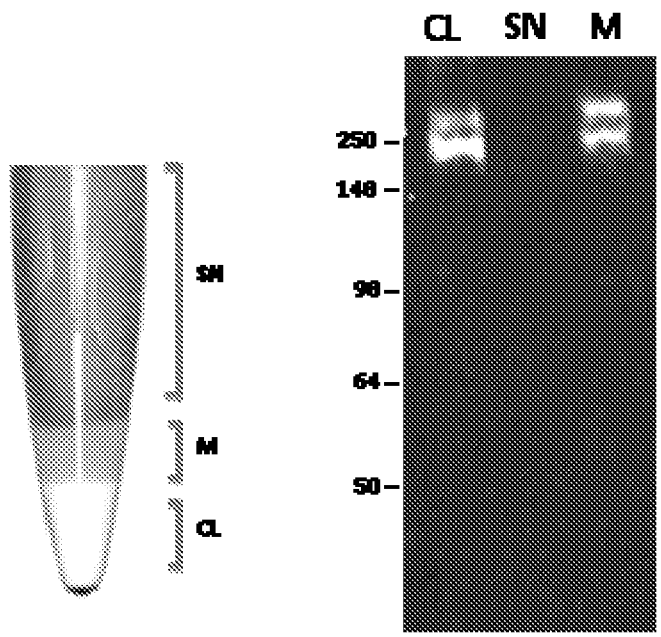

FIG. 9. Mucocyst targeting of H5ΔTMD$^{PrePro}$. FIG. 9A shows H5ΔTMD$^{PrePro}$ construct design and a schematic representation of the gene product and the corresponding amino acid sequence. This construct contains the Grl1 Pre (bold underlined text) and Pro (bold italicized text) domains N-terminal of the mature H5N1 hemagglutinin protein sequence (plain text) that lacks the native amino-terminal signal peptide and carboxy-terminal transmembrane domain. The fusion construct additionally contains a 10× His tag at the carboxy-terminus (bold, italicized underlined text). FIG. 9B shows trafficking of H5ΔTMD$^{PrePro}$ to secretory granules in *Tetrahymena*. As described herein *Tetrahymena* cells harboring H5ΔTMD$^{PrePro}$ expression constructs were induced with CdCl$_2$, fixed and localization of fusion protein determined by immunofluorescence (left panel). Right panel shows a merged image of light and dark field views. FIG. 9C shows the H5ΔTMD$^{PrePro}$ fusion gene is expressed, targeted to *Tetrahymena* mucocysts and recovered in the mucus phase following regulated secretion. As described herein *Tetrahymena* strains harboring H5ΔTMD$^{PrePro}$ expression constructs were induced with CdCl$_2$ and then treated with dibucaine to stimulate regulated exocytosis. Three phases (CL, cell lysate; SN, supernatant; M, mucus) were harvested and analyzed by anti-hemagglutinin Western analysis using the conformation specific 5C5 anti-hemagglutinin antibody. At left is an actual representation of the three phases isolated following centrifugation. H5ΔTMD$^{PrePro}$ is predominantly associated with the harvested mucus fraction.

Figure 10B:
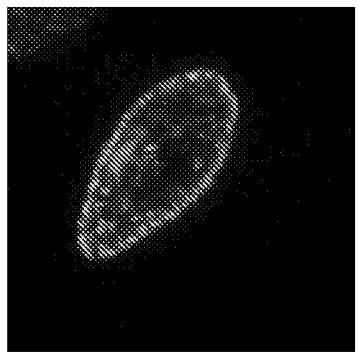
Figure 10C:
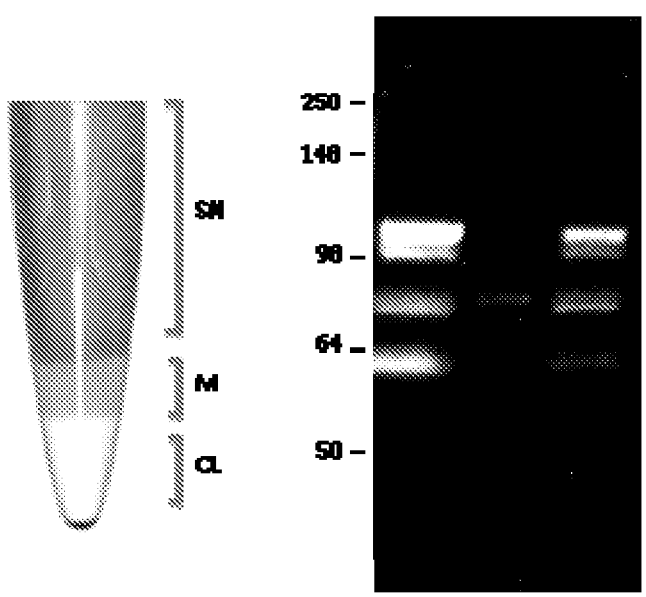

FIG. 10. Mucocyst targeting of H5ΔTMD$^{Igr1}$. FIG. 10A shows H5ΔTMD$^{Igr1}$ construct design and a schematic representation of the gene product and the corresponding amino acid sequence. This construct contains the Igr1 protein (bold text) including the Igr1 signal peptide (Bold, underlined text) and the mature H5N1 hemagglutinin protein sequence (plain text) that lacks the native amino-terminal signal peptide and carboxy-terminal transmembrane domain separated by a TEV protease site (underlined text). The fusion construct additionally contains a 10× His tag at the carboxy-terminus (italicized text). FIG. 10B shows trafficking of H5ΔTMD$^{Igr1}$ to secretory granules in Tetrahymena. As described herein Tetrahymena cells harboring H5ΔTMD$^{Igr1}$ expression constructs were induced with CdCl$_2$, fixed and localization of fusion protein determined by immunofluorescence. FIG. 10C shows the H5ΔTMD$^{Igr1}$ fusion gene is expressed, targeted to Tetrahymena mucocysts and recovered in the mucus phase following regulated secretion. As described herein Tetrahymena strains harboring H5ΔTMD$^{Igr1}$ expression constructs were induced with CdCl$_2$ and then treated with dibucaine to stimulate regulated exocytosis. Three phases (CL, cell lysate; SN, supernatant; M, mucus) were harvested and analyzed by anti-hemagglutinin Western analysis using the conformation specific 5C5 anti-hemagglutinin antibody. At left is an actual representation of the three phases isolated following centrifugation. H5ΔTMD$^{Igr1}$ is predominantly associated with the harvested mucus fraction.

Figure 11A:
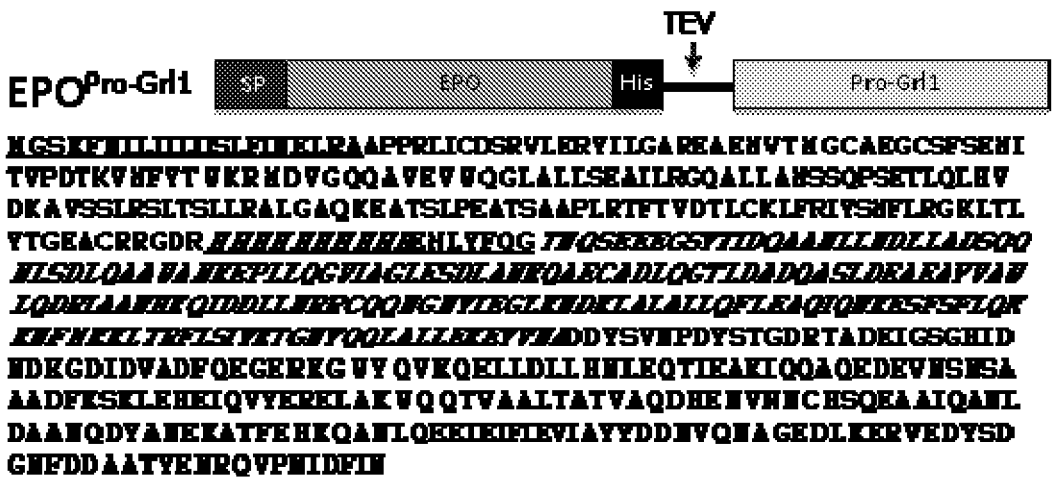
Figure 11B:
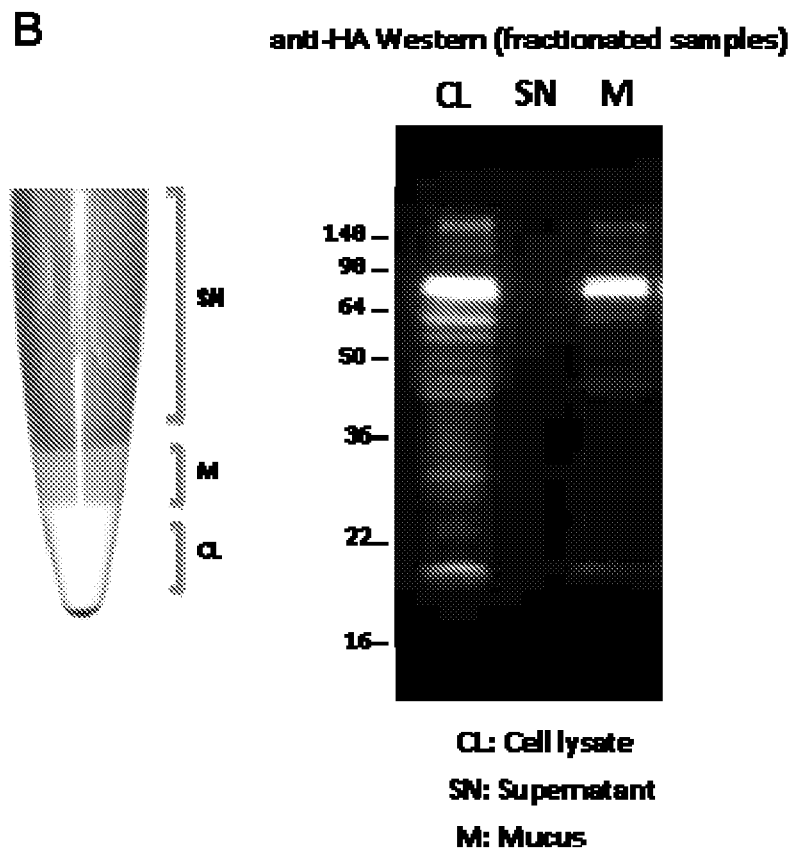

FIG. 11. Mucocyst targeting of EPO$^{ProGrl1}$. FIG. 11A shows EPO$^{ProGrl1}$ construct design and a schematic representation of the gene product and the corresponding amino acid sequence. This construct consists of the feline EPO protein sequence (plain text) including the N-terminal H5N1 hemagglutinin signal peptide (bold and underlined text). Immediately carboxy-terminal of the EPO sequence is a 10× His tag (bold, italicized and underlined text) and a TEV protease site (plain underlined text). Immediately carboxy-terminal of the TEV protease site is the Grl1 sequence comprising the pro-domain (bold italicized text) and the mature sequence (bold text) but lacking the pre-domain. FIG. 11B shows the EPO$^{ProGrl1}$ fusion gene is expressed, targeted to Tetrahymena mucocysts and recovered in the mucus phase following regulated secretion. As described herein Tetrahymena strains harboring EPO$^{ProGrl1}$ expression constructs were induced with CdCl$_2$ and then treated with dibucaine to stimulate regulated exocytosis. Three phases (CL, cell lysate; SN, supernatant; M, mucus) were harvested and analyzed by anti-EPO Western analysis. At left is an actual representation of the three phases isolated following centrifugation. EPO$^{ProGrl1}$ is predominantly associated with the harvested mucus fraction.

Figure 12B:
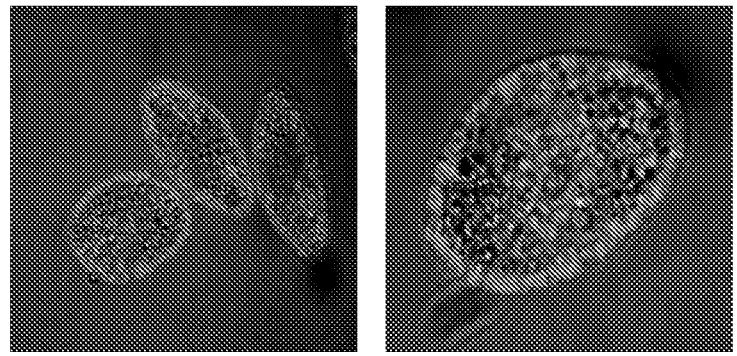
Figure 12C:
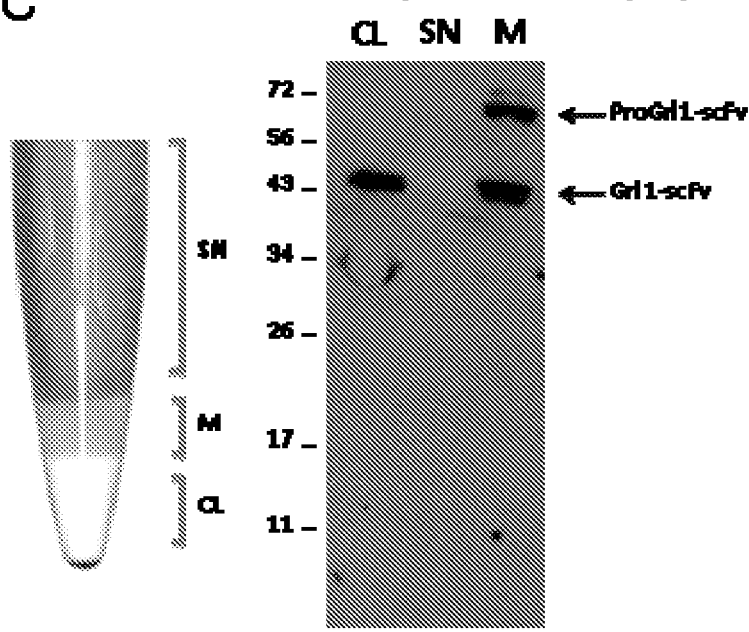

FIG. 12. Mucocyst targeting of scFv$^{Grl1}$. FIG. 12A shows scFv$^{Grl1}$ construct design and a schematic representation of the gene product and the corresponding amino acid sequence. This construct contains the Tetrahymena Grl1 protein (bold text) including the Grl1 signal peptide pre-(Bold, underlined text) and pro-(bold, italicized text) domains fused to the anti-anthrax PA toxin single chain antibody (plain text). Dividing the Grl1 and scFv sequences are a TEV protease site (underlined text), a 6× His tag (underlined, bold and italicized text) and a HA epitope tag (bold, italicized text). FIG. 12B show trafficking of scFv$^{Grl1}$ to secretory granules in Tetrahymena. As described herein Tetrahymena cells harboring scFv$^{Grl1}$ expression constructs were induced with CdCl$_2$, fixed and localization of fusion protein determined by immunofluorescence using an anti-HA primary antibody and a rhodamine-conjugated secondary antibody. FIG. 12C shows the scFv$^{Grl1}$ fusion gene is expressed, targeted to Tetrahymena mucocysts and recovered in the mucus phase following regulated secretion. As described herein Tetrahymena strains harboring scFv$^{Grl1}$ expression constructs were induced with CdCl$_2$ and then treated with dibucaine to stimulate regulated exocytosis. Three phases (CL, cell lysate; SN, supernatant; M, mucus) were harvested and analyzed by anti-HA Western analysis. At left is an actual representation of the three phases isolated following centrifugation. scFv$^{Grl1}$ is predominantly associated with the harvested mucus fraction. Highlighted in the mucus fraction are two forms of the fusion protein that corresponds to unprocessed Grl1 fusion (ProGrl1-scFv) and processed Grl1 fusion where the PrePro domain have been cleaved leaving the mature Grl1 protein fused to scFv (Grl1-scFv).

Figure 13B:
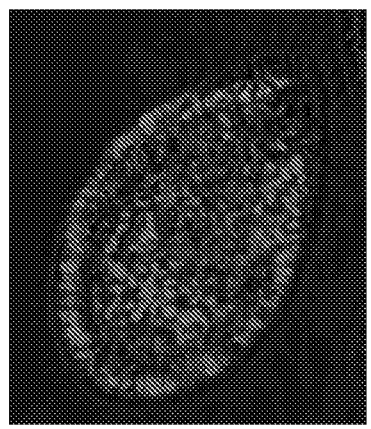
Figure 13C:
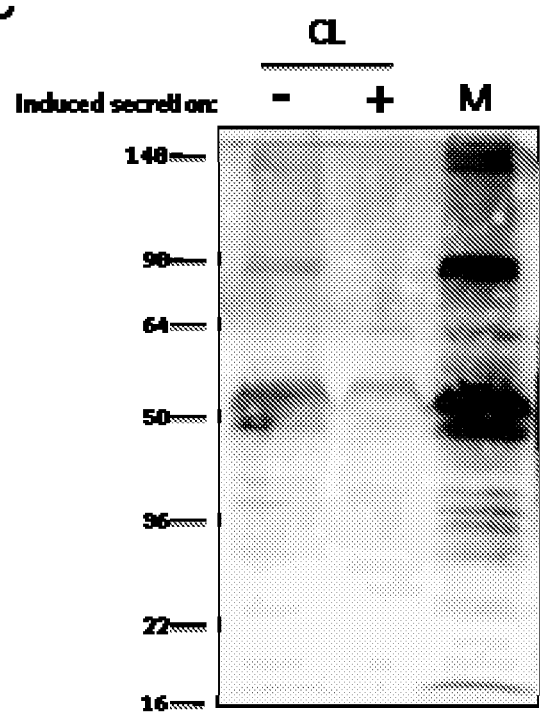

FIG. 13. Mucocyst targeting of pfs48/45$^{Grl4}$. FIG. 13A shows pfs48/45$^{Grl4}$ construct design and a schematic representation of the gene product and the corresponding amino acid sequence. This construct contains the Tetrahymena Grl4 protein (bold text) including the Grl4 signal peptide pre-(Bold, underlined text) and pro-(bold, italicized text) domains fused to the malarial antigen pfs48/45 (plain text). Carboxy-terminus of pfs48/45 is a 6× His tag (underlined text), the carboxy-terminal domain of the immobilization antigen variant B protein of Ichthyophthirius multifiliis (italic text) and a HA epitope tag (Bold, italicized and underlined text). FIG. 13B shows trafficking of pfs48/45$^{Grl4}$ to secretory granules in Tetrahymena. As described herein Tetrahymena cells harboring pfs48/45$^{Grl4}$ expression constructs were induced with CdCl$_2$, fixed and localization of fusion protein determined by immunofluorescence using an anti-HA primary antibody and a rhodamine-conjugated secondary antibody. FIG. 13C shows the pfs48/45$^{Grl4}$ fusion gene is expressed, targeted to Tetrahymena mucocysts and recovered in the mucus phase following regulated secretion. As described herein Tetrahymena strains harboring pfs48/45$^{Grl4}$ expression constructs were induced with CdCl$_2$ and then treated with dibucaine to stimulate regulated exocytosis. Mucus (M) and Cell lysate (CL) fraction before and after induction of regulated secretion were harvested and analyzed by anti-HA Western analysis. pfs48/45$^{Grl4}$ is predominantly associated with the harvested mucus fraction. In the mucus fraction three forms of the fusion protein correspond to unprocessed Grl4 fusion (approximately 80 kDa), processed Grl4 fusion where the PrePro domain have been cleaved leaving the mature Grl4 protein fused to pfs48/45 (50 kDa) and a third species (160 kDa) that most likely represents a dimerized form of the unprocessed Grl4 fusion.

Figure 14B:
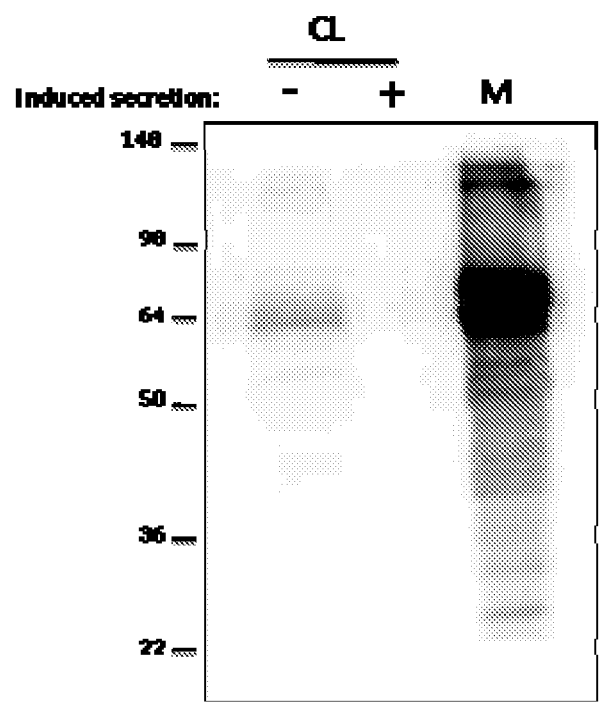

FIG. 14. Mucocyst targeting of pfs48/45$^{PrePro}$. FIG. 14A shows pfs48/45$^{PrePro}$ construct design and a schematic representation of the gene product and the corresponding amino acid sequence. This construct contains the Tetrahymena Grl1 protein Pre-(underlined, bold text) and Pro-(bold text) domains fused to the malarial antigen pfs48/45 (plain text). Carboxy-terminus of pfs48/45 is a 6× His tag (underlined text), the carboxy-terminal domain of the immobilization antigen variant B protein of Ichthyophthirius multifiliis (italic text) and a HA epitope tag (Bold, italicized and underlined text). FIG. 14B shows the pfs48/45$^{PrePro}$ fusion gene is expressed, targeted to Tetrahymena mucocysts and recovered in the mucus phase following regulated secretion. As described herein *Tetrahymena* strains harboring pfs48/45$^{PrePro}$ expression constructs were induced with CdCl$_2$ and then treated with dibucaine to stimulate regulated exocytosis. Mucus (M) and Cell lysate (CL) fraction before and after induction of regulated secretion were harvested and analyzed by anti-HA Western analysis. pfs48/45$^{PrePro}$ is predominantly associated with the harvested mucus fraction.

Figures 15A, 15B:
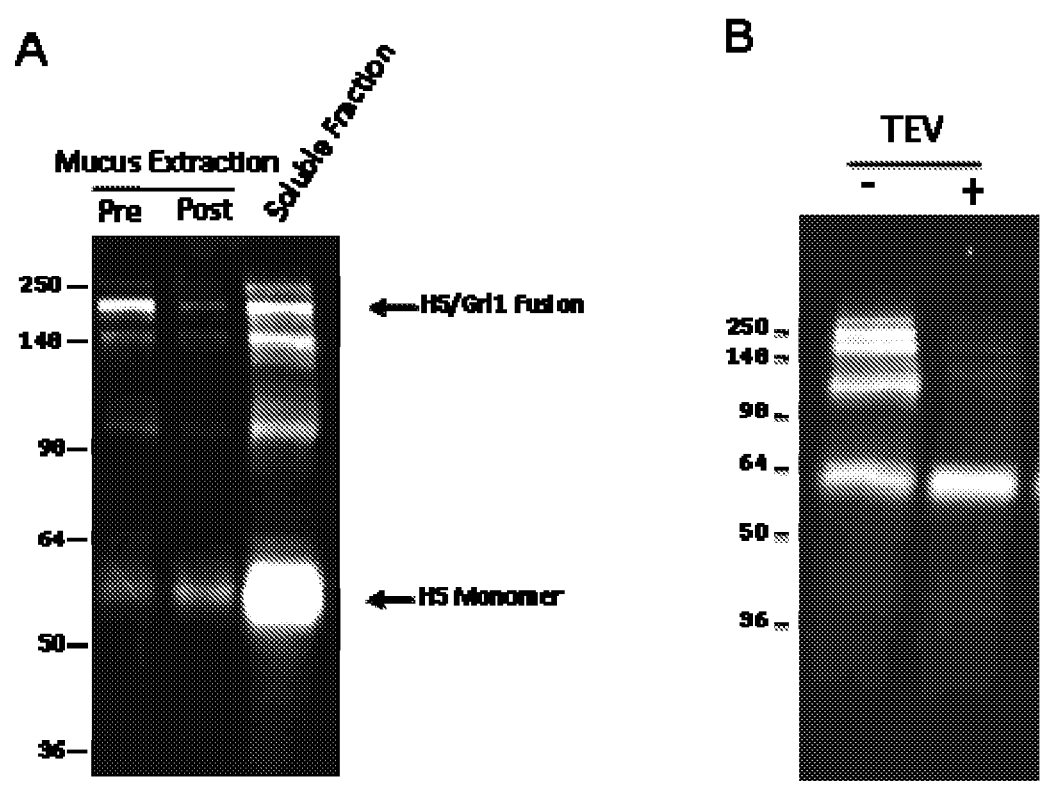
Figure 15C:
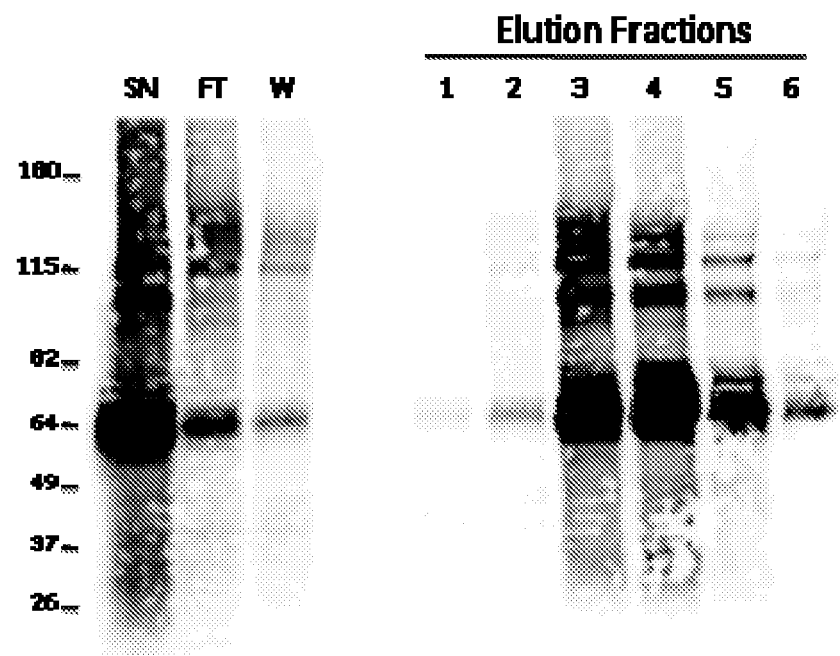
Figure 15D:
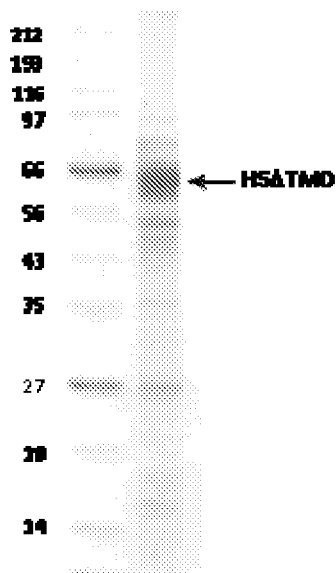

FIG. 15. Extraction and purification of H5ΔTMD$^{ProGrl1}$. FIG. 15A shows extraction H5ΔTMD$^{ProGrl1}$. Cells were induced to express H5ΔTMD$^{ProGrl1}$, mucocyst contents released and soluble protein extracted from harvested mucus as described herein. Western analysis was carried out with the anti-H5N1 hemagglutinin antibody 5C5 as described above. Shown is the mucus fraction before and after extraction and the resulting soluble fraction. Highlighted are the H5ΔTMD-Grl1 fusion and H5ΔTMD monomer proteins. FIG. 15B shows a Western analysis using the 5C5 antibody of the extracted soluble fraction with and without TEV protease treatment. Note the conversion of high-molecular weight H4ΔTMD$^{ProGrl1}$ fusion protein to the H5ΔTMD monomer (~64 kDA). FIG. 15C shows purification of H5ΔTMD by Ni-NTA affinity chromatography. TEV treated soluble extracted fraction was passed over Ni-NTA resin and eluted in buffer containing imidazole. Shown is a Western analysis using the 5C5 antibody of purification fractions. SN, Soluble extract; FT, Ni-NTA flow-through; W, wash fraction. FIG. 15D shows SDS-PAGE analysis of purified soluble H5ΔTMD.

Figures 16A, 16B:
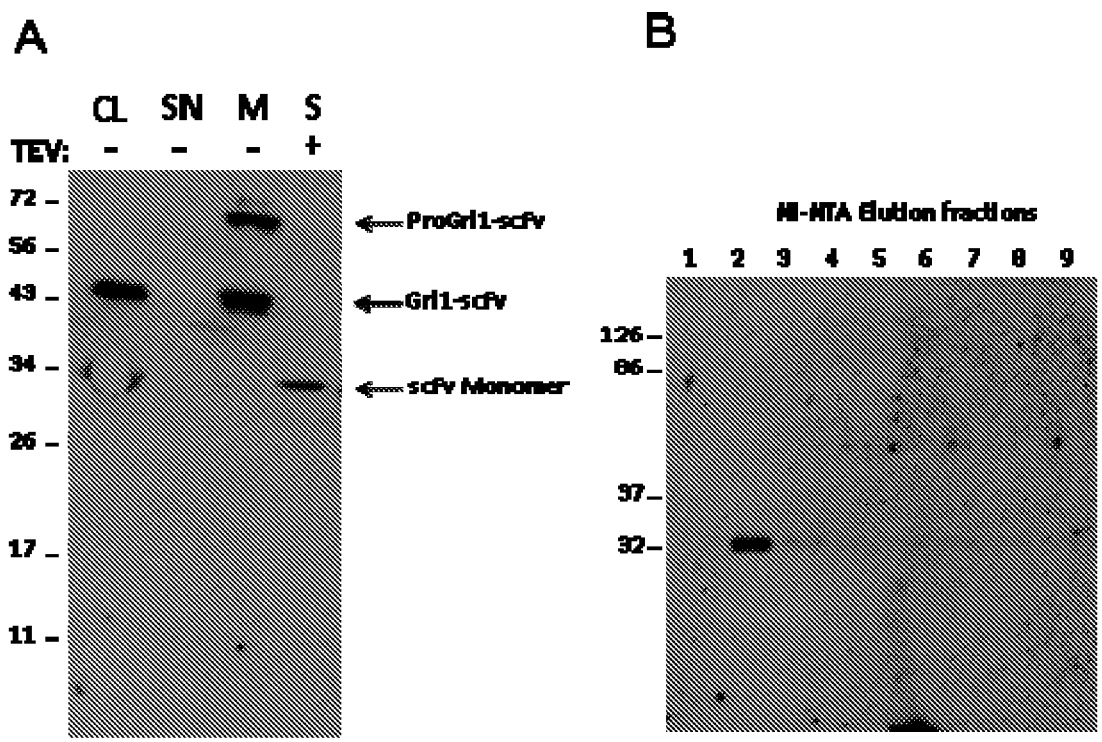

FIG. 16. Extraction and purification of scFv$^{Grl1}$. FIG. 16A shows extraction of scFv$^{Grl1}$. Mucus containing scFv$^{Grl1}$ was treated directly with TEV protease as described herein. Anti-HA Western analysis was performed on fractionated samples: CL, Cell Lysate, SN, supernatant following regulated secretion; M, mucus; S, soluble fraction following treatment of Mucus with TEV protease. Highlighted are differentially processed forms of scFv$^{Grl1}$ including soluble scFv monomer, Grl1-scFv where the Grl1 prodomain has been cleaved in vivo, and scFv$^{Grl1}$ fusion protein (depicted as ProGrl1-scFv in this figure). FIG. 16B shows purification of scFv by Ni-NTA affinity chromatography. Shown is an anti-HA Western analysis of elution fractions following Ni-NTA chromatography of the soluble fraction derived from TEV treatment of mucus containing scFv$^{Grl1}$.

Figure 17:
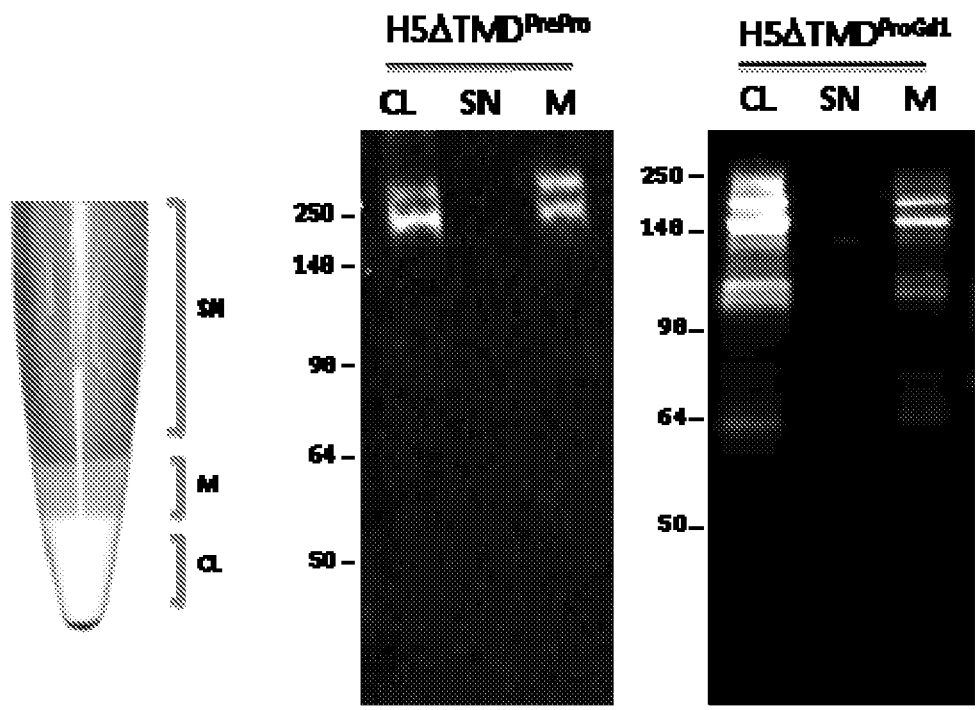

FIG. 17. H5ΔTMD$^{PrePro}$ and H5ΔTMD$^{ProGrl1}$ fusion genes are expressed, targeted to *Tetrahymena* mucocysts and recovered in the mucus phase following regulated secretion. As described herein *Tetrahymena* strains harboring H5ΔTMD$^{PrePro}$ and H5ΔTMD$^{ProGrl1}$ expression constructs were induced with CdCl$_2$ and then treated with dibucaine to stimulate regulated exocytosis. Three phases (CL, cell lysate; SN, supernatant; M, mucus) were harvested and analyzed by anti-hemagglutinin Western analysis using the conformation specific 5C5 anti-hemagglutinin antibody. At left is an actual representation of the three phases isolated following centrifugation. Both H5ΔTMD$^{PrePro}$ and H5ΔTMD$^{ProGrl1}$ were predominantly associated with the harvested mucus fraction.

Figure 18:
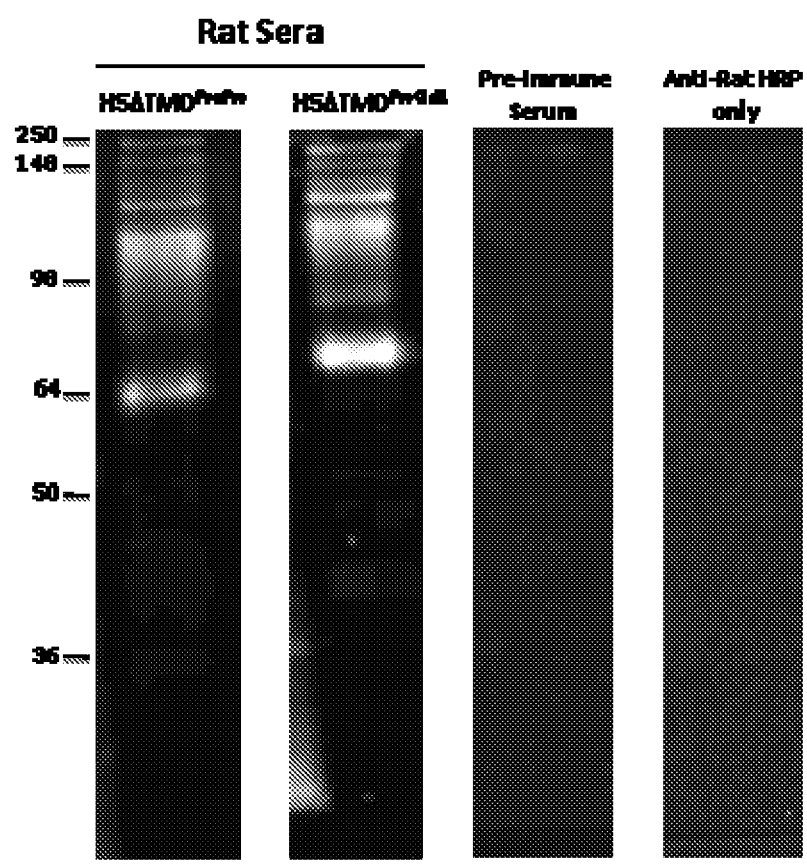

FIG. 18. Mucus associated H5ΔTMD$^{PrePro}$ and H5ΔTMD$^{ProGrl1}$ elicit an immune response in animals. Rats were immunized with either mucus-associated H5ΔTMD$^{PrePro}$ or mucus-associated H5ΔTMD$^{ProGrl1}$. Three weeks post-injection sample bleeds were tested for the presence of anti-hemagglutinin antibody by Western analysis using a commercially available insect cell-derived recombinant H5N1 hemagglutinin. Both rat sera samples are positive for anti-hemagglutinin antibody (2 panels on left). Control westerns using either pre-immune sera or secondary antibody alone were negative (2 panels on right).

DETAILED DESCRIPTION OF THE INVENTION

All publications, patent applications, patents, and other references mentioned herein are incorporated by reference in their entirety. The patent, scientific and technical literature referred to herein establish knowledge that was available to those skilled in the art at the time of filing. The entire disclosures of the issued U.S. patents, published and pending patent applications, and other publications that are cited herein are hereby incorporated by reference to the same extent as if each was specifically and individually indicated to be incorporated by reference. In the case of any inconsistencies, the present disclosure will prevail.

Definitions.

All scientific and technical terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "ciliates" means eukaryotes belonging to the kingdom Chromalveolata, the superphylum Alveolata, and the phylum Ciliophora. Ciliates are complex protozoa characterized by the presence of cilia on their cell surfaces and dimorphic nuclei consisting of a macronucleus and one or more micronuclei.

As used herein, "*Tetrahymena* spp." refers to ciliate protozoa in the family of Tetrahymenidae. Exemplary *Tetrahymena* spp. include, but are not limited to, *T. thermophila* and *T. pyriformis*.

As used herein, the term the term "dense core granule" refers to a subset of the secretory organelles in ciliates that have electron dense cores and discharge in a stimulus-dependent fashion. Exemplary dense core granules include, but are not limited to, mucocysts in *Tetrahymena* spp. and trichocysts in *Paramecium* spp.

As used herein, the term "mucocyst" refers to secretory organelles in ciliates, also referred to as "cortical granules," that secrete or discharge a proteinaceous mucus in response to a secretory stimulus.

As used herein, a "secretory stimulus" refers to a condition or treatment that directly or indirectly stimulates or increases the release of a protein from a dense core granule (e.g., a mucocyst). Exemplary secretory stimuli suitable for use with the methods disclosed herein include, but are no limited to, treatment with a secretagogue, mechanical shock, cross-linking of surface antigens and electroshock (e.g., electroporation).

As used herein, the term "secretagogue" refers to a compound or agent that directly or indirectly stimulates or increases the release of a protein from a dense core granule (e.g., a mucocyst). Exemplary secretagogues suitable for use with the methods disclosed herein include, but are no limited to, dibucaine, NaCl, Alcian blue, ~0.25M sucrose and compounds that increase intracellular Ca$^{2+}$ levels (e.g., calcium ionophores such as A23187).

The term "targeting polypeptide" means a polypeptide (a "secretory peptide") that, as a component of a larger polypeptide, directs the larger polypeptide through a secretory pathway of a cell in which it is synthesized. The larger polypeptide can be cleaved to remove the secretory peptide during transit through the secretory pathway.

As used herein, the term "endoplasmic reticulum-targeting polypeptide" means a sequence of amino acids, present at the N-terminus of a polypeptide, that causes the polypeptide to be inserted into the endoplasmic reticulum (ER) upon synthesis. Endoplasmic reticulum-targeting polypeptides typically comprise 5-10 hydrophobic amino acids that bind to a signal recognition particle (SRP) which facilitates transport into the ER. Some endoplasmic reticulum-targeting polypeptides are cleaved from the polypeptide by a signal peptidase present within the ER. Endoplasmic reticulum-targeting polypeptides are a subset of the class of polypeptides variously known as leader sequences, signal sequences, targeting signals, transit peptides, or localization signals, which target polypeptides to organelles such as the nucleus, mitochondria, chloroplasts, secretory granules and ER. For some proteins, including ciliate Grl proteins, the endoplasmic reticulum-targeting polypeptide may be referred to as a "pre-domain."

As used herein, the term "mucocyst-targeting polypeptide" means a sequence of amino acids that causes the polypeptide to be trafficked into the cortical secretory granules (i.e., mucocysts) of ciliates as the granules are formed. Mucocyst-targeting polypeptides typically are located at the N-terminus of the polypeptide, or immediately C-terminal to an endoplasmic reticulum-targeting polypeptide. Some mucocyst-targeting polypeptides are cleaved from the polypeptide by a site-specific protease present within the granules. Endoplasmic reticulum targeting polypeptides are a subset of the class of polypeptides variously known as leader sequences, signal sequences, targeting signals, transit peptides, or localization signals, which target polypeptides to organelles such as the nucleus, mitochondria, chloroplasts, secretory granules and ER. For some proteins, including ciliate Grl proteins, the mucocyst-targeting polypeptide may be referred to as a "pro-domain."

As used herein, the term "cleavage site" refers to a specific sequence of amino acids that can be cleaved specifically by a cleavage agent, such as a protease, or that self-cleaves, such as an intein sequence.

As used herein, the term "cleavable linker" refers to a sequence of amino acids that comprises a cleavage site and that joins two structural domains of a protein.

As used herein, the term "antibody" is intended to embrace naturally produced antibodies, recombinantly produced antibodies, monoclonal antibodies, and polyclonal antibodies, as well as antibody fragments such as Fab fragments, F(ab')$_2$ fragments, Fv fragments, and single-chain Fv fragment (scFv). Useful antibodies include all immunoglobulin classes, such as IgM, IgG, IgD, IgE, IgA and their subclasses. Antibodies may be produced by standard methods, well known in the art. See, e.g., Pluckthun (1990), *Nature* 347: 497-498; Huse et al. (1989), *Science* 246:1275-1289; Chaudhary et al. (1990), *Proc. Natl. Acad. Sci. USA* 87:1066-1070; Mullinax et al. (1990), *Proc. Natl. Acad. Sci. USA* 87:8095-8099; Berg et al. (1991), *Proc. Natl. Acad. Sci. USA* 88:4723-4727; Wood et al. (1990), *J. Immunol.* 145:3011-3016; and references cited therein.

As used herein, the term "heterologous" means, with respect to two or more genetic or protein sequences, that the sequences do not occur in the same physical relation to each other in nature and/or do not naturally occur within the same genome or protein. For example, a genetic construct may include a coding sequence which is operably joined to one or more regulatory sequences, or to one or more other coding sequences, and these sequences are considered heterologous to each other if they are not operably joined in nature and/or they are not found in the same relation in a genome in nature. Similarly, a protein may include a first polypeptide sequence which is joined by a standard peptide bond to a second polypeptide sequence, and these sequences are considered heterologous to each other if they are not found in the same relation in any protein or proteome in nature.

As used herein, the term "endogenous" means, with respect to a genetic or protein sequence, that the sequence occurs naturally in the same physical relation to a specified sequence, or occurs naturally in a specified cell or genome. For example, a genetic construct may include a coding sequence which is operably joined to one or more regulatory sequences, and the regulatory sequences are considered endogenous if they are operably joined to the coding sequence in nature, and/or they are found in the same relation in a genome in nature. Similarly, a protein that occurs naturally in a specified cell type or species, is considered endogenous to that cell or species.

As used herein, the term "homolog" means a protein which is evolutionarily-related to and shares substantial structural and functional similarity with a reference protein in a different species (e.g., *Tetrahymena* spp. Grl proteins).

As used herein, the term "promoter" means a nucleotide sequence which is capable of binding RNA polymerase and initiating transcription of a downstream or 3' coding sequence.

As used herein, the term "selectable marker" means any genetic sequence which, when expressed, has a biochemical or phenotypic effect which is dominant and selectable by the presence or absence of a selection agent.

As used herein with respect to protein preparations, the term "substantially pure" means a preparation which contains at least 60% (by dry weight) the protein of interest, exclusive of the weight of other intentionally included compounds. In some embodiments, the -preparation is at least 75%, at least 90%, or at least 99%, by dry weight the protein of interest, exclusive of the weight of other intentionally included compounds. Purity can be measured by any appropriate method, e.g., column chromatography, gel electrophoresis, or HPLC analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. For such preparations containing two or more proteins of the invention, the total weight of the proteins of the invention can be at least 75%, at least 90%, or at least 99%, of the total dry weight of the preparation, exclusive of the weight of other intentionally included compounds. Thus, if the proteins of the invention are mixed with one or more other proteins(e.g., serum albumin) or compounds (e.g., diluents, detergents, excipients, salts, polysaccharides, sugars, lipids) for purposes of administration, stability, storage, and the like, the weight of such other proteins or compounds is ignored in the calculation of the purity of the preparation.

As used herein, the term "transform" means to introduce into a cell an exogenous nucleic acid or nucleic acid analog which replicates within that cell, that encodes a polypeptide sequence which is expressed in that cell (with or without integration into the genome of the cell), and/or that is integrated into the genome of that cell so as to affect the expression of a genetic locus within the genome. The term "transform" is used to embrace all of the various methods of introducing such nucleic acids or nucleic acid analogs, including, but not limited to the methods referred to in the art as transformation, transfection, transduction, or gene transfer, and including techniques such as microinjection, DEAEdextran-mediated endocytosis, calcium phosphate coprecipitation, electroporation, liposome-mediated transfection, ballistic injection, viral-mediated transfection, and the like.

As used herein, the term "vector" means any genetic construct, such as a plasmid, phage, transposon, cosmid, chromosome, virus, virion, etc., which is capable transferring nucleic acids between cells. Vectors may be capable of one or more of replication, expression, and insertion or integration, but need not possess each of these capabilities. Thus, the term includes cloning, expression, homologous recombination, and knock-out vectors.

As used herein, the terms "increase" and "decrease" mean, respectively, to cause an increase or decrease of at least 5%, as determined by a method and sample size that achieves statistically significance (i.e., $p<0.1$).

As used herein, the term "statistically significant" means having a probability of less than 10% under the relevant null hypothesis (i.e., $p<0.1$).

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, ..., 0.9, 0.99, 0.999, or any other real values $\geq 0$ and $\leq 2$, if the variable is inherently continuous.

As used herein, unless specifically indicated otherwise, the word "or" is used in the inclusive sense of "and/or" and not the exclusive sense of "either/or."

As used herein and in the appended claims, the use of singular forms of words, and the use of the singular articles "a," "an" and "the," are intended to include and not exclude the use of a plurality of the referenced term unless the content clearly dictates otherwise.

The present invention provides methods and compositions for producing a desired heterologous polypeptide in a ciliate (e.g., *Tetrahymena thermophila* or *Tetrahymena pyriformis*) by targeting the heterologous polypeptide to mucocysts as a fusion protein with a mucocyst-targeting sequence or endogenous soluble mucocyst-targeted protein, stimulating regulated secretion from the mucocysts, and purifying the heterologous fusion protein from the resulting extra-cellular matrix produced by the mucocyst discharge.

In some embodiments, the fusion protein comprises a polypeptide which targets the fusion protein to the mucocysts, and which includes a sequence which is cleaved by a protease endogenous to the mucocysts. As a result, all or some of the mucocyst-targeting sequences are removed from the heterologous polypeptide in vivo, enhancing its solubility, and facilitating its separation from the extracellular matrix produced by discharge of the mucocysts.

The proteins stored by ciliates are distinctive in terms of their structures and ability to self-associate upon granule discharge. Whereas the proteins released naturally by mammalian cells are soluble following exocytosis, the majority of proteins discharged from storage granules of ciliates self-associate, forming large macromolecular aggregates. In certain embodiments, the soluble recombinant proteins of the invention, can be separated from the insoluble endogenous mucocyst proteins which form an extracellular matrix after regulated secretion.

Thus, in one aspect the invention employs a different approach to recombinant protein production than in prior art methods which require lysis of the cells followed by purification from the lysate, or which require constitutive expression or regulated secretion of soluble proteins into a culture medium followed by purification from the medium. In certain embodiments, the invention exploits the regulated and simultaneous discharge of mucocysts to secrete the desired soluble recombinant proteins at high concentration (rather than the low concentration that usually results from slow, continuous secretion into culture medium), and further exploits the insoluble nature of the extracellular matrix material to separate the endogenous mucocyst proteins from the desired soluble recombinant proteins.

In certain embodiments, the invention relies on the natural, insoluble matrix material secreted by ciliates in order to obtain highly purified recombinant proteins in a simple, one-to-two step process. To accomplish this, molecular cloning techniques are used to direct fusion proteins comprising desired heterologous polypeptides to the cortical mucocysts of the ciliates by linking them to one or more mucocyst-targeting polypeptides. In certain embodiments, the mucocyst-targeting sequences are then cleaved by endogenous processes to release the desired soluble recombinant protein within the mucocysts. Mucocyst discharge is triggered with an appropriate stimulus to release the fusion proteins into the extracellular space in association with the proteinaceous mucocyst matrix.

In certain embodiments, the gel matrix is then harvested by low-speed centrifugation or filtration, and the desired a heterologous polypeptide is recovered in a purified form by dissociation (with or without cleavage from other fusion protein sequences) from the matrix. This approach permits purification of proteins to near homogeneity in a very rapid process that obviates the need for serial rounds of purification following cell lysis or secretion by conventional routes. In other embodiments, the gel matrix and intact ciliate cells are then harvested by low-speed centrifugation or filtration, and the desired heterologous polypeptide is recovered in a purified form by dissociation (with or without cleavage from other fusion protein sequences) from the matrix. This approach permits purification of proteins to near homogeneity in a very rapid process that obviates the need for serial rounds of purification following cell lysis or secretion by conventional routes.

Significantly, the present invention exploits (a) the limited number of proteins present in the mucocysts of ciliates to reduce the complexity of the protein mixture to be purified, (b) the regulated secretion mechanism of mucocysts to cause synchronized and nearly instantaneous secretion by a population of cells, and (c) the insoluble extracellular matrices produced by the mucocyst discharge for protein isolation.

In addition, as described below, the invention provides nucleic acid constructs encoding the fusion proteins of the invention, cassettes for producing such fusion proteins between targeting sequences and sequences encoding a desired heterologous polypeptide, methods for targeting a desired heterologous polypeptide to a mucocyst, methods for producing a desired heterologous polypeptide in a ciliate, methods for inducing the regulated secretion of a desired heterologous polypeptide from a ciliate, and methods for purifying a desired heterologous polypeptide from the extracellular matrix resulting from regulated secretion by the mucocysts.

Along with streamlined purification, a further advantage of this approach is the apparent absence of secreted proteases following regulated secretion from mucocysts. Whereas stimulus-dependent secretion in mammalian cells is typically accompanied by the release of lysosomal proteases that are potentially damaging to expressed recombinant polypeptides (Andrews (2000)), mass spectrophotometric analysis of proteins released from *Tetrahymena* spp. following regulated exocytosis has revealed a paucity of such enzymes, thus giving the ciliate expression system an advantage relative to mammalian expression systems. Therefore, because the methods described herein result in little or no release of lysosomal proteases into the medium upon regulated secretion, the invention provides for improved protein preparations, with reduced levels of proteases and reduced levels of proteolytic fragments. Consequently, yield and fidelity are improved and production costs are reduced.

Mucocyst-Targeting of Heterologous Polypeptides

Ciliates engage in regulated secretion of proteins stored in cortical secretory organelles (granules), which are discharged in a stimulus-dependent or regulated fashion (Turkewitz et al. (2000); Turkewitz (2004)). In *Tetrahymena* spp., these dense core granules are termed mucocysts.

Each *Tetrahymena* spp. cell contains numerous mucocysts docked at the plasma membrane. Upon stimulation, the discharge of the mucocyst contents occurs in a rapid and synchronous manner (Satir (1977)). The signal sequences that target proteins to the dense core granules are not yet well-characterized, but small stable loops appear to be important determinants in several systems (Chanat et al. (1993); Cool et al. (1995); Cool et al. (1997); Glombik et al. (1999); Roy et al. (1991); Zhang et al. (1999)), and the sequences are readily identified by deletion analysis. Regions of limited sequence similarity border known proteolytic processing sites in Grl proteins and accordingly may be targets for protease processing (Bradshaw et al. (2003)).

At least twelve proteins localize to mucocysts in *Tetrahymena* spp. (Chilcoat et al. (1996); Haddad et al. (2002); Bradshaw et al. (2003); Cowan et al. (2005); Bowman et al. (2005a)). The most abundant of these, known as granule lattice proteins (Grls), form a crystalline array that fills the granule space. The genome of *Tetrahymena* spp. contains at least ten GRL genes, and the granule cores in *Tetrahymena* spp. comprise a cargo of polypeptide-based lattices of proteins derived from proteolytically processed Grl precursors (Collins and Wilhelm (1981); Bradshaw et al. (2003)).

The invention employs fusion proteins of mucocyst-targeting polypeptides to direct the trafficking of a desired heterologous polypeptide to the mucocysts of a ciliate. In nature, polypeptides are trafficked to and between the membrane-bound compartments (e.g., the endoplasmic reticulum, the Golgi apparatus, lysosomes, vacuoles, secretory vesicles or granules, etc.) based, in part, upon the presence of N-terminal "leader sequences" or "signal sequences." These same targeting sequences can be employed to target heterologous proteins to desired compartments.

Ciliates, such as *Tetrahymena*, also have a constitutive secretory pathway through which many secretory proteins are released. However, the constitutive secretory route does not contribute to the release of Grl proteins, indicating that sorting between the pathways of regulatory secretion and constitutive secretion occurs in *Tetrahymena* spp.

For targeting polypeptides to the mucocysts of ciliates, any of the naturally-occurring targeting sequences of naturally-occurring granule lattice mucocyst proteins can be employed. For example, the signal sequences for Grlp1 have been identified (Chilcoat et al. (1996)) and can be used to direct a fusion protein comprising the signal sequences to the cortical secretory granules in *Tetrahymena* spp. In addition to the N-terminal leader or signal sequences, larger fragments of endogenous mucocyst proteins can be fused to the desired heterologous polypeptides, as long as these larger fragments can include the targeting sequences necessary for trafficking the fusion protein to the mucocysts. For example, entire N-terminal structural domains, or an entire mucocyst-targeted protein, can be fused to the heterologous polypeptide and used as a targeting sequence.

*Tetrahymena thermophila* Grl sequences include, but are not limited to, the Granule Lattice Protein 1 Precursor (SEQ ID NO: 1), Granule Lattice Protein 3 Precursor (SEQ ID NO: 2), Granule Lattice Protein 4 Precursor (SEQ ID NO: 3), Granule Lattice Protein 5 Precursor (SEQ ID NO: 4), and Granule Lattice Protein 7 Precursor (SEQ ID NO: 5). The sequences of homologs from other *Tetrahymena* and other ciliate species are known in the art or can be determined, and these homologs can be used in the inventions described herein.

Granule lattice protein 2 precursor, granule lattice protein 6 precursor, granule lattice protein 9 precursor and granule lattice protein 10 precursor are also suitable for use as targeting sequences in conjunction with the methods and compositions disclosed herein.

Genetic Constructs for Fusion Proteins.

As described herein, a desired heterologous polypeptide can be produced as a fusion protein with a mucocyst-targeting polypeptide. The targeting polypeptide can be an N-terminal leader or signal sequence from an endogenous mucocyst protein, can be a larger fragment of the mucocyst protein, or can be the entire mucocyst protein or a functional homolog thereof.

In accordance with the invention, the mucocyst-targeting polypeptide can comprise a Grl polypeptide, a Grl pre-protein polypeptide, a truncation product of a Grl protein, a fragment of a Grl polypeptide, a polypeptide that is homologous to a Grl, a polypeptide or a polypeptide having a sequence at least 70% identical to the amino acid sequence of a Grl protein and exhibiting mucocyst-targeting activity. In some embodiments, the mucocyst-targeting polypeptide has at least 99%, 97%, 95%, 90%, 80% or 70% amino acid sequence identity to the amino acid sequence of a Grl protein.

Genetic constructs encoding such fusion proteins can readily be prepared by one of skill in the art based upon the universal genetic code, and optionally employing the codon preferences characteristic of the ciliate host. See Larsen et al. (1999); Wuitschick and Karrer (2000); Eisen et al. (2006); and Wuitschick and Karrer (1999).

The genetic constructs can be designed to include a cleavable linker such as protease cleavage site, self-cleaving intein sequence, or flexible linker sequence between the mucocyst targeting polypeptide(s) and the heterologous polypeptide, and/or may be designed to include additional sequences useful for purification of the fusion protein (e.g., poly-His or epitope tags for affinity or immuno purification).

The sequences encoding the fusion protein can be introduced into the cells on expression plasmids, or can be stably integrated into the protist genome (e.g., by homologous recombination, retroviral insertion). When integrated into the genome, the fusion protein sequences can replace (in whole or in part) the endogenous sequences encoding the corresponding mucocyst protein, or can be inserted at a separate genomic location. Targeting sequences useful for secretion of foreign proteins in *Tetrahymena* spp. are described in (Clark et al. (2001)).

The nucleic acid sequences can be cloned using standard cloning procedures in the art, as described by Sambrook et al., Molecular Cloning: A Laboratory Manual, Second Edition, Cold Springs Laboratory, Cold Springs Harbor, N.Y. (1989).

For example, chimeric genes encoding the fusion proteins can be generated by linking coding regions of genes for the heterologous polypeptides to endogenous mucocyst targeting polypeptides (or mucocyst protein fragments or entire mucocyst proteins) either synthetically (38), or by PCR using serial overlap extension. The resulting constructs can then introduced into standard plasmid DNA vectors (e.g., TOPO, Blue-Script, etc.) for amplification in E. coli by chemical transformation, electroporation or any other method known in the art.

Inducing Regulated Secretion in Ciliates.

Figure 2:
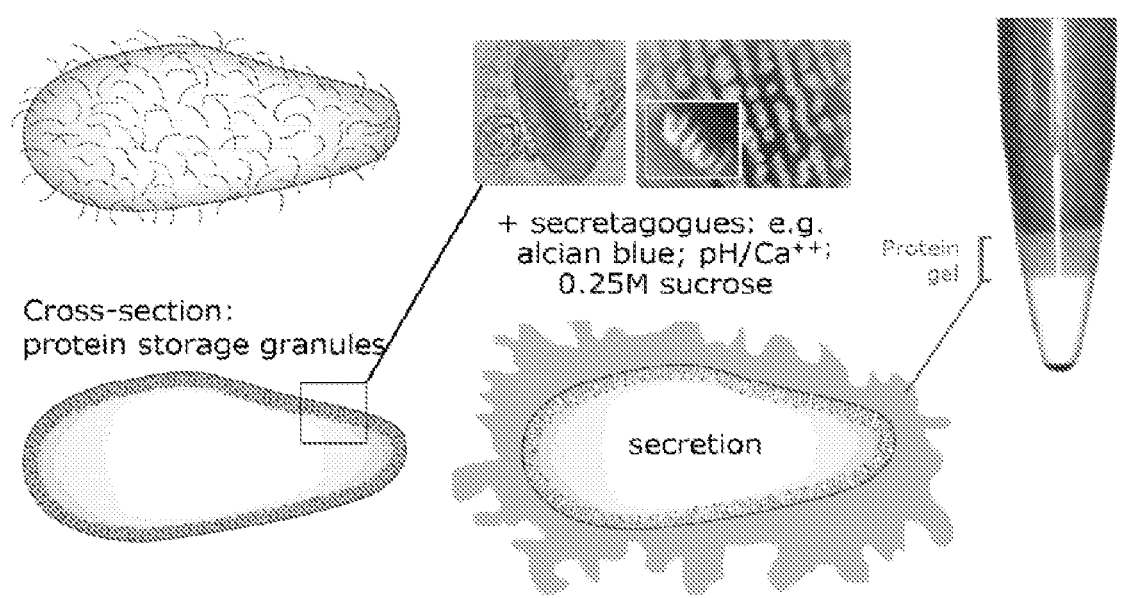
FIG. 2. Stimulus-dependent or regulated secretion in a ciliate, *Tetrahymena*. Top Left: *Tetrahymena* cell with surface-associated cilia. Bottom Left: Cross-section through the cell revealing large numbers of secretory granules (mucocysts) within the cortical cytoplasm. Top Center. Left-hand panel is a transmission electron micrograph showing a single granule docked at the plasma membrane. Right-hand panel is a confocal immunofluorescence image of granules aligned along ciliary rows containing an apically localized granule lattice protein (Bowman et al. (2005a)). Bottom Center. Following treatment of cells with secretagogues, the granules fuse with the plasma membrane and synchronously discharge their contents to the extracellular space. Once hydrated, the granule lattice proteins form an insoluble proteinaceous gel. Top Right. A cell culture induced to secrete was spun at 4,000×g for 10 min. A white, packed cell pellet is visible at the bottom of the tube. The hydrated gel released from mucocysts is present just above the cell pellet and can be readily harvested with a spatula.

Mucocyst discharge can be triggered with appropriate secretory stimuli to release mucocyst-targeted heterologous proteins into the extracellular space in association with the proteinaceous mucocyst gel. Regulated secretion can depend on the level of the stimulus, and can be an all-or-none phenomenon with, in some cases, large amounts of protein being released within a short period of time (on the order of milliseconds). For example, treatment of Tetrahymena spp. cells with dibucaine, or other secretagogues, results in rapid fusion of mucocyst membranes with the plasma membrane, and discharge of the granule contents into the extracellular space (Turkewitz et al. (2000); Turkewitz (2004); Maihle and Satir (1986)) (FIG. 2). A single Tetrahymena spp. cell can store large amounts of protein in its roughly 4,500 mucocysts (Turkewitz et al. (2000); Turkewitz (2004); Chilcoat et al. (1996); Haddad et al. (2002); Cowan et al. (2005); Bowman et al. (2005a); Bradshaw et al. (2003); Bowman et al. (2005b)).

Regulated secretion can be triggered by the presence of chemical mediators known as secretagogues. For example, such mediators can cause increased levels of intracellular calcium ($Ca^{2+}$), which, in turn, trigger fusion of cortical granules with the plasma membrane resulting in a release of the granule contents into the surrounding extracellular space. Examples of secretagogues useful in the invention include, but are not limited to, dibucaine, Alcian blue, elevated NaCl, sucrose and $Ca^{2+}$ ionophores.

Regulated secretion can also be triggered by secretory stimuli other than secretagogues. Examples of such secretory stimuli useful in the invention include, but are not limited to, treatment with mechanical shock, cross-linking of surface antigens, and electroshock (e.g., electroporation).

Unlike regulated secretion in mammalian systems, some proteins stored by the mucocysts of ciliates do not remain soluble following exocytosis. Proteins discharged from ciliated protozoa such as Tetrahymena and Paramecium self-associate upon granule discharge and form macromolecular aggregates. In the case of Paramecium, the released material forms trichocysts (spear-like projections) that protrude from the cell on granule discharge (Madeddu et al. (1994); Vayssié et al. (2000)). In Tetrahymena spp., the granule contents take the form of a proteinaceous gel when shed (e.g., similar in consistency to agarose or Sepharose). This gel can surround the cell in a transparent, mucus-like capsule (Turkewitz et al. (2000); Turkewitz (2004)). In Ichthyophthirius multifiliis, i-antigen clustering causes the formation of a similar gel via triggered secretion of cortical mucocysts. Regulated secretion is also known to occur in Paramecium tetraurelia.

Genetic Constructs for Fusion Proteins.

As described herein, a desired heterologous polypeptide can be produced as a fusion protein with one or more mucocyst-targeting sequences. The targeting sequence can be an N-terminal leader or signal sequence from an endogenous mucocyst protein, can be a larger fragment of the mucocyst protein, or can be the entire mucocyst protein or a functional homolog thereof. However, within the mucocysts, the endogenous processing machinery of the granules can be used to cleave away the mucocyst-targeting sequences and thereby generate recombinant proteins that are freely soluble within cortical mucocysts in vivo. After inducing regulated secretion by the mucocysts, the heterologous soluble polypeptide can be isolated from the resulting insoluble extracellular matrix.

The invention provides three distinct forms of genetic construct for achieving this objective. Exemplary constructs are illustrated schematically in FIG. 3, where the desired heterologous soluble polypeptide is indicated as "HSP," the endoplasmic reticulum-targeting polypeptide is indicated as "pre," the mucocyst-targeting polypeptide is indicated as "pro," an endogenous soluble mucocyst-targeted protein is indicated as "SP," and a protease cleavage site is indicated as "CS."

In a first series of embodiments, the fusion protein comprises, N-terminally to C-terminally, (a) a mucocyst-targeting polypeptide of a mucocyst-targeted protein which is cleaved by a protease endogenous to the mucocyst pre-domain; and (b) a desired heterologous soluble polypeptide. When the fusion protein is trafficked to a mucocyst, the mucocyst-targeting polypeptide is proteolytically removed by the endogenous protease, resulting in release of the heterologous soluble polypeptide within the mucocyst. Induction of regulated secretion from the mucocysts results in the discharge of the mucocysts contents, including the heterologous soluble polypeptide. Because the desired heterologous polypeptide is soluble, whereas the extracellular matrix formed by regulated secretion is insoluble, the heterologous polypeptide can be isolated from the matrix by standard techniques.

In some embodiments, the fusion protein further comprises an endoplasmic reticulum-targeting polypeptide N-terminal to said mucocyst-targeting polypeptide. Thus, the structure of the fusion protein can be, N-terminally to C-terminally, (a) an endoplasmic reticulum-targeting polypeptide; (b) a mucocyst-targeting polypeptide of a mucocyst-targeted protein which is cleaved by a protease endogenous to the mucocyst pre-domain; and (c) a desired heterologous soluble polypeptide. The endoplasmic reticulum-targeting polypeptide can be cleaved from the fusion protein in the ER, but this is not required if the endoplasmic reticulum-targeting polypeptide does not interfere with mucocyst-targeting, or the cleavage of the mucocyst-targeting polypeptide from the heterologous polypeptide.

In some embodiments, the mucocyst-targeted protein is a Grl protein, including any of a Grl-1 protein, a Grl-2 protein a Grl-3 protein, a Grl-4 protein, a Grl-5 protein, a Grl-6 protein, a Grl-7 protein, a Grl-8 protein, a Grl-9 protein, and a Grl-10 protein. In these embodiments, the mucocyst-targeting polypeptide is the pro-domain of the Grl protein.

In other embodiments, the mucocyst-targeted protein is a cortical granule protein other than a Grl. A number of endogenous proteins that traffic to the mucocysts but do not associate with the crystalline structure are known (Haddad et al. (2002); Bowman et al. (2005a)). For example, the mucocyst-targeting polypeptide Igr1p (for Induced during Granule Regeneration) can be employed (accession number AAL79508). Alternatively, granule tip proteins can be employed (accession numbers ABC75092; AAZ94627) (Bowman et al. (2005a)). Other proteins with a β/γ crystalline domain have been identified and also can be used in the invention, for example, C-terminal crystallin fold containing protein 3p (accession number ABC75094); C-terminal crystallin fold containing protein 4p (accession number ABC75093); C-terminal crystallin fold containing protein 6p (accession number ABC75099); C-terminal crystallin fold containing protein 7p (accession number ABC75098); C-terminal crystallin fold containing protein 8p (accession number ABC75091); C-terminal crystallin fold containing protein 9p (accession number ABC75097); C-terminal crystallin fold containing protein 10p (accession number ABC75096); C-terminal crystallin fold containing protein 11p (accession number: ABC75090); C-terminal crystallin fold containing protein 12p (accession number ABC75095); C-terminal crystallin fold containing protein 13p (accession number ABC75100).

The endoplasmic reticulum-targeting polypeptide, when present, can be from the same protein as the mucocyst-targeting polypeptide, or it can be heterologous. Indeed, the endoplasmic reticulum-targeting polypeptide can be from any ER-targeted polypeptide, even from different species, as long as it is effective as an ER signal sequence. In some embodiments, the endoplasmic reticulum-targeting polypeptide is the ER signal sequence or pre-domain of a Grl protein or other granule-associated protein. In other embodiments, it can be a heterologous or exogenous sequence, such as the 22 amino acid signal peptide derived from the immobilization antigen variant B protein of *Ichthyophthirius multifiliis*, which has been shown to be functional in *Tetrahymena*.

Figure 3:
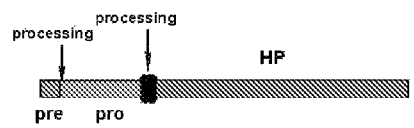
FIG. 3. Fusion protein constructs for expression of soluble recombinant proteins in ciliates through the regulated secretion pathway. In Construct #1, N-terminally to C-terminally, a pre-domain and a pro-domain which result in trafficking to a mucocyst are fused to a heterologous polypeptide (HSP). When the fusion protein is trafficked to a mucocyst, the pre- and pro-domains are proteolytically removed, resulting in release of the heterologous polypeptide (HSP) within the mucocyst. In Construct #2, N-terminally to C-terminally, a pre-domain is fused to the heterologous polypeptide (HSP), which is fused to a protease cleavage site (CS), which is fused to a pro-domain of a mucocyst-targeted protein, which is fused to at least a portion of a mature mucocyst-targeted protein. When the fusion protein is trafficked to a mucocyst, the pre- and pro-domains are proteolytically removed, resulting in release of the fusion of the heterologous polypeptide (HSP), cleavage site (CS) and pro-domain. After regulated secretion, this fusion can be treated with the corresponding protease to release the heterologous polypeptide (HSP), before or after separating it from the extracellular matrix formed by mucocyst discharge. In Construct #3, N-terminally to C-terminally, a pre-domain is fused to a soluble polypeptide (SP) endogenous to the mucocyst, which is fused to a protease cleavage site (CS), which is fused to a heterologous polypeptide (HSP). When the fusion protein is trafficked to a mucocyst, the pre-domain is proteolytically removed, resulting in release of the fusion of the endogenous soluble polypeptide (SP), cleavage site (CS), and heterologous polypeptide (HSP). After regulated secretion, this fusion can be treated with the corresponding protease to release the heterologous polypeptide (HSP), before or after separating it from the extracellular matrix formed by mucocyst discharge.
Figure 3:
Figure 3:
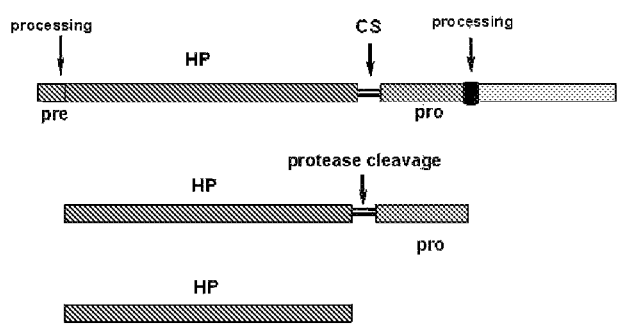
Figure 3:
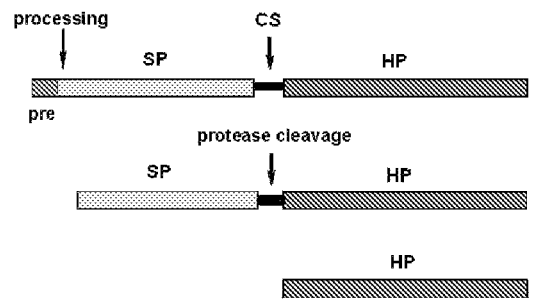

In FIG. 3, Construct #1 illustrates a construct is which, N-terminally to C-terminally, a endoplasmic reticulum-targeting polypeptide (pre) is fused to mucocyst-targeting polypeptide (pro), which is fused to the desired heterologous soluble polypeptide (HSP). When the fusion protein is synthesized, it is trafficked to the ER due to the endoplasmic reticulum-targeting polypeptide, which is typically (but not necessarily) removed by proteolytic processing in the ER. The mucocyst-targeting polypeptide causes the fusion protein (with or without the endoplasmic reticulum-targeting polypeptide) to be trafficked to the secretory granules, where it is cleaved by a sequence-specific protease endogenous to the mucocyst. This results in the release of the heterologous soluble polypeptide (HSP) within the mucocyst.

In a second series of embodiments, a first fusion protein comprises, N-terminally to C-terminally, (a) a desired heterologous soluble polypeptide; and (b) at least a mucocyst-targeting polypeptide of a mucocyst-targeted protein. The first fusion protein may optionally include additional sequences from the mucocyst-targeted protein extending C-terminally from the mucocyst-targeting polypeptide. In such embodiments, when the first fusion protein is trafficked to a mucocyst, the mucocyst-targeting polypeptide is proteolytically cleaved by an endogenous first protease, such that the additional C-terminal sequences are removed, but the heterologous polypeptide remains fused to the mucocyst-targeting polypeptide, thereby producing a second fusion protein. Induction of regulated secretion from the mucocysts results in the discharge of the mucocyst contents, including the second fusion protein.

In some embodiments, the first fusion protein further comprises an endoplasmic reticulum-targeting polypeptide N-terminal to said mucocyst-targeting polypeptide. Thus, the structure of the fusion protein can be, N-terminally to C-terminally, (a) an endoplasmic reticulum-targeting polypeptide; (b) a desired heterologous soluble polypeptide; and (c) at least a mucocyst-targeting polypeptide of a mucocyst-targeted protein. The first fusion protein may optionally include additional sequences from the mucocyst-targeted protein extending C-terminally from the mucocyst-targeting polypeptide, including the entire mucocyst-targeted protein sequence. In such embodiments, when the first fusion protein is trafficked to a mucocyst, the mucocyst-targeting polypeptide is proteolytically cleaved by an endogenous first protease, such that the additional C-terminal sequences are removed, but the heterologous polypeptide remains fused to the mucocyst-targeting polypeptide, thereby producing a second fusion protein. Induction of regulated secretion from the mucocysts results in the discharge of the mucocyst contents, including the second fusion protein. The endoplasmic reticulum-targeting polypeptide can be cleaved from the first fusion protein in the ER, but this is not required if the endoplasmic reticulum-targeting polypeptide does not interfere with mucocyst-targeting, or the cleavage of the mucocyst-targeting polypeptide from the heterologous polypeptide.

In some embodiments, the first fusion protein further comprises a second protease cleavage site between the heterologous polypeptide and the mucocyst-targeting polypeptide of said mucocyst-targeted protein. After inducing regulated secretion of the mucocysts, the extracellular matrix (including the second fusion protein) can be contacted with the second protease to cleave the second cleavage site and separate the mucocyst-targeting polypeptide from the heterologous polypeptide. Alternatively, the second fusion protein can be partially or completely separated from the extracellular matrix, and then the second fusion protein can be contacted with the second protease to cleave the second cleavage site and separate the mucocyst-targeting polypeptide from the heterologous polypeptide. In either case, the desired heterologous polypeptide may then be further purified.

In FIG. 3, Construct #2 illustrates a construct is which, N-terminally to C-terminally, a endoplasmic reticulum-targeting polypeptide (pre) is fused to a desired heterologous soluble polypeptide (HSP), which is fused to a cleavage site (CS), which is fused to a mucocyst-targeting polypeptide (pro), which is fused to additional sequences from the mucocyst-targeted protein (e.g., the entire mature protein sequence). When the fusion protein is synthesized, it is trafficked to the ER due to the endoplasmic reticulum-targeting polypeptide, which is typically (but not necessarily) removed by proteolytic processing in the ER. The mucocyst-targeting polypeptide causes the fusion protein (with or without the endoplasmic reticulum-targeting polypeptide) to be trafficked to the secretory granules, where it is cleaved by a sequence-specific protease endogenous to the mucocyst. This results in the release of a second fusion protein, comprising the heterologous soluble polypeptide (HSP), cleavage site (CS) and mucocyst-targeting polypeptide (pre) within the mucocyst. Reaction of this fusion protein with a protease specific for the cleavage site (CS) results in release of the desired heterologous soluble polypeptide (HSP).

In a third series of embodiments, a first fusion protein comprises, N-terminally to C-terminally, (a) an endogenous soluble mucocyst-targeted polypeptide; (c) a sequence-specific protease cleavage site; and (c) a desired heterologous soluble polypeptide. In these embodiments, the soluble endogenous mucocyst polypeptide is normally trafficked to the mucocysts by virtue of its endogenous ER and mucocyst signal sequences. The heterologous protein is also trafficked to the mucocyst by virtue of its fusion to the soluble endogenous mucocyst polypeptide. Induction of regulated secretion from the mucocysts results in the discharge of the mucocyst contents, including the fusion protein. After inducing regulated secretion of the mucocysts, the extracellular matrix (including the fusion protein) can be contacted with a protease to cleave the cleavage site and separate the endogenous soluble mucocyst protein from the heterologous soluble polypeptide. Alternatively, the fusion protein can be partially or completely separated from the extracellular matrix, and then the fusion protein can be contacted with the protease to cleave the cleavage site and separate the endogenous soluble mucocyst polypeptide from the heterologous soluble polypeptide. In either case, the desired heterologous soluble polypeptide may then be further purified.

In some embodiments, the endogenous soluble mucocyst-targeted protein is an Igr protein. For example, Igr1p is roughly 40-fold more soluble than the Grls and, therefore, can be fused with a desired heterologous soluble polypeptide such that the fusion protein will traffic to the granules and remain soluble as well.

In some embodiments, the fusion protein further comprises an endoplasmic reticulum-targeting polypeptide N-terminal to the endogenous soluble mucocyst-targeted polypeptide. The endoplasmic reticulum-targeting polypeptide, when present, can be from the same protein as the endogenous soluble mucocyst-targeted polypeptide, or it can be heterologous. Indeed, the endoplasmic reticulum-targeting polypeptide can be from any ER-targeted polypeptide, even from different species, as long as it is effective as an ER signal sequence. In some embodiments, the endoplasmic reticulum-targeting polypeptide is the ER signal sequence or pre-domain of a Grl protein or other granule-associated protein. In other embodiments, it can be a heterologous or exogenous sequence, such as the 22 amino acid signal peptide derived from the immobilization antigen variant B protein of *Ichthyophthirius multifiliis*, which has been shown to be functional in *Tetrahymena*. In these embodiments, the endoplasmic reticulum-targeting polypeptide can be cleaved from the fusion protein by endogenous processing in the ER.

In FIG. 3, Construct #3 illustrates a construct is which, N-terminally to C-terminally, an endoplasmic reticulum targeting polypeptide (pre) is fused to a soluble polypeptide (SP) endogenous to the mucocyst, which is fused to a protease cleavage site (CS), which is fused to a heterologous polypeptide (HSP). When the fusion protein is trafficked to a mucocyst, the pre-domain is proteolytically removed, resulting in release of the fusion of the endogenous soluble polypeptide (SP), cleavage site (CS), and heterologous polypeptide (HSP). After regulated secretion, this fusion can be treated with the corresponding protease to release the heterologous polypeptide (HSP), before or after separating it from the extracellular matrix formed by mucocyst discharge.

Genetic constructs encoding such fusion proteins can readily be prepared by one of skill in the art based upon the universal genetic code, and optionally employing the codon preferences characteristic of the ciliate host. See, Larsen et al. (1999); Wuitschick and Karrer (2000); Eisen et al. (2006); and Wuitschick and Karrer (1999).

The genetic constructs can be designed to include a cleavable linker such as protease cleavage site, self-cleaving intein sequence, or flexible linker sequence between the mucocyst targeting sequence(s) and the heterologous polypeptide, and/or may be designed to include additional sequences useful for purification of the fusion protein (e.g., poly-His or epitope tags for affinity or immuno purification).

The sequences encoding the fusion protein can be introduced into the cells on expression plasmids, or can be stably integrated into the protist genome (e.g., by homologous recombination, retroviral insertion). When integrated into the genome, the fusion protein sequences can replace (in whole or in part) the endogenous sequences encoding the corresponding mucocyst protein, or can be inserted at a separate genomic location. Targeting sequences useful for secretion of foreign proteins in *Tetrahymena* spp. are described in (Clark et al. (2001)).

The nucleic acid sequences can be cloned using standard cloning procedures in the art, as described by Sambrook et al., Molecular Cloning: A Laboratory Manual, Second Edition, Cold Springs Laboratory, Cold Springs Harbor, N.Y. (1989). For example, chimeric genes encoding the fusion proteins can be generated by linking coding regions of genes for the heterologous polypeptides to endogenous mucocyst targeting sequences (or mucocyst protein fragments or entire mucocyst proteins) either synthetically (Lin et al. (2002)), or by PCR using serial overlap extension. The resulting constructs can then introduced into standard plasmid DNA vectors (e.g., TOPO, BlueScript, etc.) for amplification in *E. coli* by chemical transformation, electroporation or any other method known in the art.

Ciliates Useful in the Invention

The invention may be practiced with a variety of different ciliates which include secretory granules called mucocysts. Heterologous polypeptides can be targeted to these secretory granules by encoding fusion proteins of the desired heterologous polypeptide and an appropriate targeting sequence. After exposing the ciliate to a secretory stimulus that causes the mucocysts to discharge their contents to the extracellular environment, the heterologous polypeptide can be recovered from the resulting matrix and medium.

The free-living ciliate protists are a large and diverse phylum (Ciliata) whose members display a structural and functional complexity comparable to that of higher metazoa (Fankel (2000); Turkewitz et al. (2002)), and include over 7,000 species with 11 major subdivisions. Tetrahymenids and *Paramecium* belong to the Oligohymenophoreans. Ciliates that include mucocysts useful in the invention include *Tetrahymena* species such as *Tetrahymena thermophila* and *Tetrahymena pyriformis*. *Paramecium* has dense core granules but does not secrete a proteinaceous gel. Both *Tetrahymena thermophila* and *Tetrahymena pyriformis* produce mucocysts, and both secrete a proteinaceous gel.

*Tetrahymena* spp. are amenable to genetic manipulation, can be grown on a large scale and have a doubling time of 1.5-3 hrs. Unlike *T. thermophila*, which has an optimal growth temperature of 35° C., the optimal growth temperature for *T. pyriformis* is lower (maximal growth temperature of 34° C.). Cells reach high-density in a short time on a variety of inexpensive media and can be expanded for growth in bioreactors up to several thousand liters in size (Hellenbroich et al. (1999); de Coninck et al. (2000)). Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

*Tetrahymena* spp. devote a large part of their metabolism to membrane protein production due to the hundreds of cilia that extend from its surface (Williams et al. (1980)). Additionally, *Tetrahymena* spp. lack a cell wall and display high-mannose N-glycan protein modifications that lack branched, immunogenic structures (Taniguchi et al. (1985); Becker and Rusing (2003); Weide et al. (2006)). Glycosylation patterns of secreted proteins in *Tetrahymena* spp. are uniform and consist of high-mannose N-glycan structures comprising $Man_3GlycNac_2$ core N-glycans similar to those which are produced in the endoplasmic reticulum of mammalian cells.

This glycosylation pattern is unlike the glycosylation pattern produced in other microbial systems. For example, such glycosylation is non-existent in bacteria, and is highly branched and immunogenic in fungi.

Vectors

Heterologous nucleic acids can be introduced into the ciliate host on an expression vector that is capable of integrating into the host's genome. For example, expression vectors capable of homologous recombination with a highly expressed gene that is endogenous to the protozoan host, such as a P-tubulin gene are known in the art. Alternatively, a heterologous nucleic acid transformed into a ciliate can be maintained extrachromosomally on an autonomous plasmid.

Expression vectors useful for transforming ciliates in accordance with the methods described herein include but are not limited to replacement vectors, rDNA vectors, and rDNA-based vectors. Replacement vectors accomplish DNA-mediated transformation by replacing or altering endogenous genes using homologous recombination. Integration of the heterologous nucleic acid into the host's genome at the targeted site is accomplished via homologous recombination involving a double crossover event with the vector containing the heterologous nucleic acid. An example of an expression vector useful for genomic incorporation of a heterologous nucleic acid by replacement is one that includes a heterologous coding sequence flanked by portions of the endogenous BTU1 gene of *Tetrahymena thermophila*.

A replacement vector can include a 5' region, followed by a heterologous coding region, followed by a 3' region, wherein at least a portion of each of the 5' and 3' regions is complementary to 5' and 3' regions on an endogenous gene of the host, to allow for genomic integration of the heterologous coding region via homologous recombination. The 5' and 3' regions of the vector can also comprise regulatory elements, such as a promoter and a terminator. The necessary regulatory elements can also be supplied by the endogenous gene into which the heterologous coding region integrates. Suitable regulatory regions include, but are not limited to promoters, termination sequences, signal peptides and proprotein domains involved in the expression and secretion of proteins. For example, such regulatory elements can provide efficient heterologous expression of proteins in *Tetrahymena* spp. under control of promoters and/or terminators which are derived from genes in *Tetrahymena* ssp. Such vectors can comprise naturally occurring promoters and/or terminators from proteins secreted at a high level in *Tetrahymena* ssp. The expression of recombinant polypeptides in *Tetrahymena* spp. can be driven by strong promoters, pre/pro sequences and terminators. In one embodiment, the promoters and/or terminators can be selected from proteins secreted at a high level independent of the cell-cycle in *Tetrahymena* spp. (US Patent Application 2006/0127973; WO2003/078566). Inducible promoters from *Tetrahymena* spp. genes have also been described that allow robust expression of foreign genes. For example, heat-inducible promoters of the heat shock protein family of the ciliate *Tetrahymena* spp. are also suitable for use with the methods described herein. Suitable heat shock promoters from *Tetrahymena* spp. are known in the art (see WO2007/006812).

Methods for creating mitotically stable *Tetrahymena* spp. transformants, for example, by integration of a heterologous gene by homologous DNA recombination, are known in the art. Methods for generating *Tetrahymena* spp. having targeted gene knockouts by homologous DNA recombination are also known in the art (Bruns and Cassidy-Hanley (2000); Hai et al. (2000) 514-531; Gaertig et al. (1999); Cassidy-Hanley et al. (1997)). The somatic macronucleus or the generative micronucleus can be transformed in alternation. For example, sterile transformants, which may provide improved safety parameters, can be obtained with macronucleus transformation.

Expression vectors can also be maintained extrachromosomally in the ciliates. An expression vector maintained as an extrachromosomal element can be a rDNA-based vector containing an ori from *Tetrahymena* spp. rDNA, which is known to support extrachromosomal replication. Such a vector can further comprise a 5' regulatory region from an endogenous *Tetrahymena* spp. gene containing a promoter region operably linked to the heterologous coding region and, optionally, a 3' regulatory region from the same or a different *Tetrahymena* spp. gene. For example, regulatory regions from ciliate genes in such vectors can include, but are not limited to, regulatory regions from genes such as HHFI, rp129, BTU1, BTU2, SerH3, and actin.

There are a number of suitable vectors suitable for transformation of ciliates known in the art. For example, *Tetrahymena* spp. can be transformed with an rDNA vector (Tondravi and Yao (1986); Yu and Blackburn (1989)). The shuttle vector pXS76 allows insertion of transgenes downstream of a cadmium-inducible promoter from the MTT1 metallothionein gene of *T. thermophila* via homologous recombination and selection in paromomycin. Alternatively, inserts can be introduced into high copy number ribosomal DNA vectors (such as pD5H8) under control of the cadmium-inducible MTT1 promoter. The pD5H8 vector takes advantage of a biological feature of *Tetrahymena* spp. in which the ribosomal cistrons become amplified to extraordinarily high copy numbers following conjugation. An rDNA-based vector can be a circular vector that contains a 5' non-translated sequence comprising two or more ori sequences from *Tetrahymena* spp. rDNA. A nucleic acid fragment containing a heterologous coding region, for example a selectable marker or transgene, can also be added to the vector. The vector can further comprise a 5' untranslated region of a *Tetrahymena* spp. gene and a 3' untranslated region of a *Tetrahymena* spp. gene, inserted upstream and downstream of the selectable marker and/or the transgene. Methods for transformation, along with robust, inducible promoters for driving high-level gene expression have recently been described for this system (Bruns and Cassidy-Hanley (2000); Gaertig and Kapler (2000); Shang et al. (2002); Boldrin et al. (2006)).

Figure 5:
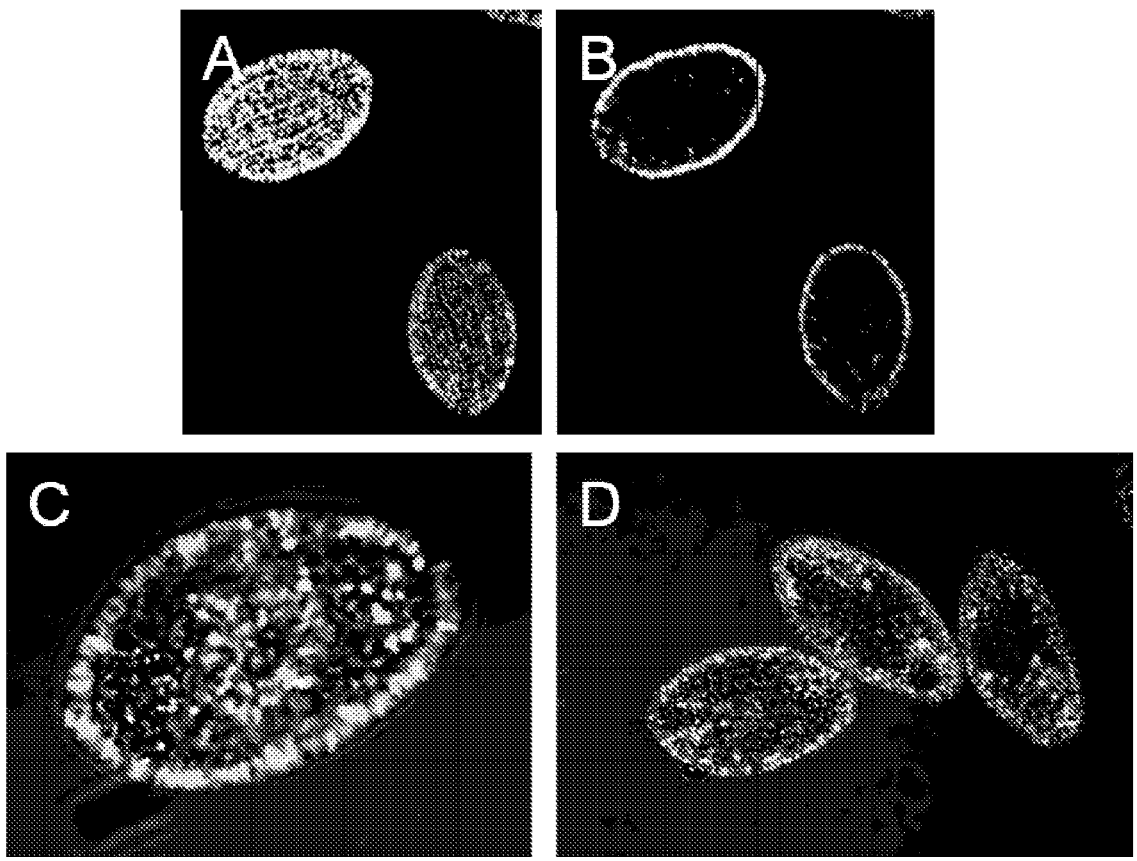

Sequence variations within the origins of replication of rDNA from wild-type B- and C3-strains of *T. thermophila* convey a replicative advantage to the C3-form in B/C3 heterozygotes. Although both B- and C3-forms of rDNA are initially present in the macronucleus in approximately equal amounts, within 30 fissions only the C3 variant remains (Pan et al. (1982); Orias et al. (1988)). pIC19-based shuttle vectors containing the C3 origin of replication have been used as high-copy number vectors for the delivery of foreign DNA to *Tetrahymena* spp. (Yu and Blackburn (1989)) (FIG. 5).

Although such vectors can become unstable and be lost within about 50 to about 80 generations, micronuclear versions of the C3 rDNA is accurately processed (to form a palindrome) following introduction into *T. thermophila* B cell lines. The micronuclear version is maintained as a stable linear chromosome over many generations (Bruns et al. (1985)). Functional transgenes can be inserted into the 3'-nontranscribed spacer (3'-NTS) of such vectors with no effect on rDNA processing. Within 6-10 generations, recombinant molecules can comprise 50-100% of the total rDNA complement, with as many as 18,000 copies of the transgene per cell (Blomberg et al. (1997)). The use of this approach enables an increase in the number of cloned genes in transformed cell lines by orders of magnitude and leads to increased expression at the protein level. For example, the use of rDNA-based vectors in combination with the MTT1 promoter can be used to drive expression of the endogenous granule lattice protein Grl1p to approximately 20% of total cell protein (Lin et al. (2002)). Similarly, pD5H8 rDNA-based vectors (Blomberg et al. (1997)) can be used to boost expression of proteins by at least 3-10 fold compared with transformants in which respective transgenes are integrated at somatic gene loci. Other vectors suitable for use with the methods described here include vectors comprising a ribosomal DNA sequence. Such vectors can replicate at high copy numbers and can be used to deliver a heterologous DNA sequence to *Tetrahymena* spp. for purposes of RNA expression.

Transformation.

Genes can be introduced into ciliates using established protocols or any method known to one skilled in the art. Transformation of ciliates can be achieved by microinjection (Tondravi and Yao (1986)), electroporation (Gaertig and Gorovsky (1992)), or biolistically (Cassidy-Hanley et al. (1997)).

Thus, in some embodiments, ciliate cells can be transformed with a chimeric gene by particle bombardment (also known as biolistic transformation) (Cassidy-Hanley et al. (1997)). Particle bombardment transformation can be achieved by several ways. For example, inert or biologically active particles can be propelled at cells under conditions effective to penetrate the outer surface of the cell and to be incorporated within the interior thereof. When inert particles are utilized, the vector can be introduced into the cell by coating the particles with the vector containing the chimeric gene. Alternatively, the target cell can be surrounded by the vector so that the vector is carried into the cell by the wake of the particle. Other variations of particle bombardment, now known or hereafter developed, can also be used.

Microcarrier bombardment can also be used to transform ciliate cells by means of DNA-loaded gold particles (U.S. Pat. No. 6,087,124; European Pat. EP 847 444; WO 1998/001572). In this approach, microcarrier bombardment with DNA-coated gold is used as a means of introducing foreign genes into ciliates. In one embodiment, microcarrier bombardment can be used to transform ciliates and introduce genes into the (germline) micronucleus Methods for selection of transformed cells harboring foreign genes are known in the art. For example, the vector can further comprise a selectable cassette marker to permit selection for transformed cells (e.g., a neo 2 cassette) (Gaertig et al. (1994)). Selection of transformants can be achieved by growing the cultured ciliates in a medium which allows only the transformants to survive. Suitable selection agents include antibiotics which will kill most all non-transformants but allow transformants (which also possess an antibiotic resistance gene) to survive. A number of antibiotic-resistance markers are known in the art. Any known antibiotic-resistance marker can be used to transform and select transformed host cells in accordance with the present invention. For example, selection of the transformants can be performed by means of a resistance marker such as a point mutation in the 17s rDNA, which confers resistance to paromomycin, can allow for selection of rDNA transformants (Spangler and Blackburn (1985); Bruns et al. (1985)). Other methods include the use of a mutant cell line that allows targeting of genes to the beta tubulin-1 locus of *T. thermophila* by homologous recombination, and allows efficient selection of transformed cell lines by growth in the microtubule-stabilizing agent (taxol) (U.S. Pat. No. 6,846,481). Another method for selection of transformed cells harboring foreign genes is to insert full length coding regions into the pD5HA vector (Cowan et al. (2005)). In this method, transcription is driven by the inducible MTT1 promoter. Once cells have been transformed with the pD5HA vector selection of positive transformants is determined by paromomycin resistance (i.e., cell growth in media containing the drug). Presence of the transgene is then verified by PCR and then induced with cadmium chloride to over-express the recombinant gene product.

Many other selectable marker systems are known in the art. Selectable marker genes that confer resistance or tolerance to a normally toxic selection agent allow only successfully transfected cells to survive in the presence of the selection agent, and are referred to as positive selectable markers. Examples of positive selectable marker genes and their corresponding selection agents are: aminoglycoside phosphotransferase (APH) and G418; dihydrofolate reductase (DHFR) and methotrexate (Mtx); hygromycin-B-phosphotransferase (HPH) and hygromycin-B; xanthine-guanine phosphoribosyltransferase (XGPRT) and mycophenolic acid; and adenosine deaminase (ADA) and 9-β-D-xylofuranosyl adenine (Xyl-A). In another example of a positive selectable marker system, thymidine kinase (TK) and aminopterin (included, e.g., in hypoxanthine-aminopterin-thymidine (HAT) medium) can be used in cells that are initially thymidine kinase deficient (tk⁻). The aminopterin will normally kill tk⁻ cells and, therefore, only successful TK transfectants will survive. Selectable marker genes that confer sensitivity or susceptibility to a normally non-toxic selection agent cause only successfully transfected cells to die in the presence of the selection agent, and are referred to as negative selectable markers. An example of a negative selectable marker system is thymidine kinase (TK) and gancyclovir. Phenotypic selectable marker genes permit selection based upon morphological or biochemical traits rather than cell death or survival. In some cases, the phenotypic marker is detectable only in the presence of an additional selection agent. An example of a phenotypic selectable marker system is β-galactosidase (lacZ) and X-gal.

Isolation of Desired Polypeptides from the Mucocyst Matrix.

In one aspect, the invention provides methods for protein purification from the extracellular matrix formed by the discharge of mucocysts. Because heterologous polypeptides targeted to the mucocyst compartment will be associated within the matrix, the invention provides matrix-based purification strategies. Advantageously, the matrix can be used for rapid purification of recombinant polypeptides associated with it.

Proteins within the gel matrix can be separated from cellular constituents by low-speed centrifugation (See Turkewitz et al. (2000)). Any other method known in the art suitable for separating intact cells, from the discharged material, including, but not limited to filtration harvesting using an appropriately selected mesh, can also be used in conjunction with the methods described herein. After isolation of the matrix, the desired heterologous polypeptide can be liberated from the secreted matrix gel. Methods for liberation of the protein can include chemical methods (e.g., high salt concentrations) and/or enzymatic methods (e.g., site-specific proteases).

Proteins can also be isolated in intact secretory granules. For example, the use of an exocytosis-defective mutant, MN173, of *T. thermophila* where granules accumulate in the cytoplasm has been described for such purposes (Melia et al. (1998)).

Heterologous Polypeptides.

Suitable heterologous polypeptides for use with these methods include, but are not limited to, antibodies, antibody fragments, cytokines, growth factors, protein kinases, proteases, protein hormones or any fragment thereof. Similarly, the methods described herein are suitable for the production of specialty proteins. The use of such specialty proteins can include, but is not limited to, prototype vaccines for animal model studies, structural studies, or as therapeutic proteins. For example, quantities of antigens can be produced according to the methods described herein.

Mucus as a Vaccine Delivery Vehicle

In the case where antigens are produced according the methods described herein, the mucus can serve as a vehicle for the delivery of subunit vaccine antigens to humans and other vertebrates in a highly potent form. In these embodiments, the antigens are not purified from the mucus matrix. Rather, the mucus containing one or more heterologous antigens can serve as the vaccine. The potency of this material can be attributed to several unique properties of the mucus. First, the material stored by dense core granules forms a crystalline array. The crystalline nature of this material is retained following mucocyst discharge as an expanded (hydrated) proteinaceous gel. Proteins within the mucus are therefore present in a highly repetitive form with a molecular spacing that is advantageous for cross-linking the immunoglobulin receptor on B-cells. Lateral clustering of Ig receptors on the B-cell membrane provides a strong signal for these cells to divide and produce large quantities of antibodies. In this way, the mucus can induce B-cell responses to co-administered antigens without the need for T-cell help. Although it derives from an entirely different source, the material comprising the mucus has similar properties to virus-like particles but can be made in large volumes at very low cost.

In addition to enhancing antibody production by B-cells, the mucus is a particulate substance, and as such, can be avidly phagocytosed by professional antigen-presenting cells that are critical to the stimulation of cell-mediated immunity by T-lymphocytes.

Mucus can be engineered to contain more than a single antigen in the same vaccine formulation by co-expressing multiple fusion proteins comprising different antigens in one ciliate cell. Such formulations would be useful in the manufacture of multivalent vaccines against different strains of the same pathogen, or combination vaccines that target completely unrelated pathogens.

In addition to antigens, the mucus can also be engineered to contain immunostimulatory substances that will enhance the immune response to co-administered antigens. Professional antigen-presenting cells are equipped with pattern-recognition receptors that scan the environment for pathogen-associated molecules, and other so-called "danger" signals that alert them to the presence of a threat. The danger signals include proteins, carbohydrates, lipids, nucleic acids and various small molecules such as uric acid. Once recognized by a pattern recognition receptor, these molecules convey activating signals to professional antigen presenting cells that enhance their ability to promote T-cell development and proliferation. Many such immunostimulatory substances are known in the art. Examples include, but are not limited to, bacterial flagellin, pathogen-associated glycolipid anchors, double-stranded RNA, bacterial DNA, CpG oligonucleotides, profilin, complement component C3d, heat shock proteins, high mobility group proteins, and others. In the case where these substances are proteins, they can be co-expressed with immunogenic peptides comprising vaccine antigens and co-administered with the mucus as highly potent vaccines.

Immunostimulatory substances can also be incorporated into mucus that contains heterologous vaccine antigen(s) by non-specific adsorption, or by specific binding to a fusion protein that is a receptor for the immunostimulatory substances and is co-expressed with the vaccine antigen(s) in the mucus.

The following examples illustrate some preferred modes of practicing the present invention, but are not intended to limit the scope of the claimed invention. Alternative materials and methods may be utilized to obtain similar results.

EXAMPLES

Example 1

Targeting Heterologous Proteins to Mucocysts

Figure 4:
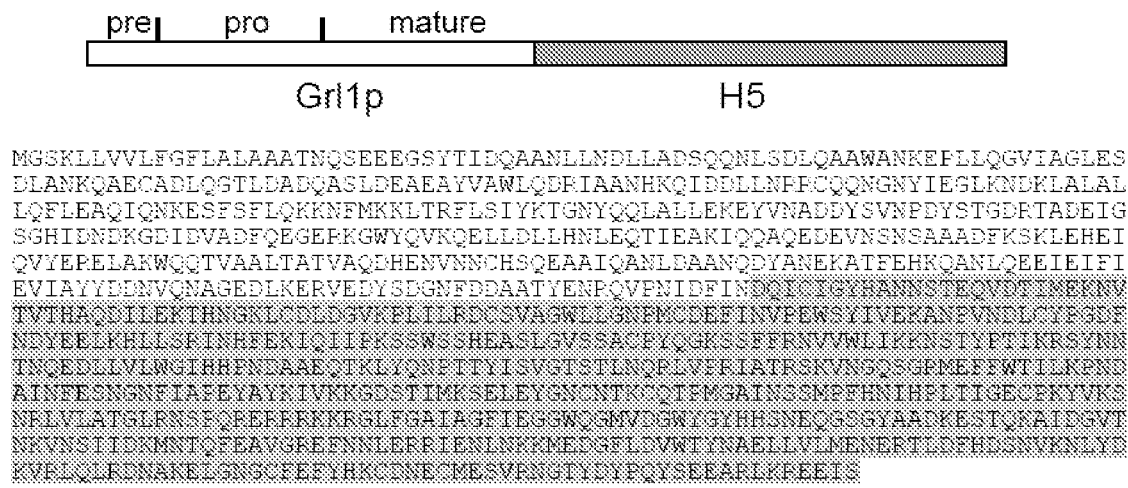
FIG. 4. Chimeric Grl1p:H5 and Grl1p:scFv gene products. Panel (A) shows a diagram of the fusion protein between the full-length, Grl1p, granule lattice protein from *T. thermophila* and the coding sequence of the influenza virus H5 the full-length coding sequence for Grl1p from *T. thermophila*. The resulting chimeric genes (Grl1p:H5 and Grl1p:scFab) were introduced into the cadmium-responsive MTT1 locus of *T. thermophila* and induced with 2 μg/ml CdCl$_2$. Cells were then fixed and permeabilized with detergent in order to localize the recombinant gene products by immunofluorescence microscopy. For H5 localization, permeabilized cells were incubated with a 1:50 dilution of the mouse mAb 5C5, which is specific for the H5 hemagglutinin, followed by a 1:200 dilution of rhodamine-tagged goat anti-mouse IgG. Panel (A) shows a stacked Z-series. Panel (B) shows a single Z-section through the cells. Note the obvious punctate staining at the cell periphery where cortical secretory granules are located. For localization of the scFab, cells were incubated in a 1:300 dilution of the mouse mAb against the HA epitope, followed by 1:500 dilution of rhodamine-tagged goat anti-mouse IgG. A similar pattern of staining was seen as with the Grl1p:H5 fusions. Panel (C) shows confocal Z-section of a single cell, while panel (D) shows three cells at a slightly lower magnification.
Figure 4:
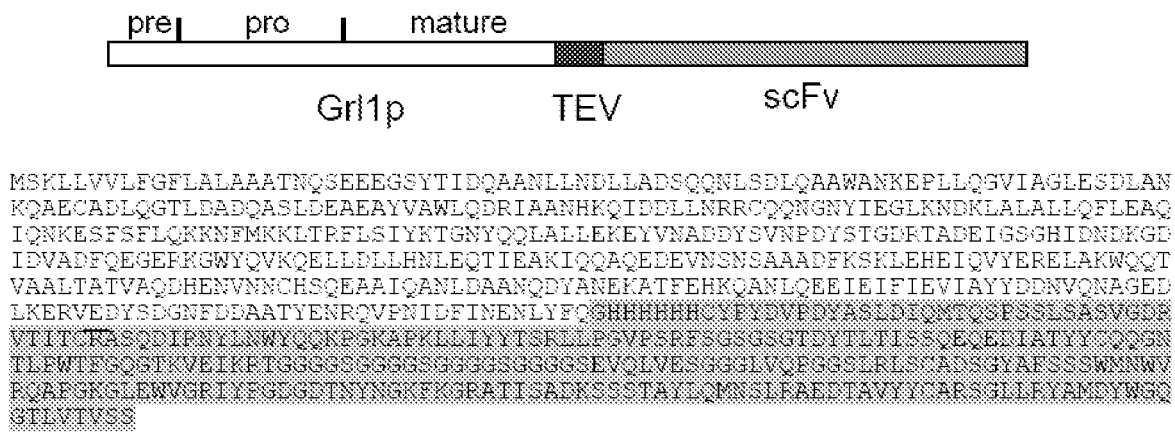

The amino acid sequence for green fluorescent protein (GFP) can be linked to the granule lattice proteins of *Tetrahymena* spp., namely (e.g., Grl1p), and the resulting Grl1p:GFP chimera traffics to mucocysts in vivo (Bowman et al (2005), *Traffic* 6:303-323). This demonstrated that the targeting sequences of the granule-lattice proteins can be used to localize heterologous polypeptides to mucocysts. This result was confirmed using a vaccine antigen from avian influenza virus and a single-chain antibody fragment against anthrax PA toxin linked to the C-terminus of Grl1p (FIGS. 4-6). As shown herein, (1) such proteins localize to cortical secretory granules, (2) mucocysts that contain such proteins can be functional and discharge their contents, (3) proteins linked to Grl 1p associate with the mucocyst gel following granule discharge and (4) proteins of interest could be released from the mucocyst gel and recovered in a purified form

Example 2

Targeting and Purification of Recombinant Proteins

Figure 1:
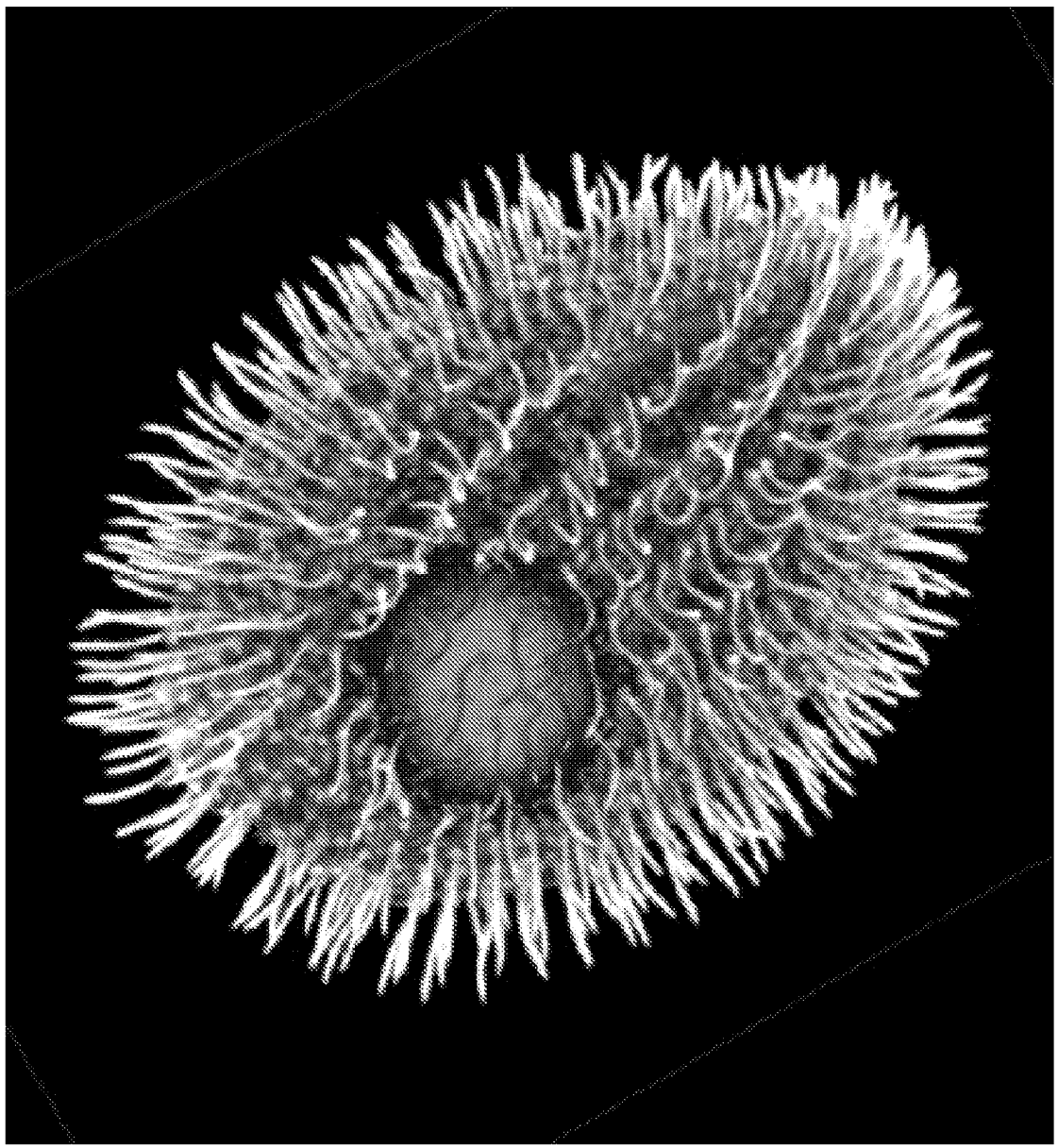
FIG. 1. Immunofluorescence light micrograph of *T. thermophila*. The cell is stained with anti-tubulin antibodies to visualize the cilia (hair-like projections at the cell periphery) and DAPI to visualize the nucleus (round body at the lower center). The cell dimensions are ~20×50 µM.

*Tetrahymena thermophila* cells can be used as a platform for overexpression of recombinant polypeptides (FIG. 1). *Tetrahymena* spp. cells grow rapidly to high cell density in inexpensive media. *Tetrahymena* spp. also accumulates endogenous protein in cortical secretory granules, or mucocysts, which discharge their contents in a stimulus-dependent fashion in response to a variety of secretogogues. Proteins stored in mucocysts can self-associate and form an insoluble proteinaceous gel when released from cells (FIG. 2). In one aspect, the methods describe herein relate to the finding that this gel can serve as a matrix for the purification of recombinant polypeptides. In one embodiment, the gel provides a means for separating recombinant gene products from the bulk of contaminating cellular proteins.

*Tetrahymena* spp., like other ciliates, has two, functionally distinct nuclei: a polyploid macronucleus that is transcriptionally active, and a diploid micronucleus that is transcriptionally silent and functions only in sexual conjugation. When cells mate, the old macronucleus degenerates and is replaced by a new macronucleus that develops from one of several post-zygotic micronuclei. Macronuclear development is accompanied by a spectacular increase in ribosomal DNA (rDNA) copy number. The two rDNA alleles within the micronuclear genome become excised from chromosome 1, and form unique 21 kb palindromic chromosomes that become amplified roughly 9,000 fold.

Granule lattice proteins are made as preproteins, with their pre-domains acting as standard signal sequences for ER translocation, and their pro-domains directing vesicle trafficking and maturation within the granules. Propeptides are cleaved from Grls through the action of, as yet unidentified, proteolytic processing enzymes. Thus, in one embodiment, the methods described herein provide a method for purification of a heterologous polypeptide covalently linked to one of more mucocyst proteins secreted into the insoluble gel of a *Tetrahymena* spp. cell. Genetic engineering techniques can be used to covalently link heterologous polypeptides of interest to one or more mucocyst proteins. In one embodiment, the mucocyst protein linked to the heterologous polypeptide can be a protein normally secreted into the gel, such as a granule lattice protein (Grls). For example, a heterologous polypeptide linked C-terminally to a newly synthesized Grl will traffic to mucocysts and be processed into mature Grl linked N-terminally to the heterologous polypeptide partner.

Such heterologous polypeptides can be harvested upon secretion from the cell. In one embodiment, heterologous polypeptides, such as linked heterologous polypeptides described herein, will associate with the insoluble mucus via their Grl partners upon secretion from the cell and can be harvested by low speed centrifugation or filtration. For example, such methods can be used for the production and harvesting of single-chain antibody fragments against anthrax PA toxin, and the H5 hemagglutinin of avian influenza virus (FIGS. 4-6).

The methods described herein also provide for the introduction of one or more site-specific protease cleavage sites or self-cleaving inteins between the mature Grl sequence and the heterologous polypeptide of interest. When such a site-specific protease cleavage site is introduced between the mature Grl sequence and the heterologous polypeptide of interest, the heterologous polypeptide can be separated from the matrix by treatment of the harvested gel with a site-specific protease.

Similarly, when a self-cleaving intein is introduced between the mature Grl sequence and the heterologous polypeptide of interest, the heterologous polypeptide can be separated from the matrix by the introduction of conditions that lead to intein cleavage (e.g., treatment with disulfide reducing agents) (FIG. 7). Such treatments separate heterologous polypeptides of interest from the gel matrix and permit isolation of the desired proteins in a highly purified form following low-speed centrifugation and/or filtration to remove the insoluble components of the gel.

Example 3

Mucocyst Targeting

Chimeric genes were synthesized by GenScript Inc (Piscataway, N.J.). Restriction enzymes were purchased from New England Biolabs. *Tetrahymena* cells were cultured in NEFF medium (0.25% proteose peptone, 0.25% yeast extract, 0.55% glucose, 33 μM $FeCl_3$) supplemented, when required, with paromomycin at a final concentration of 100 μg/ml. All medium components were acquired from VWR. For Biolistic transformations DNAdel™ S550d gold carrier particle suspension was purchased from Seashell Technology and filter paper from Whatman. Western analysis was carried out with a conformation specific neutralizing mouse monoclonal antibody, 5C5. Anti-mouse horse-radish peroxidase (HRP)-conjugated secondary antibodies was purchased from Bio-Rad. Insect cell-derived H5N1 hemagglutinin was obtained from Protein Sciences. For induction of regulated secretion Dibucaine was purchased from Sigma-Aldrich and Protease Inhibitor Cocktail from Roche.

Expression construct design, synthesis and cloning: The fusion construct was comprised of a truncated form of the avian influenza H5N1 hemagglutinin lacking the transmembrane domain (H5ΔTMD) fused in-frame to the *Tetrahymena* Grl1 protein comprising the Pro domain and mature Grl1 amino acid sequence (H5ΔTMD$^{ProGrl1}$, FIG. 8 Panel A). The genes encoding H5ΔTMD$^{ProGrl1}$ was chemically synthesized with flanking BamHI and SacI restriction sites and subsequently cloned into the same restriction sites of a *Tetrahymena* somatic expression vector, pXS76. Transcription of the transgene is under control of a robust cadmium-inducible promoter from the metallothionein-1 (MTT1) gene of *Tetrahymena thermophila*. The expression construct comprising MTT1 promoter, transgene, MTT1 terminator and a neomycin resistance cassette were transferred, en masse, as a NotI fragment into a high-copy rDNA vector, pD5H8 and introduced into conjugating *Tetrahymena thermophila* strains by biolistic transformation.

Generation of expression strains: B2086 and CU428 *T. thermophila* strains were grown in modified NEFF medium (0.25% proteose peptone, 0.25% yeast extract, 0.55% glucose, 33 mM $FeCl_3$) at 30° C. One hundred ml of each logarithmically growing culture was centrifuged at 1,100×g for 2 minutes in oil centrifuge tubes, washed in 10 mM Tris pH 7.4 and resuspended in fresh 10 mM Tris pH 7.4 (starvation medium) at a concentration of 200,000-250,000 cells/ml. Cells were incubated for 9-18 hours at 30° C. After starvation, B2086 and CU428 cell cultures were counted and cell concentration was readjusted to 200,000 cells/ml. To induce conjugation, 100 ml of each strain were mixed together in a 4 L flask. Four transformations were performed between 9.5 and 10.5 hours post-mixing using a Biolistic PDS-1000/He Particle Delivery System (BIO-RAD). For each transformation, 20 μl of DNAdel™ S550d gold carrier particle suspension were coated with 4 μg of DNA construct according to manufacturer's instructions. Fifty ml of conjugating cells were concentrated to ~1 ml by centrifugation at 1,100×g in oil centrifuge tubes for 2 minutes. Cells were spread on a round 90 mm hardened paper filter (Whatman, Cat. #1450-090) pre-wet with 1.5 ml 10 mM Tris pH 7.4 inside a Petri dish. After the bombardment, the filter with the cells was transferred into a 500 ml flask containing 50 ml NEFF medium. The flasks were incubated on a slow shaker for ~20 hours at 30° C. At 30 hours post-mixing, 25 ml NEFF medium containing 300 μg/ml paromomycin was added to the 50 ml of cell culture (final paromomycin concentration, 100 μg/ml). Cells were aliquoted into 96 well microplates (150 μl per well). After 3-4 days, the microplates were examined and 5 μl from each of the wells containing paromomycin-resistant cells were transferred into 150 μl NEFF medium containing 100 μg/ml paromomycin on a master 96 well microplate.

Western analysis: To evaluate H5ΔTMD$^{ProGrl1}$ expression, cultures were grown to ~5×10$^5$ cells/ml and induced for 12 hr with 1 μg/ml of $CdCl_2$. Cells were then harvested and lysed in SDS sample buffer in the absence of reducing agents. Proteins were resolved by SDS-PAGE and transferred to nitrocellulose membranes before Western blotting. Blots were probed with the neutralizing mouse monoclonal antibody, 5C5. This antibody recognizes conformational epitopes on H5 that are destroyed by treatment with disulfide reducing agents. Following incubation in primary antibody, blots were probed with secondary goat anti-mouse IgG coupled to HRP for visualization.

Induction of regulated secretion: Expression strains were grown to a cell density of 5×10$^5$ cells/ml prior to induction with 1.5 μg/ml $CdCl_2$. Cells were harvested 16 h post-induction by centrifugation at 2000×g for 5 minutes. The cell pellet was re-suspended in Buffer A (40 mM Hepes, 1 mM $CaCl_2$) followed by the addition of Dibucaine to a final concentration of 2 mM to induce mucocyst release. An equal volume of ice-cold Buffer A containing 2× protease inhibitor cocktail (PIC) was added and then the mixture was centrifuged at 5000×g for 2 minutes to separate supernatant, mucus and cell pellet layers. The mucus layer was harvested and re-suspended in 10 volumes of Buffer A containing 1× PIC and centrifuged once more at 5000×g for 2 minutes.

Immunofluorescence: Cells were induced to express the chimeric fusion gene, fixed and the recombinant H5ΔTMD$^{ProGrl1}$ localized by confocal microscopy. Immunofluorescence staining was carried out with a 1:50 dilution of mouse anti-hemagglutinin mAb (5C5) followed by rhodamine-tagged goat anti-mouse IgG.

Results. Expression of H5ΔTMD$^{ProGrl1}$ in *Tetrahymena* was examined by immunofluorescence and Western analysis in both whole cell lysates and harvested mucus as described herein. FIG. 8 (Panel B) shows that H5ΔTMD$^{ProGrl1}$ is targeted to cortical secretory granules (mucocysts) as evidenced by the punctate staining pattern at the cell periphery. Additionally, FIG. 8 (Panel C) shows that H5ΔTMD$^{ProGrl1}$ is expressed and resolved at a molecular weight >148 kDa indicating the formation of higher order structures of the fusion protein. Such higher order structures are likely a consequence of the H5ΔTMD fusion partner since H5N1 hemagglutinin is known to trimerize. H5ΔTMD$^{ProGrl1}$ is recovered in mucus following induced release of mucocyst contents (FIG. 8, Panel C).

Example 4

Mucocyst Targeting

Materials were as described for Example 3

Methods. Expression construct design, synthesis and cloning: The fusion construct was comprised of a truncated form of the avian influenza H5N1 hemagglutinin lacking the transmembrane domain (H5ΔTMD) fused in-frame to the PrePro domain of *Tetrahymena* Grl1 (H5ΔTMD$^{PrePro}$, FIG. 9 Panel A). Generation of expression constructs was carried out as described for Example 3. Generation of expression strains, Western analysis, induction of regulated secretion and immunofluorescence was carried out as described in Example 3.

Results. Expression of H5ΔTMD$^{PrePro}$ in *Tetrahymena* was examined by immunofluorescence and Western analysis in both whole cell lysates and harvested mucus as described herein. FIG. 9 (Panel B) shows that H5ΔTMD$^{PrePro}$ is targeted to cortical secretory granules (mucocysts) as evidenced by the punctate staining pattern at the cell periphery. Additionally, FIG. 9 (Panel C) shows that H5ΔTMD$^{PrePro}$ is expressed and resolved at a molecular weight >148 kDa indicating the formation of higher order structures of the fusion protein. Such higher order structures are likely a consequence of the H5ΔTMD fusion partner since H5N1 hemagglutinin is known to trimerize. H5ΔTMD$^{PrePro}$ is recovered in mucus following induced release of mucocyst contents (FIG. 9, Panel C).

Example 5

Mucocyst Targeting

Materials. Materials were as described for Example 3

Expression construct design, synthesis and cloning: The fusion construct was comprised of the *Tetrahymena* Igr1 gene fused in-frame to a truncated form of the avian influenza H5N1 hemagglutinin lacking the transmembrane domain (H5ΔTMD$^{Igr1}$, FIG. 10 Panel A). Generation of expression constructs was carried out as described for Example 3. Generation of expression strains, Western analysis, induction of regulated secretion and immunofluorescence was carried out as described in Example 3.

Results. Expression of H5ΔTMD$^{Igr1}$ in *Tetrahymena* was examined by immunofluorescence and Western analysis in both whole cell lysates and harvested mucus as described herein. FIG. 10 (Panel B) shows that H5ΔTMD$^{Igr1}$ is targeted to cortical secretory granules (mucocysts) as evidenced by the punctate staining pattern at the cell periphery. Additionally, FIG. 10 (Panel C) shows that H5ΔTMD$^{Igr1}$ is expressed and is recovered in mucus following induced release of mucocyst contents.

Example 6

Mucocyst Targeting

Materials were as described for Example 3 except that rabbit polyclonal anti-EPO antibody was purchased from Santa Cruz Biotech and HRP conjugated Goat anti-rabbit secondary antibody from Bio-Rad.

Expression construct design, synthesis and cloning: The fusion construct was comprised of the amino acid sequence of feline EPO fused in-frame to the H5N1 hemagglutinin signal peptide at the amino-terminus and to the *Tetrahymena* Grl1 protein comprising the Pro domain and mature Grl1 amino acid sequence at it's carboxy-terminus (EPO$^{ProGrl1}$, FIG. 11 Panel A). Generation of expression constructs was carried out as described for Example 3. Generation of expression strains and induction of regulated secretion was carried out as described in Example 3. Western analysis was carried out using an anti-EPO primary antibody and an anti-rabbit HRP conjugated secondary antibody Results Expression of EPO$^{ProGrl1}$ in *Tetrahymena* was examined by Western analysis in both whole cell lysates and harvested mucus as described herein. FIG. 11 (Panel B) shows that EPO$^{ProGrl1}$ is expressed and is recovered in mucus following induced release of mucocyst contents.

Example 7

Mucocyst Targeting

Materials. Materials were as described for Example 3 except HRP conjugated anti-HA antibody was purchased from Roche.

Expression construct design, synthesis and cloning: The fusion construct was comprised of the *Tetrahymena* Grl1 gene fused in-frame to the gene encoding a single chain antibody fragment (anti-anthrax PA toxin). Separating the Grl1 and scFv genes is DNA encoding, 5' to 3', a TEV protease site, a 6× His tag and a HA peptide epitope (scFv$^{Grl1}$, FIG. 12 Panel A). Generation of expression constructs was carried out as described for Example 3. Generation of expression strains, Western analysis, induction of regulated secretion and immunofluorescence was carried out as described in Example 3 except that anti-HA antibodies were used to carry out Western and immunofluorescence analysis.

Results. Expression of scFv$^{Grl1}$ in *Tetrahymena* was examined by immunofluorescence and Western analysis in both whole cell lysates and harvested mucus as described herein. FIG. 12 (Panel B) shows that scFv$^{Grl1}$ is targeted to cortical secretory granules (mucocysts) as evidenced by the punctate staining pattern at the cell periphery. Additionally, FIG. 12 (Panel C) shows that scFv$^{Grl1}$ is expressed and is recovered in mucus following induced release of mucocyst contents.

Example 8

Mucocyst Targeting

Materials. Materials were as described for Example 3 except HRP conjugated anti-HA antibody was purchased from Roche.

Expression construct design, synthesis and cloning: The fusion construct was comprised of the *Tetrahymena* Grl4 gene fused in-frame to the gene encoding a fragment (amino acids 159-426) of the malarial pfs48/45 antigen. Immediately downstream of the pfs48/45 sequence is a 6× His tag followed by the carboxy-terminal domain (amino acids 371-441) of the immobilization antigen variant B protein of *Ichthyophthirius multifiliis*. At the carboxy-terminus of the fusion construct is a HA epitope tag (FIG. 13 Panel A, pfs48/45$^{Grl4}$). Generation of expression constructs was carried out as described for Example 3. Generation of expression strains, Western analysis, induction of regulated secretion and immunofluorescence was carried out as described in Example 3 except that Western and immunofluorescence analysis was carried out with an anti-HA antibody.

Results. Expression of pfs48/45$^{Grl4}$ in *Tetrahymena* was examined by immunofluorescence and Western analysis in both whole cell lysates and harvested mucus as described herein. FIG. 13 (Panel B) shows that pfs48/45$^{Grl4}$ is targeted to cortical secretory granules (mucocysts) as evidenced by the punctate staining pattern at the cell periphery. Additionally, FIG. 13 (Panel C) shows that pfs48/45$^{Grl4}$ is expressed and is recovered in mucus following induced release of mucocyst contents. A majority of fusion protein in the mucus resolves at approximately 50 kDa indicating that the prepro-domain of Grl4 has been processed in vivo.

Example 9

Mucocyst Targeting

Materials were as described for Example 3 except HRP conjugated anti-HA antibody was purchased from Roche.

Expression construct design, synthesis and cloning: The fusion construct was comprised of the PrePro domain of the *Tetrahymena* Grl1 gene fused in-frame to the gene encoding a fragment (amino acids 159-426) of the malarial pfs48/45 antigen. Immediately downstream of the pfs48/45 sequence is a 6× His tag followed by the carboxy-terminal domain (amino acids 371-441) of the immobilization antigen variant B protein of *Ichthyophthirius multifiliis*. At the carboxy-terminus of the fusion construct is a HA epitope tag (FIG. 14 Panel A,)pfs48/45$^{PrePro}$. Generation of expression constructs was carried out as described for Example 3. Generation of expression strains, Western analysis and induction of regulated secretion was carried out as described in Example 3 except that Western analysis was carried out with an anti-HA antibody.

Results. Expression of pfs48/45$^{PrePro}$ in *Tetrahymena* was examined by Western analysis in both whole cell lysates and harvested mucus as described herein. FIG. 14 (Panel B) shows that pfs48/45$^{PrePro}$ is expressed and is recovered in mucus following induced release of mucocyst contents. A majority of fusion protein in the mucus resolves at approximately 64 kDa indicating that the prepro-domain of Grl4 has not been processed in vivo.

Example 10

Extraction/Purification

Materials were as described for Mucocyst Targeting Example 3. In addition TEV protease was purchased from Invitrogen and Ni-NTA affinity resin was purchased from Fisher Scientific. Construction of the H5ΔTMD$^{ProGrl1}$ expression cassette, generation of expression strains, Western analysis and induction of regulated secretion were as described for Mucocyst Targeting Example 3.

Extraction of H5ΔTMD$^{ProGrl1}$ from mucus and Purification by Ni-NTA chromatography. Mucus containing H5ΔTMD$^{ProGrl1}$ was re-suspended in 10× volumes of 5 mM Tris pH 6.9 and incubated overnight at 4° C. The mixture was centrifuged at high-speed (10,000×g for 30 min) to remove the insoluble matrix material and the supernatant was concentrated 10-fold with a 10 MWCO spin filter. The concentrated sample was treated with TEV protease at 30° C. and the mixture passed over a Ni-NTA column. The column was washed with 20 mM Tris-Cl, 50 mM NaCl and 40 mM imidazole and bound protein eluted in the same buffer containing 400 mM imidazole. Elution fraction containing H5ΔTMD were identified by Western analysis, pooled and concentrated 10-fold with a 10 MWCO spin filter prior to analysis by SDS-PAGE.

Results. Dilution of H5ΔTMD$^{ProGrl1}$-containing mucus with 5 mM Tris pH 6.9 and incubation overnight results in dissociation of H5ΔTMD$^{ProGrl1}$ from the insoluble mucus matrix (FIG. 15, Panel A). Furthermore, a majority of soluble protein resolves as monomer by SDS-PAGE indicating that the extraction process results in the ex vivo processing of the fusion protein, presumably by endogenous mucocyst associated proteases, leading to the separation of the H5ΔTMD and Grl1 proteins (FIG. 15, Panel A). Treatment of soluble extract with TEV protease leads to conversion of the remaining fusion protein to monomer (FIG. 15, Panel B). Soluble H5ΔTMD binds to and elutes from Ni-NTA affinity resin (FIG. 15, Panel C) leading to recovery of a purified sample of H5ΔTMD (FIG. 15, Panel D).

Example 10

Extraction/Purification Solubilization by Protease Treatment of Mucus

Materials were as described for Mucocyst Targeting Example 3. In addition TEV protease was purchased from Invitrogen and Ni-NTA affinity resin was purchased from Roche. Construction of the scFv$^{Grl1}$ expression cassette was as described for Mucocyst Targeting Example 7. Generation of expression strains, Western analysis and induction of regulated secretion were as described for Mucocyst Targeting Example 3.

Extraction of scFv$^{Grl1}$ from mucus by direct treatment with TEV protease. Mucus containing scFv$^{Grl1}$ was harvested as described herein. TEV protease was added directly to mucus at a concentration of 70U/ml mucus and incubated for 2 hours at 30° C. The mixture was centrifuged for 10 minutes at 8000×g and the soluble supernatant removed and passed over Ni-NTA resin (1 ml bed volume). The Ni-NTA column was washed in buffer containing 50 mM Tris-Cl, pH 8, 500 mM NaCl, 0.1% TX-100 and 20 mM imidazole. Bound protein was eluted in 1 ml fractions in buffer containing 50 mM Tris-Cl, pH 8, 500 mM NaCl, 0.05% TX-100 and 250 mM imidazole. Elution fractions containing soluble scFv were identified by anti-HA Western analysis.

Results. Treatment of mucus containing scFv$^{Grl1}$ directly with TEV protease results in the accumulation of soluble scFv as shown in FIG. 16 (Panel A, Lane S). This is presumably due to TEV dependant separation of the scFv and Grl1 fusion partners with the latter remaining associated with insoluble mucus matrix. Following solubilization, scFv is amenable to purification with Ni-NTA affinity chromatography as shown in FIG. 16, Panel B.

Example 11

Use of *Tetrahymena* Mucus as a Carrier and Immune Stimulating Matrix

Chimeric genes were synthesized by GenScript Inc (Piscataway, N.J.). Restriction enzymes were purchased from New England Biolabs. *Tetrahymena* cells were cultured in NEFF medium (0.25% proteose peptone, 0.25% yeast extract, 0.55% glucose, 33 μM FeCl$_3$) supplemented, when required, with paromomycin at a final concentration of 100 μg/ml. All medium components were acquired from VWR. For Biolistic transformations DNAdel™ S550d gold carrier particle suspension was purchased from Seashell Technology and filter paper from Whatman. Western analysis was carried out with a conformation specific neutralizing mouse monoclonal antibody, 5C5. Anti-rat and mouse horse-radish peroxidase (HRP)-conjugated secondary antibodies were purchased from Bio-Rad. Insect cell-derived H5N1 hemagglutinin was obtained from Protein Sciences. For mucus-vaccine preparation Dibucaine was purchased from Sigma-Aldrich and Protease Inhibitor Cocktail from Roche.

Expression construct design, synthesis and cloning: Fusion constructs were comprised of a truncated form of the avian influenza H5N1 hemagglutinin lacking the transmembrane domain (H5ΔTMD) fused in-frame to either the PrePro domain of *Tetrahymena* Grl1 (H5ΔTMD$^{PrePro}$, FIG. 9A) or a Grl1 protein comprising the Pro domain and mature Grl1 amino acid sequence (H5ΔTMD$^{ProGrl1}$, FIG. 8A). Genes encoding each fusion construct were chemically synthesized with flanking BamHI and SacI restriction sites and subsequently cloned into the same restriction sites of a *Tetrahymena* somatic expression vector, pXS76. In each case transcription of the transgene is under control of a robust cadmium-inducible promoter from the metallothionein-1 (MTT1) gene of *Tetrahymena thermophila*. Expression constructs comprising MTT1 promoter, transgene, MTT1 terminator and a neomycin resistance cassette were transferred, en masse, as a NotI fragment into a high-copy rDNA vector, pD5H8 and introduced into conjugating *Tetrahymena thermophila* strains by biolistic transformation.

Generation of expression strains: B2086 and CU428 *T. thermophila* strains were grown in modified NEFF medium (0.25% proteose peptone, 0.25% yeast extract, 0.55% glucose, 33 mM FeCl$_3$) at 30° C. One hundred ml of each logarithmically growing culture was centrifuged at 1,100×g for 2 minutes in oil centrifuge tubes, washed in 10 mM Tris pH 7.4 and resuspended in fresh 10 mM Tris pH 7.4 (starvation medium) at a concentration of 200,000-250,000 cells/ml. Cells were incubated for 9-18 hours at 30° C. After starvation, B2086 and CU428 cell cultures were counted and cell concentration was readjusted to 200,000 cells/ml. To induce conjugation, 100 ml of each strain were mixed together in a 4 L flask. Four transformations were performed between 9.5 and 10.5 hours post-mixing using a Biolistic PDS-1000/He Particle Delivery System (BIO-RAD). For each transformation, 20 ml of DNAdel™ S550d gold carrier particle suspension were coated with 4 µg of DNA construct according to manufacturer's instructions. Fifty ml of conjugating cells were concentrated to ~1 ml by centrifugation at 1,100×g in oil centrifuge tubes for 2 minutes. Cells were spread on a round 90 mm hardened paper filter (Whatman, Cat. #1450-090) pre-wet with 1.5 ml 10 mM Tris pH 7.4 inside a Petri dish. After the bombardment, the filter with the cells was transferred into a 500 ml flask containing 50 ml NEFF medium. The flasks were incubated on a slow shaker for ~20 hours at 30° C. At 30 hours post-mixing, 25 ml NEFF medium containing 300 µg/ml paromomycin was added to the 50 ml of cell culture (final paromomycin concentration, 100 µg/ml). Cells were aliquoted into 96 well microplates (150 ml per well). After 3-4 days, the microplates were examined and 5 ml from each of the wells containing paromomycin-resistant cells were transferred into 150 ml NEFF medium containing 100 µg/ml paromomycin on a master 96 well microplate.

Western analysis: To evaluate H5ΔTMD$^{PrePro}$ and H5ΔTMD$^{ProGrl1}$ expression, cultures were grown to ~5×10$^5$ cells/ml and induced for 12 hr with 1 µg/ml of CdCl$_2$. Cells were then harvested and lysed in SDS sample buffer in the absence of reducing agents. Proteins were resolved by SDS-PAGE and transferred to nitrocellulose membranes before Western blotting. Blots were probed with the neutralizing mouse monoclonal antibody, 5C5. This antibody recognizes conformational epitopes on H5 that are destroyed by treatment with disulfide reducing agents. Following incubation in primary antibody, blots were probed with secondary goat anti-mouse IgG coupled to HRP for visualization.

Preparation of mucus-based vaccine formulation: Expression strains were grown to a cell density of 5×10$^5$ cells/ml prior to induction with 1.5 µg/ml CdCl$_2$. Cells were harvested 16 h post-induction by centrifugation at 2000×g for 5 minutes. The cell pellet was re-suspended in Buffer A (40 mM Hepes, 1 mM CaCl$_2$) followed by the addition of Dibucaine to a final concentration of 2 mM to induce mucocyst release. An equal volume of ice-cold Buffer A containing 2× protease inhibitor cocktail (PIC) was added and then the mixture was centrifuged at 5000×g for 2 minutes to separate supernatant, mucus and cell pellet layers. The mucus layer was harvested and re-suspended in 10 volumes of Buffer A containing 1× PIC and centrifuged once more at 5000×g for 2 minutes. The mucus was re-suspended in Buffer A and used to immunize rats.

Animal immunizations and determination of anti-H5 antibody production by western analysis: Rats were immunized with either H5ΔTMD$^{PrePro}$ or H5ΔTMD$^{ProGrl1}$ mucus based vaccine and then with a booster shot approximately 4 weeks later. To determine production of anti-H5 antibodies, insect derived H5N1 hemagglutinin was resolved by SDS-PAGE and transferred to nitrocellulose. Blots were probed with sera collected from each rat and then with anti-rat HRP conjugated secondary antibody. Control blots were probed with either pre-immune sera or secondary antibody alone.

Microneutralization assays: Assays were carried out with the A/Vietnam/1203/2004xPR8 (VN04) strain with a tissue culture infectious dose$_{50}$ (TCID$_{50}$) of 3.2×10$^8$ virus particles/ml. A 1.6×10$^5$ viral particle dose was pre-incubated with serial dilutions of each lot of sera and MDCK cells were then added to the sera/virus mixtures and incubated for 20 hours. Cells were then fixed and the presence of Influenza A virus NP in infected cells was detected by ELISA. The absence of infectivity constitutes a positive neutralization reaction and indicates the presence of virus-specific antibodies in the sera.

Results. Expression of H5ΔTMD$^{PrePro}$ or H5ΔTMD$^{ProGrl1}$ in *Tetrahymena* was examined by Western analysis of both whole cell lysates and harvested mucus as described herein. FIG. 17 shows that each fusion gene was expressed and resolved at a molecular weight >148 kDa indicating the formation of higher order structures of the fusion protein. Such higher order structures are likely a consequence of the H5ΔTMD fusion partner since H5N1 hemagglutinin is known to trimerize. Both H5ΔTMD$^{PrePro}$ and H5ΔTMD$^{ProGrl1}$ are recovered in mucus following induced release of mucocyst contents (FIG. 17). Sera collected from rats immunized with either mucus-based H5ΔTMD$^{PrePro}$ or H5ΔTMD$^{ProGrl1}$ contained anti-hemagglutinin antibodies as judged by detection of insect cell derived recombinant H5N1 hemagglutinin by Western analysis (FIG. 3). Detection was specific for sera derived from immunized animals as pre-immune sera or secondary antibody alone failed to detect hemagglutinin (FIG. 18). Microneutralization assays confirmed the presence of neutralizing antibodies in sera derived from animals immunized with H5ΔTMD$^{PrePro}$ or H5ΔTMD$^{ProGrl1}$ with titers of 10240 and 2560, respectively. As a gauge of efficacy, neutralizing titers of approximately 10,000 are achieved when animals are hyper-immunized with live virus indicating that a similar efficacy is achieved using the mucus-based sub-unit vaccine.

References

Andrews (2000), "Regulated secretion of conventional lysosomes," *Trends Cell Biol.* 10:316-21.
Becker and Rusing (2003), "Structure of N-glycosidic carbohydrates of secretory proteins of *Tetrahymena thermophila*," *J. Eukaryot. Microbiol.* 50:235-239.
Berg et al. (1991), "Bispecific antibodies that mediate killing of cells infected with human immunodeficiency virus of any strain," *Proc. Natl. Acad. Sci. USA* 88:4723-4727.
Blomberg et al. (1997), "Regulatory sequences for the amplification and replication of the ribosomal DNA minichromosome in *Tetrahymena thermophila*," *Mol. Cell. Biol.* 12:7237-747.
Boldrin et al. (2006), "Metallothionein gene from *Tetrahymena thermophila* with a copper-inducible-repressible promoter," *Eukaryot Cell* 2:422-425.
Bowman et al. (2005a), "Genomic and proteomic evidence for a second family of dense core granule cargo proteins in *Tetrahymena thermophila*," *J. Eukaryot. Microbiol.* 52:291-7.
Bowman et al. (2005b), "Core formation and the acquisition of fusion competence are linked during secretory granule maturation in *Tetrahymena*," *Traffic* 6:303-23.
Bradshaw et al. (2003), "Proprotein processing within secretory dense core granules of *Tetrahymena thermophila*," *J. Biol. Chem.* 278:4087-4095.
Bruns and Cassidy-Hanley (2000), "Biolistic transformation of macro-and micronuclei," *Meth. Cell Biol.* 62:501-512.
Bruns et al. (1985), "A drug-resistant mutation in the ribosomal DNA of *Tetrahymena*," *Proc. Natl. Acad. Sci. USA* 9:2844-286.
Burgess and Kelly (1987), "Constitutive and Regulated Secretion of Proteins," *Annu. Rev. Cell Biol.* 3:243-293.
Cassidy-Hanley et al. (1997), "Germline and somatic transformation of mating *Tetrahymena thermophila* by particle bombardment," *Genetics* 146:135-147.
Chanat et al. (1993), "Reduction of the disulfide bond of chromogranin B (secretogranin I) in the trans-Golgi network causes its missorting to the constitutive secretory pathways," *EMBO J.* 12:2159-2168.
Chaudhary et al. (1990), "A rapid method of cloning functional variable-region antibody genes in *Escherichia coli* as single-chain immunotoxins," *Proc. Natl. Acad. Sci. USA* 87:1066-1070.
Chen et al. (1995), "Regulated secretion of prolactin by the mouse insulinoma cell line beta TC-3," *Biotechnology* 13:1191-7.
Chilcoat et al. (1996), "Granule lattice protein 1 (Grl1p), an acidic, calcium-binding protein in *Tetrahymena thermophila* dense-core secretory granules, influences granule size, shape, content organization, and release but not protein sorting or condensation," *J. Cell Biol.* 135(6 Pt 2):1775-87.
Clark et al. (2001), "The I-antigens of *Ichthyophthirius multifiliis* are GPI-anchored proteins," *J. Eukarot. Microbiol.* 48:332-337.
Collins and Wilhelm (1981), "Post-translational cleavage of mucocyst precursors in *Tetrahymena*," *J. Biol. Chem.* 256:10475-10484.
Cool et al. (1995), "Identification of the sorting signal motif within pro-opiomelanocortin for the regulated secretory pathway," *J. Biol. Chem.* 270:8723-8729.
Cool et al. (1997), "Carboxypeptidase E is a regulated secretory pathway sorting receptor: genetic obliteration leads to endocrine disorders in Cpe (fat) mice," *Cell* 88:73-83.
Cowan et al. (2005), "Genetic, genomic, and functional analysis of the granule lattice proteins in *Tetrahymena* secretory granules," *Mol. Biol. Cell.* 16:4046-4060.
de Coninck et al. (2000), "Industrial media and fermentation processes for improved growth and protease production by *Tetrahymena thermophila* Bill," *J. Industr. Microbiol. Biotechnol.* 24:285.
Eisen et al. (2006), "Macronuclear genome sequence of the ciliate *Tetrahymena thermophila*, a model eukaryote," *PLoS Biol.* 4(9):e286.
Frankel (2000), "The cell biology of *Tetrahymena thermophila*," *Meth. Cell Biol.* 62:27-125.
Gaertig and Gorovsky (1992), "Efficient mass transformation of *Tetrahymena thermophila* by electroporation of conjugants," *Proc. Natl. Acad. Sci. USA* 89:9196-9200.
Gaertig et al. (1994), "High frequency vector-mediated transformation and gene replacement in *Tetrahymena*," *Nucleic Acids Res.* 22:5391-5398.
Gaertig et al. (1999), "Surface display of a parasite antigen in the ciliate *Tetrahymena thermophila*," *Nature Biotech.* 17:462-465.
Gaertig and Kapler (2000), "Transient and stable DNA transformation of *Tetrahymena thermophila* by electroporation," *Meth. Cell Biol.* 62:486-500.
Glombik et al. (1999), "The disulfide-bonded loop of chromogranin B mediates membrane binding and directs sorting from the trans-Golgi network to secretory granules," *EMBO J.* 18:1059-1070.
Grampp et al. (1992), "Use of regulated secretion in protein production from animal cells: an overview," *Adv Biochem Eng Biotechnol.* 46:35-62.
Gundelfinger et al. (2003), "Temporal and spatial coordination of exocytosis and endocytosis," *Nat. Rev. Mol. Cell Biol.* 4(2):127-39.
Haddad et al. (2002), "New class of cargo protein in *Tetrahymena thermophila* dense core secretory granules," *Eukaryot. Cell.* 1:583-93.
Hai et al. (2000), "Knockout heterokaryons enable facile mutagenic analysis of essential genes in *Tetrahymena*," *Meth. Cell Biol.* 62:513-531.
Hellenbroich et al. (1999), "Cultivation of *Tetrahymena thermophila* in a 1.5 m3 airlift bioreactor," *Appl. Microbiol. Biotechnol.* 51:447.
Huse et al. (1989), "Generation of a large combinatorial library of the immunoglobulin repertoire in phage lambda," *Science* 246:1275-1281.
Langer (2005), 3rd Annual Report and Survey of Biopharmaceutical Manufacturing, Capacity and Production, BioPlan Associates, Inc.
Larsen et al. (1999), "Cloning and characterization of the gene encoding the highly expressed ribosomal protein 13 of the ciliated protozoan *Tetrahymena thermophila*. Evidence for differential codon usage in highly expressed genes," *Cell Biol. Int.* 23(8):551-60.
Lin et al. (2002), "The use of synthetic genes for the expression of ciliate proteins in heterologous systems," *Gene* 288(1-2):85-94.
Madeddu et al. (1994), "Protein processing and morphogenesis of secretory granules in *Paramecium*," *Biochimie.* 76:329-35.
Maihle and Satir (1986), "Protein secretion in *Tetrahymena thermophila*: Characterization of the major proteinaceous secretory proteins," *J. Biol. Chem.* 261(16):7566-70.

McCloskey (2004), "Creating therapeutic proteins from bioengineered systems," *Biotechnology Healthcare* (September issue) p. 58.

Melia et al. (1998), "Mutational analysis of regulated exocytosis in *Tetrahymena*," *J. Cell Sci.* 111(Pt. 1):131-40.

Miller and Moore (1990), "Regulated secretion," *Curr. Opin. Cell Biol.* 2:642-647.

Mullinax et al. (1990), "Identification of human antibody fragment clones specific for tetanus toxoid in a bacteriophage lambda immunoexpression library," *Proc. Natl. Acad. Sci. USA* 87:8095-8099.

Orias et al. (1988), "Replacement of the macronuclear ribosomal RNA genes of a mutant *Tetrahymena* using electroporation," *Gene* 2:295-301.

Pan et al. (1982), "Allele-specific, selective amplification of a ribosomal RNA gene in *Tetrahymena thermophila*," Cell 3:595-604.

Pavlou and Reichert (2004), "Recombinant protein therapeutics—success rates, market trends and values to 2010," *Nat. Biotechnol.* 22:1513-1519.

Pluckthun (1990), "Antibodies from *Escherichia coli*," *Nature* 347:497-498.

Roy et al. (1991), "Investigation of a possible role of the amino-terminal pro-region of proopiomelanocortin in its processing and targeting to secretory granules," *Mol. Cell. Endocrinol.* 82:237-250.

Satir (1977), "Dibucaine-induced synchronous mucocyst secretion in *Tetrahymena*," *Cell Biol. Int. Rep.* 1:69-73.

Shang et al. (2002), "A robust inducible-repressible promoter greatly facilitates gene knockouts, conditional expression, and overexpression of homologous and heterologous genes in *Tetrahymena thermophila*," *Proc. Natl. Acad. Sci. USA* 6:3734-379.

Spangler and Blackburn (1985), "The nucleotide sequence of the 17S ribosomal RNA gene of *Tetrahymena thermophila* and the identification of point mutations resulting in resistance to the antibiotics paromomycin and hygromycin," *J. Biol. Chem.* 10:6334-6340.

Taniguchi et al. (1985), "Carbohydrates of lysosomal enzymes secreted by *Tetrahymena pyriformis*," *J. Biol. Chem.* 260:13941-13946.

Tondravi and Yao (1986), "Transformation of *Tetrahymena thermophila* by microinjection of ribosomal RNA genes," *Proc. Natl. Acad. Sci USA* 83:4369-73.

Turkewitz (2004), "Out with a bang! *Tetrahymena* as a model system to study secretory granule biogenesis," *Traffic* 5:63-8.

Turkewitz et al. (2000), "Regulated protein secretion in *Tetrahymena thermophila*," *Meth. Cell Biol.* 62:347-362.

Turkewitz et al. (2002), "Functional genomics: the coming of age for *Tetrahymena thermophila*," *TRENDS in Genetics* 18:35-40.

Vayssié et al. (2000), "Molecular genetics of regulated secretion in *Paramecium*," *Biochimie*. 82:269-88.

Weide et al. (2006), "Secretion of functional human enzymes by *Tetrahymena thermophila*," *BMC Biotechnol.* 6:19.

Williams et al. (1980), "Studies of membrane formation in *Tetrahymena*: Identification of membrane proteins and turnover rates in non-growing cells," *J. Biol. Chem.* 255:296-303.

Wood et al. (1990), "High level synthesis of immunoglobulins in Chinese hamster ovary cells," *J. Immunol.* 145:3011-3016.

Wuitschick and Karrer (2000), "Codon usage in *Tetrahymena thermophila*," *Meth. Cell Biol.* 62:565-8.

Wuitschick and Karrer (1999), "Analysis of genomic G +C content, codon usage, initiator codon context and translation termination sites in *Tetrahymena thermophila*," *J. Eukaryot. Microbiol.* 46:239-247.

Yang and Hsieh (2001), "Regulated secretion of proinsulin/insulin from human hepatoma cells transduced by recombinant adeno-associated virus," *Biotechnol. Appl. Biochem.* 33:133-140.

Yu and Blackburn (1989), "Transformation of *Tetrahymena thermophila* with a mutated circular ribosomal DNA plasmid vector," *Proc. Natl. Acad. Sci. USA* 21:8487-891.

Yu et al. (1988), "Circular ribosomal DNA plasmids transform *Tetrahymena thermophila* by homologous recombination with endogenous macronuclear ribosomal DNA," *Proc. Natl. Acad. Sci. USA* 14:5151-5155

Zhang et al. (1999), "Identification of a novel prohormone sorting signal-binding site on carboxypeptidase E, a regulated secretory pathway-sorting receptor," *Mol. Endocrinol.* 13:527-536.

What is claimed is:

1. A method for production of a heterologous soluble polypeptide by a ciliate, the method comprising:
   (a) transforming said ciliate with a nucleic acid encoding a fusion protein comprising from N-terminus to C-terminus:
      (i) a mucocyst-targeting polypeptide of a mucocyst-targeted protein which is cleaved by a protease endogenous to said mucocyst; and
      (ii) a heterologous polypeptide;
   wherein expression of said fusion protein results in trafficking of said fusion protein to mucocysts within said ciliate and cleavage of said mucocyst-targeting polypeptide to release said heterologous soluble polypeptide within said mucocysts;
   (b) stimulating regulated secretion from said mucocysts of said ciliate, whereby an extracellular matrix is formed; and
   (c) separating said heterologous soluble polypeptide from said extracellular matrix and said ciliates.

2. A method for production of a heterologous soluble polypeptide by a ciliate, the method comprising:
   (a) transforming said ciliate with a nucleic acid encoding a first fusion protein comprising from N-terminus to C-terminus:
      (i) a heterologous polypeptide; and
      (ii) at least a mucocyst-targeting polypeptide of a mucocyst-targeted protein;
   wherein expression of said first fusion protein results in trafficking of said first fusion protein to mucocysts within said ciliate; and
   wherein an endogenous protease within said mucocysts cleaves a cleavage site within said mucocyst-targeting polypeptide and removes any sequences C-terminal to said cleavage site, thereby producing a second fusion protein within said mucocysts;
   (b) stimulating regulated secretion from said mucocysts of said ciliate, whereby an extracellular matrix is formed; and
   (c) separating said heterologous polypeptide from said extracellular matrix and said ciliates.

3. The method of claim 2 wherein said first fusion protein further comprises a second protease cleavage site between said heterologous polypeptide and said mucocyst-targeting polypeptide.

4. The method of claim 3, further comprising the step of reacting said second fusion protein with a second protease which cleaves said second protease cleavage site after step (b).

5. The method of claim 3, further comprising the step of reacting said second fusion protein with a second protease which cleaves said second protease cleavage site after step (c).

6. A method for producing a desired heterologous polypeptide in a culture of ciliates, the method comprising:
   (a) expressing a fusion protein comprising said heterologous polypeptide and a polypeptide comprising at least one mucocyst-targeting polypeptide of a mucocyst-targeted protein in said ciliates;
   (b) stimulating regulated secretion from mucocysts of said ciliates, whereby an extracellular matrix is formed by said secretion;
   (c) separating said extracellular matrix from said ciliates; and
   (d) isolating said fusion protein from said extracellular matrix.

7. The method of any of claim 1-6 wherein said mucocyst-targeted protein is a Grl protein.

8. The method of any of claim 1-6 wherein said mucocyst-targeted protein is selected from the group consisting of a Grl-1 protein, a Grl-2 protein a Grl-3 protein, a Grl-4 protein, a Grl-5 protein, a Grl-6 protein, a Grl-7 protein, a Grl-8 protein, a Grl-9 protein, and a Grl-10 protein.

9. The method of claim 8 wherein said mucocyst-targeted protein comprises a pro-domain of said Grl protein.

10. The method of any of claim 1-6 wherein said mucocyst-targeted protein is an Igr protein or a granule tip protein.

11. The method of any of claim 1-6 wherein said mucocyst-targeted protein is a β/γ crystalline domain or a C-terminal crystallin fold containing protein.

12. The method of any of claim 1-6 wherein said fusion protein further comprises an endoplasmic reticulum-targeting polypeptide N-terminal to said mucocyst-targeting polypeptide.

13. The method of claim 12 wherein said endoplasmic reticulum-targeting polypeptide is a pre-domain of a Grl protein.

14. The method of claim 12 wherein said endoplasmic reticulum-targeting polypeptide is heterologous to said mucocyst-targeting polypeptide.

15. A method for production of a heterologous soluble polypeptide by a ciliate, the method comprising:
(a) transforming said ciliate with a nucleic acid encoding a fusion protein comprising from N-terminus to C-terminus:
   (i) a soluble polypeptide endogenous to said mucocyst;
   (ii) a protease cleavage site; and
   (iii) a heterologous polypeptide;
wherein expression of said fusion protein results in trafficking of said fusion protein to mucocysts within said ciliate;
(b) stimulating regulated secretion from said mucocysts of said ciliate, whereby an extracellular matrix is formed by said secretion;
(c) separating said fusion protein from said extracellular matrix and said ciliates; and
(d) obtaining said heterologous soluble polypeptide from said fusion protein.

16. The method of claim 15 wherein said mucocyst-targeted protein is a β/γcrystalline domain containing or a C-terminal crystallin fold protein.

17. The method of claim 15 wherein step (d) comprises the step of reacting said heterologous soluble polypeptide with a protease which cleaves said protease cleavage site.

18. The method of any one of claims 15-17 wherein said fusion protein further comprises an endoplasmic reticulum-targeting polypeptide N-terminal to said heterologous polypeptide.

19. The method of claim 18 wherein expression of said fusion protein results in trafficking of said fusion protein to mucocysts within said ciliate and cleavage of said endoplasmic reticulum-targeting polypeptide.

20. The method of claim 18 wherein said endoplasmic reticulum-targeting polypeptide is a pre-domain of a Grl protein.

21. The method of claim 18 wherein said endoplasmic reticulum-targeting polypeptide is heterologous to said soluble polypeptide endogenous to said mucocyst.

* * * * *

UNITED STATES PATENT AND TRADEMARK OFFICE
CERTIFICATE OF CORRECTION

PATENT NO. : 8,722,361 B2
APPLICATION NO. : 13/257903
DATED : May 13, 2014
INVENTOR(S) : Clark et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 67 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 402
<212> TYPE: PRT
<213> ORGANISM: Tetrahymena thermophila

<400> SEQUENCE: 1

Met Asn Lys Lys Leu Leu Val Val Leu Phe Gly Phe Leu Ala Leu Ala
1               5                   10                  15

Ala Ala Thr Asn Gln Ser Glu Glu Glu Gly Ser Tyr Thr Ile Asp Gln
            20                  25                  30

Ala Ala Asn Leu Leu Asn Asp Leu Leu Ala Asp Ser Gln Gln Asn Leu
        35                  40                  45

Ser Asp Leu Gln Ala Ala Trp Ala Asn Lys Glu Pro Leu Leu Gln Gly
    50                  55                  60

Val Ile Ala Gly Leu Glu Ser Asp Leu Ala Asn Lys Gln Ala Glu Cys
65                  70                  75                  80
```

```
Ala Asp Leu Gln Gly Thr Leu Asp Ala Asp Gln Ala Ser Leu Asp Glu
            85                  90                  95

Ala Glu Ala Tyr Val Ala Trp Leu Gln Asp Arg Ile Ala Ala Asn His
            100                 105                 110

Lys Gln Ile Asp Asp Leu Leu Asn Arg Arg Cys Gln Gln Asn Gly Asn
            115                 120                 125

Tyr Ile Glu Gly Leu Lys Asn Asp Lys Leu Ala Leu Ala Leu Leu Gln
            130                 135                 140

Phe Leu Glu Ala Gln Ile Gln Asn Lys Glu Ser Phe Ser Phe Leu Gln
145                 150                 155                 160

Lys Lys Asn Phe Met Lys Lys Leu Thr Arg Phe Leu Ser Ile Tyr Lys
            165                 170                 175

Thr Gly Asn Tyr Gln Gln Leu Ala Leu Leu Glu Lys Glu Tyr Val Asn
            180                 185                 190

Ala Asp Asp Tyr Ser Val Asn Pro Asp Tyr Ser Thr Gly Asp Arg Thr
            195                 200                 205

Ala Asp Glu Ile Gly Ser Gly His Ile Asp Asn Asp Lys Gly Asp Ile
            210                 215                 220

Asp Val Ala Asp Phe Gln Glu Gly Glu Arg Lys Gly Trp Tyr Gln Val
225                 230                 235                 240

Lys Gln Glu Leu Leu Asp Leu Leu His Asn Leu Glu Gln Thr Ile Glu
            245                 250                 255

Ala Lys Ile Gln Gln Ala Gln Glu Asp Glu Val Asn Ser Asn Ser Ala
            260                 265                 270

Ala Ala Asp Phe Lys Ser Lys Leu Glu His Glu Ile Gln Val Tyr Glu
            275                 280                 285

Arg Glu Leu Ala Lys Trp Gln Gln Thr Val Ala Ala Leu Thr Ala Thr
            290                 295                 300

Val Ala Gln Asp His Glu Asn Val Asn Asn Cys His Ser Gln Glu Ala
305                 310                 315                 320

Ala Ile Gln Ala Asn Leu Asp Ala Ala Asn Gln Asp Tyr Ala Asn Glu
            325                 330                 335

Lys Ala Thr Phe Glu His Lys Gln Ala Asn Leu Gln Glu Glu Ile Glu
            340                 345                 350

Ile Phe Ile Glu Val Ile Ala Tyr Tyr Asp Asp Asn Val Gln Asn Ala
            355                 360                 365

Gly Glu Asp Leu Lys Glu Arg Val Glu Asp Tyr Ser Asp Gly Asn Phe
            370                 375                 380

Asp Asp Ala Ala Thr Tyr Glu Asn Arg Gln Val Pro Asn Ile Asp Phe
385                 390                 395                 400

Ile Asn

<210> SEQ ID NO 2
<211> LENGTH: 377
<212> TYPE: PRT
<213> ORGANISM: Tetrahymena thermophila

<400> SEQUENCE: 2

Met Lys Asn Leu Ala Ile Val Leu Ala Ala Leu Cys Ile Phe Ala Gln
1               5                   10                  15

Ala Thr Ser Val Phe Glu Thr Pro Ala Phe Leu Glu Ile Lys Ser Asn
            20                  25                  30

Pro Phe Gly His Thr Val Ala Ser Leu Val Gln Leu Asn Leu Gly Ala
            35                  40                  45

Gly Gln Ser Ala Gly Arg Leu Asp Ala Ile Ala Glu Ala Leu Asn Thr
```

```
            50                  55                  60
Ile Glu Ala Gln Leu Glu Asn Thr Arg Asp His Asn Asp Ala Glu Ile
 65                  70                  75                  80

Gln Arg Gln Arg Gly Trp Cys Ser Asp Gln Glu Ala Thr Ile Gln Ala
                 85                  90                  95

Asn Ile Asp Gln Ala Glu Ser Asp Leu Ser Asn Tyr Gln Asn Glu Gln
            100                 105                 110

Thr Gln Arg Asn Gln Ala Val Ala Asp Leu Thr Gln Asn Leu Asn Asn
        115                 120                 125

Glu Gln Gln Ser Leu Ala Glu Asn Gln Asn Asn Leu Ala Asn Ala Gln
    130                 135                 140

Gln Glu Leu Asp Asp Glu Asn Ser Ser Tyr Ala Glu Ser Ser Lys Asp
145                 150                 155                 160

Tyr Ala Asp Ala Ile Ala Ala Cys Glu Gln Ala Leu Lys Leu Leu Ala
                165                 170                 175

Thr Leu Gln Thr Asn Pro Ser Gly Phe Ile Gln Ser Lys Ala Arg Phe
            180                 185                 190

Gly Asn Val Val Thr Leu Leu Gln Lys His Leu Ala Asn Lys Ser Ser
        195                 200                 205

Asn Phe Val Gln Pro Ile Leu Asn Val Leu Thr Glu Met Ala Ser Ser
    210                 215                 220

Thr Asn Glu Val Asp Gln Ser Ser Leu Ala Lys Val Val Ser Leu Ile
225                 230                 235                 240

Asn Asp Leu Leu Glu Glu Leu Arg Asn Gln Ser Ala Ala Asn Asp Gln
                245                 250                 255

Arg His Gln Gln Val Val Asp Ser Leu Thr Ser Asn Ile Ala Asn Leu
            260                 265                 270

Glu Gln Leu Ile Asp Asn Ser Asn Asn Leu Ile Ser Gln Tyr Gln Gly
        275                 280                 285

Gln Ile Gln Glu Asn Glu Asp Arg Leu Ala Gln Leu Ala Gly Leu Ile
    290                 295                 300

Gln Gln Thr Gln Ala Ile Leu Asp Gln Ala Asn Gln Asn Leu Ser Gln
305                 310                 315                 320

Val Gln Asp Gln Cys Ala Gly Tyr Asp Gln Glu Tyr Ala Ser Phe Lys
                325                 330                 335

Asn Glu Val Asp Gln Gln Leu Ala Thr Leu Gln Ala Leu Lys Glu Tyr
            340                 345                 350

Phe Lys Ser Lys Val Val Pro Ala Val Glu Asn Ile Asn Asp Ser Ala
        355                 360                 365

Tyr Ala Asp Glu Leu Thr Val Asp Val
    370                 375

<210> SEQ ID NO 3
<211> LENGTH: 394
<212> TYPE: PRT
<213> ORGANISM: Tetrahymena thermophila

<400> SEQUENCE: 3

Met Arg Tyr Ala Ala Leu Phe Leu Leu Ala Leu Ile Ser Phe Asn Ala
 1               5                  10                  15

Val Tyr Ala Val Ser Leu Arg Lys Ser Ser Asp Ala Met Lys Thr Ser
                20                  25                  30

Phe Ala Leu Glu Arg Leu Arg Phe Ile Gly Lys Lys Ser Pro Ile Ala
            35                  40                  45

Lys Gln Ile Ile Ser Ala Val Glu Leu His Leu Thr Thr Gly Gly Leu
```

```
                50                  55                  60
Val Asp Asp Val Ile Asp Leu Val Lys Gln Ala Gln Glu Asp Val Ala
 65                  70                  75                  80

Asn Arg Asn Val Ala Leu Gln Ala Glu Tyr Thr Ala Lys Arg Gly Ala
                 85                  90                  95

Leu Glu Asp Gln Ile Asn Thr Thr Gln Leu Asn Glu Glu Asn
                100                 105                 110

Asp Arg Leu Ala Val Val Asn Asp Ala Ile Ala Leu Asn Gly Gln
                115                 120                 125

Ile Asp Ser Leu Asn Thr Gln Ile Ala Asn Leu Val Gln Gln Leu Gln
130                 135                 140

Asn Leu Gln Ala Arg Glu Asp Ala Ile Asn Gln Ala Arg Glu Val Asp
145                 150                 155                 160

Val Lys Thr Tyr Glu Val Arg Lys Gln Arg Asp Glu Asn Ser Leu Ala
                165                 170                 175

Val Leu Glu Gln Ile Ile Gln Arg Leu Leu Ala Leu Gln Gln Arg Gly
                180                 185                 190

Asn Ala Phe Leu Gln Val Ser Lys Lys Glu Ile Glu Arg Ile Leu Lys
                195                 200                 205

Arg Ile Pro Lys Ser Asn Pro Ile Gln Ala Leu Val Gln Leu Ser Thr
210                 215                 220

Lys Phe Asp Glu Gln Arg Leu Ala Glu Val Ile Ser Lys Leu Gln Thr
225                 230                 235                 240

Ile Gln Ala Ala Ile Gln Ala Ser Tyr Ile Glu Asp Ala Asn Gly Glu
                245                 250                 255

Val Ala Asp Lys Gln Arg Tyr Asp Ala Leu Ile Gln Glu Ile Ala Thr
                260                 265                 270

Ile Arg Ala Gln Thr Gln Gln Leu Ala Asp Ala Gln Gln Ala Leu
                275                 280                 285

Ser Asp Ala Glu Ala Ser Leu Ala Gln Phe Val Gln Gln Gly Asn
    290                 295                 300

Leu Gln Gln Gln Ile Ala Val Asn Glu Gly Ile Leu Ala Asp Ala Gln
305                 310                 315                 320

Ala Ala Leu Ala His Thr Ile Ala Thr Tyr Glu Ala Arg Ile Gln Glu
                325                 330                 335

Gly Gln Glu Ala Leu Ala Ala Ile Asn Leu Ala Leu Asp Val Leu Gln
                340                 345                 350

Gln Asn Gln Ser Asp Leu Gln Gly Val Glu Asp Phe Ser Asn Ala Tyr
                355                 360                 365

Asn Ala Tyr Gln Ala Gly Asn Ser Thr Asp Ala Gly Asp Ala Gly
370                 375                 380

Asp Asp Ser Gly Val Glu Gly Glu Ala Phe
385                 390

<210> SEQ ID NO 4
<211> LENGTH: 377
<212> TYPE: PRT
<213> ORGANISM: Tetrahymena thermophila

<400> SEQUENCE: 4

Met Arg Val Ile Ala Ala Leu Leu Val Ile Ala Leu Val Cys Gln Ser
  1               5                  10                  15

Ala Met Ala Val Thr Ser Lys Ser Gln Ala Lys Leu Met Met Glu Lys
                 20                  25                  30

Ile Asn Ser Lys Leu Glu Lys Ser His Leu Gly Arg Ala Leu Lys Gly
```

```
                    35                  40                  45
Met Val Thr Ile Ala Thr Lys Leu Gly Tyr Asp Tyr Gln Asp Leu Tyr
 50                  55                  60

Asp Ala Phe Ala Ala Leu Lys Asn Gln Leu Leu Asn Asn Leu Asp Asn
 65                  70                  75                  80

Glu Asn Ser Leu Phe Glu Thr Gln Thr Ala Ser His Asp Ser Ala Val
                 85                  90                  95

Ala Gln Phe Asn Ala Asp Ile Ser Asn Tyr Asn Gly Gln Ile Asn Asp
                100                 105                 110

Ala Gln Ala Gln Leu Asn Asp Leu Asn Asp Ser Leu Asn Thr Tyr Gln
                115                 120                 125

Gln Asn Leu Gln Asp Ala Gln Gln Ala Leu Gln Asp Asn Thr Asp Ala
            130                 135                 140

Leu Asn Ala Ala Glu Glu Ala Leu Ala Asn Ala Glu Ala Leu Tyr Gln
145                 150                 155                 160

Val Ala Thr Ala Glu Tyr Ser Asn Ala Asp Gln Val Ile Gly Leu Ala
                165                 170                 175

Val Glu Lys Leu Gln Glu Ala Gln Ser His Tyr Asp Asn Ala Asp Leu
                180                 185                 190

Gly Ser Phe Ser Phe Val Gln Ile Lys Asn Thr Phe Val Ser Phe Ala
                195                 200                 205

Gln Lys Val Thr Glu Ala Thr Lys Gly Met Asn Ala Lys His Gln Leu
            210                 215                 220

Phe Val Lys Pro Val Val Gln Ala Met Met Gln Val Lys Asn Asn Thr
225                 230                 235                 240

Ser Gln Ser Ser Ile Gln Thr Ala Ile Lys Ala Leu Gln Asp Leu Gln
                245                 250                 255

Ala Tyr Phe Gln Lys Thr Phe Ser Asp Leu Thr Asn Glu Tyr Val Ser
                260                 265                 270

Phe Thr Gln Asn Val Gln Ser Thr Ile Asp Gly Leu Asn Gln Ile Ile
                275                 280                 285

Asp Ile Leu Gln Asn Gln Val Ile Pro Gly Tyr Glu Ala Gln Ile Ser
290                 295                 300

Ser Leu Gln Ala Gln Ile Gln Gln Val Glu Asp Ala Leu Ala Leu Ala
305                 310                 315                 320

Gln Gln Asn Leu Gln Asp Ala Gln Asn Ala Leu Asp Ala Glu Asn Ala
                325                 330                 335

Gln Trp Glu Asn Val Val Ala Arg His Gln Ala Leu Val Asp Arg Ile
                340                 345                 350

Asn Ser Glu Tyr Asp Leu Val Thr Gln Ala Asp Arg Ile Val Arg Asn
                355                 360                 365

Ala Gln Ala Gln Val Asn Gly Ser Asp
                370                 375

<210> SEQ ID NO 5
<211> LENGTH: 385
<212> TYPE: PRT
<213> ORGANISM: Tetrahymena thermophila

<400> SEQUENCE: 5

Met Arg Lys Val Phe Val Ala Leu Ala Leu Val Ala Ile Ile Val Ser
  1               5                  10                  15

Ala Thr Met Leu Pro Glu Val Arg Gln Arg Ala Lys Val Ser Leu Gln
                 20                  25                  30

Lys Leu His Lys Ser Arg Ile Gly Lys Asn Ile Val Thr Ala Ile Gln
```

```
                    35                  40                  45
Leu Glu Leu Ser Ser Lys Asn Arg Asp Asn Ile Ile Val Asn Ile Leu
 50                  55                  60

Ala Leu Leu Asn Asp Leu Leu Asn Asp Gln Ser Thr Gln Leu Thr Lys
 65                  70                  75                  80

Ala Gln Ser Asp Leu Ala Asp Lys Gln Asp Tyr Cys Gly Ser Ser Ile
                 85                  90                  95

Glu Ser Tyr Gln Asn Gln Ile Ala Ser Lys Gln Ala Asp Ile Ala Asn
            100                 105                 110

Ala Gln Ala Ser Leu Pro Ala Leu His Ala Glu Leu Glu Thr Asp Gln
            115                 120                 125

Ala Asn Leu Ala Asp Gln Glu Ala Lys Leu Asp Arg Ala Gln Gln Asn
       130                 135                 140

Leu Ala Glu Ala Asn Asp Leu Asn Asp Ala Ala Val Ala Ala Phe Asn
145                 150                 155                 160

Thr Ser Ile Ala Asn His Asn Ala Met Ile Asp Ala Leu Lys Gln Ala
                165                 170                 175

Arg Ala Leu Ile Val Gln Leu Gln Ser Ser Phe Leu Gln Lys Asn
            180                 185                 190

Asn Ala Val Leu Ile Gln Leu Ser Asn His Lys Ala Leu Ala Leu Lys
        195                 200                 205

Lys Leu Glu Gly His Ala Lys Lys Ser Leu Phe Ser Leu Leu Met Gln
        210                 215                 220

Met Ala Gln Asp Val Gly Ile Gln Ala Asp Gln Thr Leu Val Gly Asn
225                 230                 235                 240

Val Leu Thr Val Ile Asp Asp Leu Leu Gln His Glu Gln Asp Gly Ile
                245                 250                 255

Asp Ala Glu Thr Gln Ala Glu Asn Gln Arg Val Glu Glu Tyr Asn Ala
            260                 265                 270

Ala Val Ile Asp Phe Asn Asn Gln Ile Ser Asp Ala Gln Gly Gln Ile
            275                 280                 285

Ala Ser Leu Asn Gln Asp Ile Gln Thr Leu Thr Asn Asn Ile Asn Asp
        290                 295                 300

Thr Glu Asn Asn Ile Ala Thr Trp Ser Gln Gln Val Ser Asp Leu Gln
305                 310                 315                 320

Gly Val Leu Asp Glu Leu Gln Asn Gln Cys Asn Ala Asp Ile Ala His
                325                 330                 335

Phe Gln Asp Leu Ile Gln Glu Leu Asn Gly Ile Gln Ile Ile Gln
            340                 345                 350

Gln Val Ile Ala Ile Phe Glu Gly Gln Ser Ile Gln Asp Val Lys Pro
        355                 360                 365

Leu Phe Asp Asp Ile Ser Val Asp Asp Gly Leu Gly Ser Ala Glu Ser
        370                 375                 380

Ala
385

<210> SEQ ID NO 6
<211> LENGTH: 923
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Gly Ser Glu Lys Ile Val Leu Leu Phe Ala Ile Val Ser Leu Val
```

-continued

```
1               5               10              15
Lys Ser Asp Gln Ile Cys Ile Gly Tyr His Ala Asn Asn Ser Thr Glu
                20              25              30

Gln Val Asp Thr Ile Met Glu Lys Asn Val Thr Val Thr His Ala Gln
            35              40              45

Asp Ile Leu Glu Lys Thr His Asn Gly Lys Leu Cys Asp Leu Asp Gly
        50              55              60

Val Lys Pro Leu Ile Leu Arg Asp Cys Ser Val Ala Gly Trp Leu Leu
65              70              75              80

Gly Asn Pro Met Cys Asp Glu Phe Ile Asn Val Pro Glu Trp Ser Tyr
                85              90              95

Ile Val Glu Lys Ala Asn Pro Val Asn Asp Leu Cys Tyr Pro Gly Asp
                100             105             110

Phe Asn Asp Tyr Glu Glu Leu Lys His Leu Leu Ser Arg Ile Asn His
            115             120             125

Phe Glu Lys Ile Gln Ile Ile Pro Lys Ser Ser Trp Ser Ser His Glu
        130             135             140

Ala Ser Leu Gly Val Ser Ser Ala Cys Pro Tyr Gln Gly Lys Ser Ser
145             150             155             160

Phe Phe Arg Asn Val Val Trp Leu Ile Lys Lys Asn Ser Thr Tyr Pro
                165             170             175

Thr Ile Lys Arg Ser Tyr Asn Asn Thr Asn Gln Glu Asp Leu Leu Val
                180             185             190

Leu Trp Gly Ile His His Pro Asn Asp Ala Ala Glu Gln Thr Lys Leu
            195             200             205

Tyr Gln Asn Pro Thr Thr Tyr Ile Ser Val Gly Thr Ser Thr Leu Asn
        210             215             220

Gln Arg Leu Val Pro Arg Ile Ala Thr Arg Ser Lys Val Asn Gly Gln
225             230             235             240

Ser Gly Arg Met Glu Phe Phe Trp Thr Ile Leu Lys Pro Asn Asp Ala
                245             250             255

Ile Asn Phe Glu Ser Asn Gly Asn Phe Ile Ala Pro Glu Tyr Ala Tyr
                260             265             270

Lys Ile Val Lys Lys Gly Asp Ser Thr Ile Met Lys Ser Glu Leu Glu
            275             280             285

Tyr Gly Asn Cys Asn Thr Lys Cys Gln Thr Pro Met Gly Ala Ile Asn
        290             295             300

Ser Ser Met Pro Phe His Asn Ile His Pro Leu Thr Ile Gly Glu Cys
305             310             315             320

Pro Lys Tyr Val Lys Ser Asn Arg Leu Val Leu Ala Thr Gly Leu Arg
                325             330             335

Asn Ser Pro Gln Arg Glu Arg Arg Lys Lys Arg Gly Leu Phe Gly
                340             345             350

Ala Ile Ala Gly Phe Ile Glu Gly Gly Trp Gln Gly Met Val Asp Gly
            355             360             365

Trp Tyr Gly Tyr His His Ser Asn Glu Gln Gly Ser Gly Tyr Ala Ala
        370             375             380

Asp Lys Glu Ser Thr Gln Lys Ala Ile Asp Gly Val Thr Asn Lys Val
385             390             395             400

Asn Ser Ile Ile Asp Lys Met Asn Thr Gln Phe Glu Ala Val Gly Arg
                405             410             415

Glu Phe Asn Asn Leu Glu Arg Arg Ile Glu Asn Leu Asn Lys Lys Met
                420             425             430
```

-continued

```
Glu Asp Gly Phe Leu Asp Val Trp Thr Tyr Asn Ala Glu Leu Leu Val
            435                 440                 445
Leu Met Glu Asn Glu Arg Thr Leu Asp Phe His Asp Ser Asn Val Lys
450                 455                 460
Asn Leu Tyr Asp Lys Val Arg Leu Gln Leu Arg Asp Asn Ala Lys Glu
465                 470                 475                 480
Leu Gly Asn Gly Cys Phe Glu Phe Tyr His Lys Cys Asp Asn Glu Cys
                485                 490                 495
Met Glu Ser Val Arg Asn Gly Thr Tyr Asp Tyr Pro Gln Tyr Ser Glu
            500                 505                 510
Glu Ala Arg Leu Lys Arg Glu Glu Ile Ser His His His His His His
            515                 520                 525
His His His His Glu Asn Leu Tyr Phe Gln Gly Thr Asn Gln Ser Glu
        530                 535                 540
Glu Glu Gly Ser Tyr Thr Ile Asp Gln Ala Ala Asn Leu Leu Asn Asp
545                 550                 555                 560
Leu Leu Ala Asp Ser Gln Gln Asn Leu Ser Asp Leu Gln Ala Ala Trp
                565                 570                 575
Ala Asn Lys Glu Pro Leu Leu Gln Gly Val Ile Ala Gly Leu Glu Ser
            580                 585                 590
Asp Leu Ala Asn Lys Gln Ala Glu Cys Ala Asp Leu Gln Gly Thr Leu
            595                 600                 605
Asp Ala Asp Gln Ala Ser Leu Asp Glu Ala Glu Ala Tyr Val Ala Trp
        610                 615                 620
Leu Gln Asp Arg Ile Ala Ala Asn His Lys Gln Ile Asp Asp Leu Leu
625                 630                 635                 640
Asn Arg Arg Cys Gln Gln Asn Gly Asn Tyr Ile Glu Gly Leu Lys Asn
                645                 650                 655
Asp Lys Leu Ala Leu Ala Leu Leu Gln Phe Leu Glu Ala Gln Ile Gln
            660                 665                 670
Asn Lys Glu Ser Phe Ser Phe Leu Gln Lys Lys Asn Phe Met Lys Lys
            675                 680                 685
Leu Thr Arg Phe Leu Ser Ile Tyr Lys Thr Gly Asn Tyr Gln Gln Leu
        690                 695                 700
Ala Leu Leu Glu Lys Glu Tyr Val Asn Ala Asp Asp Tyr Ser Val Asn
705                 710                 715                 720
Pro Asp Tyr Ser Thr Gly Asp Arg Thr Ala Asp Glu Ile Gly Ser Gly
                725                 730                 735
His Ile Asp Asn Asp Lys Gly Asp Ile Asp Val Ala Asp Phe Gln Glu
            740                 745                 750
Gly Glu Arg Lys Gly Trp Tyr Gln Val Lys Gln Glu Leu Leu Asp Leu
            755                 760                 765
Leu His Asn Leu Glu Gln Thr Ile Glu Ala Lys Ile Gln Gln Ala Gln
        770                 775                 780
Glu Asp Glu Val Asn Ser Asn Ser Ala Ala Ala Asp Phe Lys Ser Lys
785                 790                 795                 800
Leu Glu His Glu Ile Gln Val Tyr Glu Arg Glu Leu Ala Lys Trp Gln
                805                 810                 815
Gln Thr Val Ala Ala Leu Thr Ala Thr Val Ala Gln Asp His Glu Asn
            820                 825                 830
Val Asn Asn Cys His Ser Gln Glu Ala Ala Ile Gln Ala Asn Leu Asp
            835                 840                 845
Ala Ala Asn Gln Asp Tyr Ala Asn Glu Lys Ala Thr Phe Glu His Lys
        850                 855                 860
```

```
Gln Ala Asn Leu Gln Glu Glu Ile Glu Ile Phe Ile Glu Val Ile Ala
865                 870                 875                 880

Tyr Tyr Asp Asp Asn Val Gln Asn Ala Gly Glu Asp Leu Lys Glu Arg
            885                 890                 895

Val Glu Asp Tyr Ser Asp Gly Asn Phe Asp Asp Ala Ala Thr Tyr Glu
            900                 905                 910

Asn Arg Gln Val Pro Asn Ile Asp Phe Ile Asn
        915                 920
```

<210> SEQ ID NO 7
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Gly Ser Asn Lys Lys Leu Leu Val Val Leu Phe Gly Phe Leu Ala
1               5                   10                  15

Leu Ala Ala Ala Thr Asn Gln Ser Glu Glu Gly Ser Tyr Thr Ile
            20                  25                  30

Asp Gln Ala Ala Asn Leu Leu Asn Asp Leu Leu Ala Asp Ser Gln Gln
        35                  40                  45

Asn Leu Ser Asp Leu Gln Ala Ala Trp Ala Asn Lys Glu Pro Leu Leu
    50                  55                  60

Gln Gly Val Ile Ala Gly Leu Glu Ser Asp Leu Ala Asn Lys Gln Ala
65                  70                  75                  80

Glu Cys Ala Asp Leu Gln Gly Thr Leu Asp Ala Asp Gln Ala Ser Leu
                85                  90                  95

Asp Glu Ala Glu Ala Tyr Val Ala Trp Leu Gln Asp Arg Ile Ala Ala
            100                 105                 110

Asn His Lys Gln Ile Asp Asp Leu Leu Asn Arg Arg Cys Gln Gln Asn
        115                 120                 125

Gly Asn Tyr Ile Glu Gly Leu Lys Asn Asp Lys Leu Ala Leu Ala Leu
    130                 135                 140

Leu Gln Phe Leu Glu Ala Gln Ile Gln Asn Lys Glu Ser Phe Ser Phe
145                 150                 155                 160

Leu Gln Lys Lys Asn Phe Met Lys Lys Leu Thr Arg Phe Leu Ser Ile
                165                 170                 175

Tyr Lys Thr Gly Asn Tyr Gln Gln Leu Ala Leu Leu Glu Lys Glu Tyr
            180                 185                 190

Val Asn Ala Asp Gln Ile Cys Ile Gly Tyr His Ala Asn Asn Ser Thr
        195                 200                 205

Glu Gln Val Asp Thr Ile Met Glu Lys Asn Val Thr Val Thr His Ala
    210                 215                 220

Gln Asp Ile Leu Glu Lys Thr His Asn Gly Lys Leu Cys Asp Leu Asp
225                 230                 235                 240

Gly Val Lys Pro Leu Ile Leu Arg Asp Cys Ser Val Ala Gly Trp Leu
                245                 250                 255

Leu Gly Asn Pro Met Cys Asp Glu Phe Ile Asn Val Pro Glu Trp Ser
            260                 265                 270

Tyr Ile Val Glu Lys Ala Asn Pro Val Asn Asp Leu Cys Tyr Pro Gly
        275                 280                 285

Asp Phe Asn Asp Tyr Glu Glu Leu Lys His Leu Leu Ser Arg Ile Asn
    290                 295                 300
```

```
His Phe Glu Lys Ile Gln Ile Ile Pro Lys Ser Ser Trp Ser Ser His
305                 310                 315                 320

Glu Ala Ser Leu Gly Val Ser Ser Ala Cys Pro Tyr Gln Gly Lys Ser
            325                 330                 335

Ser Phe Phe Arg Asn Val Val Trp Leu Ile Lys Lys Asn Ser Thr Tyr
                340                 345                 350

Pro Thr Ile Lys Arg Ser Tyr Asn Asn Thr Asn Gln Glu Asp Leu Leu
            355                 360                 365

Val Leu Trp Gly Ile His His Pro Asn Asp Ala Ala Glu Gln Thr Lys
    370                 375                 380

Leu Tyr Gln Asn Pro Thr Thr Tyr Ile Ser Val Gly Thr Ser Thr Leu
385                 390                 395                 400

Asn Gln Arg Leu Val Pro Arg Ile Ala Thr Arg Ser Lys Val Asn Gly
                405                 410                 415

Gln Ser Gly Arg Met Glu Phe Phe Trp Thr Ile Leu Lys Pro Asn Asp
            420                 425                 430

Ala Ile Asn Phe Glu Ser Asn Gly Asn Phe Ile Ala Pro Glu Tyr Ala
                435                 440                 445

Tyr Lys Ile Val Lys Lys Gly Asp Ser Thr Ile Met Lys Ser Glu Leu
    450                 455                 460

Glu Tyr Gly Asn Cys Asn Thr Lys Cys Gln Thr Pro Met Gly Ala Ile
465                 470                 475                 480

Asn Ser Ser Met Pro Phe His Asn Ile His Pro Leu Thr Ile Gly Glu
                485                 490                 495

Cys Pro Lys Tyr Val Lys Ser Asn Arg Leu Val Leu Ala Thr Gly Leu
            500                 505                 510

Arg Asn Ser Pro Gln Arg Glu Arg Arg Lys Lys Arg Gly Leu Phe
                515                 520                 525

Gly Ala Ile Ala Gly Phe Ile Glu Gly Gly Trp Gln Gly Met Val Asp
    530                 535                 540

Gly Trp Tyr Gly Tyr His His Ser Asn Glu Gln Gly Ser Gly Tyr Ala
545                 550                 555                 560

Ala Asp Lys Glu Ser Thr Gln Lys Ala Ile Asp Gly Val Thr Asn Lys
                565                 570                 575

Val Asn Ser Ile Ile Asp Lys Met Asn Thr Gln Phe Glu Ala Val Gly
                580                 585                 590

Arg Glu Phe Asn Asn Leu Glu Arg Arg Ile Glu Asn Leu Asn Lys Lys
            595                 600                 605

Met Glu Asp Gly Phe Leu Asp Val Trp Thr Tyr Asn Ala Glu Leu Leu
    610                 615                 620

Val Leu Met Glu Asn Glu Arg Thr Leu Asp Phe His Asp Ser Asn Val
625                 630                 635                 640

Lys Asn Leu Tyr Asp Lys Val Arg Leu Gln Leu Arg Asp Asn Ala Lys
                645                 650                 655

Glu Leu Gly Asn Gly Cys Phe Glu Phe Tyr His Lys Cys Asp Asn Glu
            660                 665                 670

Cys Met Glu Ser Val Arg Asn Gly Thr Tyr Asp Tyr Pro Gln Tyr Ser
    675                 680                 685

Glu Glu Ala Arg Leu Lys Arg Glu Glu Ile Ser His His His His
            690                 695                 700

His His His His His
705
```

```
<210> SEQ ID NO 8
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Met Gly Ser Arg Lys Ile Ile Leu Leu Ala Ile Ile Ser Leu Ala
1               5                   10                  15

Leu Cys Gln Glu Leu Ile Val Glu Lys Val Ala Gly Gln Tyr Asn Ser
            20                  25                  30

Gly Gln Lys Phe Ala Lys Ser Trp Gln Asn Ser Gln Trp Asn Asp Tyr
            35                  40                  45

Gln Asp Phe Ala Ile Tyr Gly Trp Phe Lys Ile Asp Ser Ser Tyr Gln
50                  55                  60

Ile Ala Glu Trp Ser Thr Gly Phe His Phe Thr Ser Asn Gln Asp Lys
65                  70                  75                  80

Asp Trp Thr Asn Ala Ser Ala Pro Gly Asp Arg Val Leu Ala Phe Trp
                85                  90                  95

Val Ile Gly Asn Thr Leu His Asn Pro Thr Tyr Ser Leu Ala Arg Gly
            100                 105                 110

Asn Thr Asn Tyr Tyr Glu Asn Leu Ser Phe Ala Ala Gly Asp Thr Asn
            115                 120                 125

Lys Trp Ala Phe Ile Tyr Val Thr His Gly Ser Ser Gln Gln Ala Gln
130                 135                 140

Tyr Val Tyr Tyr Leu Leu Pro Ser Ser Gly Val Val Thr Lys Lys Ile
145                 150                 155                 160

Ala Ser Ile Thr His Lys Thr Ser Thr Phe Tyr Gln Ile Asn Val Gly
                165                 170                 175

Gln Ser Phe Ser Phe Lys Tyr Phe Pro Gly Ser Phe Trp Arg Leu Ser
            180                 185                 190

Leu Ile Ala Gly Pro Asn Ala Tyr Arg Glu Ser Gly Phe Glu Gln Phe
            195                 200                 205

Gln Asn Ile Gln Pro Asp Val Val Pro Ser Cys Pro Ile Leu Phe Thr
210                 215                 220

Gly Cys Asn Tyr Ser Gly Lys Gly Asp Ser Leu Cys Gln Ser Ser Pro
225                 230                 235                 240

Ser Tyr Asn Val Thr Ala Val His Ser Ile Tyr Leu Pro Ala Asn Phe
                245                 250                 255

Thr Ala Thr Leu His Asp Gln Ala Asn Tyr Ala Gly Lys Lys Ile Val
            260                 265                 270

Tyr Ser Gln Ser Ile Glu Cys Ile Thr Gln Leu Asn Trp Ala Tyr Leu
            275                 280                 285

Leu Ser Thr His Ala Ile Thr Ile Glu Asp Glu Thr Lys Thr Val Leu
290                 295                 300

Arg Arg Asn Asn Arg Arg Asn Glu Asn Leu Tyr Phe Gln Gly Asp Gln
305                 310                 315                 320

Ile Cys Ile Gly Tyr His Ala Asn Asn Ser Thr Glu Gln Val Asp Thr
                325                 330                 335

Ile Met Glu Lys Asn Val Thr Val Thr His Ala Gln Asp Ile Leu Glu
            340                 345                 350

Lys Thr His Asn Gly Lys Leu Cys Asp Leu Asp Gly Val Lys Pro Leu
            355                 360                 365

Ile Leu Arg Asp Cys Ser Val Ala Gly Trp Leu Leu Gly Asn Pro Met

```
                370                 375                 380
Cys Asp Glu Phe Ile Asn Val Pro Trp Ser Tyr Ile Val Glu Lys
385                 390                 395                 400

Ala Asn Pro Val Asn Asp Leu Cys Tyr Pro Gly Asp Phe Asn Asp Tyr
                405                 410                 415

Glu Glu Leu Lys His Leu Leu Ser Arg Ile Asn His Phe Glu Lys Ile
                420                 425                 430

Gln Ile Ile Pro Lys Ser Ser Trp Ser Ser His Glu Ala Ser Leu Gly
                435                 440                 445

Val Ser Ser Ala Cys Pro Tyr Gln Gly Lys Ser Ser Phe Phe Arg Asn
450                 455                 460

Val Val Trp Leu Ile Lys Lys Asn Ser Thr Tyr Pro Thr Ile Lys Arg
465                 470                 475                 480

Ser Tyr Asn Asn Thr Asn Gln Glu Asp Leu Leu Val Leu Trp Gly Ile
                485                 490                 495

His His Pro Asn Asp Ala Ala Glu Gln Thr Lys Leu Tyr Gln Asn Pro
                500                 505                 510

Thr Thr Tyr Ile Ser Val Gly Thr Ser Thr Leu Asn Gln Arg Leu Val
                515                 520                 525

Pro Arg Ile Ala Thr Arg Ser Lys Val Asn Gly Gln Ser Gly Arg Met
530                 535                 540

Glu Phe Phe Trp Thr Ile Leu Lys Pro Asn Asp Ala Ile Asn Phe Glu
545                 550                 555                 560

Ser Asn Gly Asn Phe Ile Ala Pro Glu Tyr Ala Tyr Lys Ile Val Lys
                565                 570                 575

Lys Gly Asp Ser Thr Ile Met Lys Ser Glu Leu Glu Tyr Gly Asn Cys
                580                 585                 590

Asn Thr Lys Cys Gln Thr Pro Met Gly Ala Ile Asn Ser Ser Met Pro
                595                 600                 605

Phe His Asn Ile His Pro Leu Thr Ile Gly Glu Cys Pro Lys Tyr Val
610                 615                 620

Lys Ser Asn Arg Leu Val Leu Ala Thr Gly Leu Arg Asn Ser Pro Gln
625                 630                 635                 640

Arg Glu Arg Arg Arg Lys Lys Arg Gly Leu Phe Gly Ala Ile Ala Gly
                645                 650                 655

Phe Ile Glu Gly Gly Trp Gln Gly Met Val Asp Gly Trp Tyr Gly Tyr
                660                 665                 670

His His Ser Asn Glu Gln Gly Ser Gly Tyr Ala Ala Asp Lys Glu Ser
                675                 680                 685

Thr Gln Lys Ala Ile Asp Gly Val Thr Asn Lys Val Asn Ser Ile Ile
                690                 695                 700

Asp Lys Met Asn Thr Gln Phe Glu Ala Val Gly Arg Glu Phe Asn Asn
705                 710                 715                 720

Leu Glu Arg Arg Ile Glu Asn Leu Asn Lys Lys Met Glu Asp Gly Phe
                725                 730                 735

Leu Asp Val Trp Thr Tyr Asn Ala Glu Leu Leu Val Leu Met Glu Asn
                740                 745                 750

Glu Arg Thr Leu Asp Phe His Asp Ser Asn Val Lys Asn Leu Tyr Asp
                755                 760                 765

Lys Val Arg Leu Gln Leu Arg Asp Asn Ala Lys Glu Leu Gly Asn Gly
                770                 775                 780

Cys Phe Glu Phe Tyr His Lys Cys Asp Asn Glu Cys Met Glu Ser Val
785                 790                 795                 800
```

```
Arg Asn Gly Thr Tyr Asp Tyr Pro Gln Tyr Ser Glu Glu Ala Arg Leu
            805                 810                 815

Lys Arg Glu Glu Ile Ser His His His His His His His His
            820                 825                 830
```

<210> SEQ ID NO 9
<211> LENGTH: 589
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Gly Ser Lys Phe Asn Ile Leu Ile Ile Leu Ile Ile Ser Leu Phe
1               5                   10                  15

Ile Asn Glu Leu Arg Ala Ala Pro Pro Arg Leu Ile Cys Asp Ser Arg
            20                  25                  30

Val Leu Glu Arg Tyr Ile Leu Gly Ala Arg Glu Ala Glu Asn Val Thr
        35                  40                  45

Met Gly Cys Ala Glu Gly Cys Ser Phe Ser Glu Asn Ile Thr Val Pro
    50                  55                  60

Asp Thr Lys Val Asn Phe Tyr Thr Trp Lys Arg Met Asp Val Gly Gln
65                  70                  75                  80

Gln Ala Val Glu Val Trp Gln Gly Leu Ala Leu Leu Ser Glu Ala Ile
                85                  90                  95

Leu Arg Gly Gln Ala Leu Leu Ala Asn Ser Ser Gln Pro Ser Glu Thr
            100                 105                 110

Leu Gln Leu His Val Asp Lys Ala Val Ser Ser Leu Arg Ser Leu Thr
        115                 120                 125

Ser Leu Leu Arg Ala Leu Gly Ala Gln Lys Glu Ala Thr Ser Leu Pro
    130                 135                 140

Glu Ala Thr Ser Ala Ala Pro Leu Arg Thr Phe Thr Val Asp Thr Leu
145                 150                 155                 160

Cys Lys Leu Phe Arg Ile Tyr Ser Asn Phe Leu Arg Gly Lys Leu Thr
                165                 170                 175

Leu Tyr Thr Gly Glu Ala Cys Arg Arg Gly Asp Arg His His His His
            180                 185                 190

His His His His His Glu Asn Leu Tyr Phe Gln Gly Thr Asn Gln
        195                 200                 205

Ser Glu Glu Glu Gly Ser Tyr Thr Ile Asp Gln Ala Ala Asn Leu Leu
    210                 215                 220

Asn Asp Leu Leu Ala Asp Ser Gln Gln Asn Leu Ser Asp Leu Gln Ala
225                 230                 235                 240

Ala Trp Ala Asn Lys Glu Pro Leu Leu Gln Gly Val Ile Ala Gly Leu
                245                 250                 255

Glu Ser Asp Leu Ala Asn Lys Gln Ala Glu Cys Ala Asp Leu Gln Gly
            260                 265                 270

Thr Leu Asp Ala Asp Gln Ala Ser Leu Asp Glu Ala Glu Ala Tyr Val
        275                 280                 285

Ala Trp Leu Gln Asp Arg Ile Ala Ala Asn His Lys Gln Ile Asp Asp
    290                 295                 300

Leu Leu Asn Arg Arg Cys Gln Gln Asn Gly Asn Tyr Ile Glu Gly Leu
305                 310                 315                 320

Lys Asn Asp Lys Leu Ala Leu Ala Leu Leu Gln Phe Leu Glu Ala Gln
                325                 330                 335
```

```
Ile Gln Asn Lys Glu Ser Phe Ser Phe Leu Gln Lys Lys Asn Phe Met
            340                 345                 350

Lys Lys Leu Thr Arg Phe Leu Ser Ile Tyr Lys Thr Gly Asn Tyr Gln
        355                 360                 365

Gln Leu Ala Leu Leu Glu Lys Glu Tyr Val Asn Ala Asp Asp Tyr Ser
    370                 375                 380

Val Asn Pro Asp Tyr Ser Thr Gly Asp Arg Thr Ala Asp Glu Ile Gly
385                 390                 395                 400

Ser Gly His Ile Asp Asn Asp Lys Gly Asp Ile Asp Val Ala Asp Phe
                405                 410                 415

Gln Glu Gly Glu Arg Lys Gly Trp Tyr Gln Val Lys Gln Glu Leu Leu
            420                 425                 430

Asp Leu Leu His Asn Leu Glu Gln Thr Ile Glu Ala Lys Ile Gln Gln
        435                 440                 445

Ala Gln Glu Asp Glu Val Asn Ser Asn Ser Ala Ala Ala Asp Phe Lys
    450                 455                 460

Ser Lys Leu Glu His Glu Ile Gln Val Tyr Glu Arg Glu Leu Ala Lys
465                 470                 475                 480

Trp Gln Gln Thr Val Ala Ala Leu Thr Ala Thr Val Ala Gln Asp His
                485                 490                 495

Glu Asn Val Asn Asn Cys His Ser Gln Glu Ala Ala Ile Gln Ala Asn
            500                 505                 510

Leu Asp Ala Ala Asn Gln Asp Tyr Ala Asn Glu Lys Ala Thr Phe Glu
        515                 520                 525

His Lys Gln Ala Asn Leu Gln Glu Glu Ile Glu Ile Phe Ile Glu Val
    530                 535                 540

Ile Ala Tyr Tyr Asp Asp Asn Val Gln Asn Ala Gly Glu Asp Leu Lys
545                 550                 555                 560

Glu Arg Val Glu Asp Tyr Ser Asp Gly Asn Phe Asp Asp Ala Ala Thr
                565                 570                 575

Tyr Glu Asn Arg Gln Val Pro Asn Ile Asp Phe Ile Asn
            580                 585

<210> SEQ ID NO 10
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ser Asn Lys Leu Leu Val Val Leu Phe Gly Phe Leu Ala Leu
1               5                   10                  15

Ala Ala Ala Thr Asn Gln Ser Glu Glu Gly Ser Tyr Thr Ile Asp
            20                  25                  30

Gln Ala Ala Asn Leu Leu Asn Asp Leu Ala Asp Ser Gln Asn
        35                  40                  45

Leu Ser Asp Leu Gln Ala Ala Trp Ala Asn Lys Glu Pro Leu Leu Gln
50                  55                  60

Gly Val Ile Ala Gly Leu Glu Ser Asp Leu Ala Asn Lys Gln Ala Glu
65                  70                  75                  80

Cys Ala Asp Leu Gln Gly Thr Leu Asp Asp Gln Ala Ser Leu Asp
                85                  90                  95

Glu Ala Glu Ala Tyr Val Ala Trp Leu Gln Asp Arg Ile Ala Ala Asn
            100                 105                 110
```

-continued

His Lys Gln Ile Asp Asp Leu Leu Asn Arg Arg Cys Gln Gln Asn Gly
    115                 120                 125

Asn Tyr Ile Glu Gly Leu Lys Asn Asp Lys Leu Ala Leu Ala Leu Leu
130                 135                 140

Gln Phe Leu Glu Ala Gln Ile Gln Asn Lys Glu Ser Phe Ser Phe Leu
145                 150                 155                 160

Gln Lys Lys Asn Phe Met Lys Lys Leu Thr Arg Phe Leu Ser Ile Tyr
                165                 170                 175

Lys Thr Gly Asn Tyr Gln Gln Leu Ala Leu Leu Glu Lys Glu Tyr Val
            180                 185                 190

Asn Ala Asp Asp Tyr Ser Val Asn Pro Asp Tyr Ser Thr Gly Asp Arg
        195                 200                 205

Thr Ala Asp Glu Ile Gly Ser Gly His Ile Asp Asn Asp Lys Gly Asp
210                 215                 220

Ile Asp Val Ala Asp Phe Gln Glu Gly Glu Arg Lys Gly Trp Tyr Gln
225                 230                 235                 240

Val Lys Gln Glu Leu Leu Asp Leu Leu His Asn Leu Glu Gln Thr Ile
                245                 250                 255

Glu Ala Lys Ile Gln Gln Ala Gln Glu Asp Glu Val Asn Ser Asn Ser
            260                 265                 270

Ala Ala Ala Asp Phe Lys Ser Lys Leu Glu His Glu Ile Gln Val Tyr
        275                 280                 285

Glu Arg Glu Leu Ala Lys Trp Gln Gln Thr Val Ala Ala Leu Thr Ala
290                 295                 300

Thr Val Ala Gln Asp His Glu Asn Val Asn Asn Cys His Ser Gln Glu
305                 310                 315                 320

Ala Ala Ile Gln Ala Asn Leu Asp Ala Ala Asn Gln Asp Tyr Ala Asn
                325                 330                 335

Glu Lys Ala Thr Phe Glu His Lys Gln Ala Asn Leu Gln Glu Glu Ile
            340                 345                 350

Glu Ile Phe Ile Glu Val Ile Ala Tyr Tyr Asp Asp Asn Val Gln Asn
        355                 360                 365

Ala Gly Glu Asp Leu Lys Glu Arg Val Glu Asp Tyr Ser Asp Gly Asn
370                 375                 380

Phe Asp Asp Ala Ala Thr Tyr Glu Asn Arg Gln Val Pro Asn Ile Asp
385                 390                 395                 400

Phe Ile Asn Glu Asn Leu Tyr Phe Gln Gly His His His His His His
                405                 410                 415

Cys Tyr Pro Tyr Asp Val Pro Asp Tyr Ala Ser Leu Asp Ile Gln Met
            420                 425                 430

Thr Gln Ser Pro Ser Ser Leu Ser Ala Ser Val Gly Asp Arg Val Thr
        435                 440                 445

Ile Thr Cys Arg Ala Ser Gln Asp Ile Arg Asn Tyr Leu Asn Trp Tyr
450                 455                 460

Gln Gln Lys Pro Gly Lys Ala Pro Lys Leu Leu Ile Tyr Tyr Thr Ser
465                 470                 475                 480

Arg Leu Leu Pro Gly Val Pro Ser Arg Phe Ser Gly Ser Gly Ser Gly
                485                 490                 495

Thr Asp Tyr Thr Leu Thr Ile Ser Ser Gln Glu Gln Glu Asp Ile Ala
            500                 505                 510

Thr Tyr Tyr Cys Gln Gln Gly Asn Thr Leu Pro Trp Thr Phe Gly Gln
        515                 520                 525

Gly Thr Lys Val Glu Ile Lys Arg Thr Gly Gly Gly Ser Gly Gly
530                 535                 540

```
Gly Gly Ser Gly Gly Gly Ser Gly Gly Gly Ser Glu Val Gln
545                 550                 555                 560

Leu Val Glu Ser Gly Gly Gly Leu Val Gln Pro Gly Ser Leu Arg
        565                 570                 575

Leu Ser Cys Ala Asp Ser Gly Tyr Ala Phe Ser Ser Trp Met Asn
                580                 585                 590

Trp Val Arg Gln Ala Pro Gly Lys Gly Leu Glu Trp Val Gly Arg Ile
        595                 600                 605

Tyr Pro Gly Asp Gly Asp Thr Asn Tyr Asn Gly Lys Phe Lys Gly Arg
610                 615                 620

Ala Thr Ile Ser Ala Asp Lys Ser Ser Ser Thr Ala Tyr Leu Gln Met
625                 630                 635                 640

Asn Ser Leu Arg Ala Glu Asp Thr Ala Val Tyr Tyr Cys Ala Arg Ser
                645                 650                 655

Gly Leu Leu Arg Tyr Ala Met Asp Tyr Trp Gly Gln Gly Thr Leu Val
                660                 665                 670

Thr Val Ser Ser
        675

<210> SEQ ID NO 11
<211> LENGTH: 750
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ser Arg Tyr Ala Ala Leu Phe Leu Leu Ala Leu Ile Ser Phe
1               5                   10                  15

Asn Ala Val Tyr Ala Val Ser Leu Arg Lys Ser Ser Asp Ala Met Lys
            20                  25                  30

Thr Ser Phe Ala Leu Glu Arg Leu Arg Phe Ile Gly Lys Lys Ser Pro
        35                  40                  45

Ile Ala Lys Gln Ile Ile Ser Ala Val Glu Leu His Leu Thr Thr Gly
    50                  55                  60

Gly Leu Val Asp Asp Val Ile Asp Leu Val Lys Gln Ala Gln Glu Asp
65                  70                  75                  80

Val Ala Asn Arg Asn Val Ala Leu Gln Ala Glu Tyr Thr Ala Lys Arg
                85                  90                  95

Gly Ala Leu Glu Asp Gln Ile Asn Thr Thr Thr Gln Gln Leu Asn Glu
            100                 105                 110

Glu Asn Asp Arg Leu Ala Val Val Asn Asp Ala Ile Asp Ala Leu Asn
        115                 120                 125

Gly Gln Ile Asp Ser Leu Asn Thr Gln Ile Ala Asn Leu Val Gln Gln
    130                 135                 140

Leu Gln Asn Leu Gln Ala Arg Glu Asp Ala Ile Asn Gln Ala Arg Glu
145                 150                 155                 160

Val Asp Val Lys Thr Tyr Glu Val Arg Lys Gln Arg Asp Glu Asn Ser
                165                 170                 175

Leu Ala Val Leu Glu Gln Ile Ile Gln Arg Leu Leu Ala Leu Gln Gln
            180                 185                 190

Arg Gly Asn Ala Phe Leu Gln Val Ser Lys Lys Glu Ile Glu Arg Ile
        195                 200                 205

Leu Lys Arg Ile Pro Lys Ser Asn Pro Ile Gln Ala Leu Val Gln Leu
    210                 215                 220
```

-continued

```
Ser Thr Lys Phe Asp Glu Gln Arg Leu Ala Glu Val Ile Ser Lys Leu
225                 230                 235                 240

Gln Thr Ile Gln Ala Ala Ile Gln Ala Ser Tyr Ile Glu Asp Ala Asn
            245                 250                 255

Gly Glu Val Ala Asp Lys Gln Arg Tyr Asp Ala Leu Ile Gln Glu Ile
        260                 265                 270

Ala Thr Ile Arg Ala Gln Thr Gln Gln Leu Ala Asp Ala Gln Gln
    275                 280                 285

Ala Leu Ser Asp Ala Glu Ala Ser Leu Ala Gln Phe Val Gln Glu Gln
    290                 295                 300

Gly Asn Leu Gln Gln Gln Ile Ala Val Asn Glu Gly Ile Leu Ala Asp
305                 310                 315                 320

Ala Gln Ala Ala Leu Ala His Thr Ile Ala Thr Tyr Glu Ala Arg Ile
                325                 330                 335

Gln Glu Gly Gln Glu Ala Leu Ala Ala Ile Asn Leu Ala Leu Asp Val
            340                 345                 350

Leu Gln Gln Asn Gln Ser Asp Leu Gln Gly Val Glu Asp Phe Ser Asn
        355                 360                 365

Ala Tyr Asn Ala Tyr Gln Ala Gly Asn Ser Thr Ala Gly Asp Asp
370                 375                 380

Ala Gly Asp Asp Ser Gly Val Glu Gly Glu Ala Phe Asp Asn Thr Glu
385                 390                 395                 400

Lys Val Ile Ser Ser Ile Glu Gly Arg Ser Ala Met Val His Val Arg
                405                 410                 415

Val Leu Lys Tyr Pro His Asn Ile Leu Phe Thr Asn Leu Thr Asn Asp
            420                 425                 430

Leu Phe Thr Tyr Leu Pro Lys Thr Tyr Asn Glu Ser Asn Phe Val Ser
        435                 440                 445

Asn Val Leu Glu Val Glu Leu Asn Asp Gly Glu Leu Phe Val Leu Ala
    450                 455                 460

Cys Glu Leu Ile Asn Lys Lys Cys Phe Gln Glu Gly Lys Glu Lys Ala
465                 470                 475                 480

Leu Tyr Lys Ser Asn Lys Ile Ile Tyr His Lys Asn Leu Thr Ile Phe
                485                 490                 495

Lys Ala Pro Phe Tyr Val Thr Ser Lys Asp Val Asn Thr Glu Cys Thr
            500                 505                 510

Cys Lys Phe Lys Asn Asn Asn Tyr Lys Ile Val Leu Lys Pro Lys Tyr
        515                 520                 525

Glu Lys Lys Val Ile His Gly Cys Asn Phe Ser Ser Asn Val Ser Ser
    530                 535                 540

Lys His Thr Phe Thr Asp Ser Leu Asp Ile Ser Leu Val Asp Asp Ser
545                 550                 555                 560

Ala His Ile Ser Cys Asn Val His Leu Ser Glu Pro Lys Tyr Asn His
                565                 570                 575

Leu Val Gly Leu Asn Cys Pro Gly Asp Ile Ile Pro Asp Cys Phe Phe
            580                 585                 590

Gln Val Tyr Gln Pro Glu Ser Glu Glu Leu Glu Pro Ser Asn Ile Val
        595                 600                 605

Tyr Leu Asp Ser Gln Ile Asn Ile Gly Asp Ile Glu Tyr Tyr Glu Asp
    610                 615                 620

Ala Glu Gly Asp Asp Lys Ile Lys Leu Phe Gly Ile Val Gly Ser Ile
625                 630                 635                 640

Pro Lys Thr Thr Ser Phe Thr Cys Ile Cys Lys Lys Asp Lys Lys Ser
```

Ala Tyr Met Thr Val Thr Ile Asp His His His His His Cys Pro
            645                 650                 655
Ala Gly Thr Val Val Asp Asp Gly Thr Ser Thr Asn Phe Val Ala Leu
660                 665                 670
Ala Ser Glu Cys Thr Lys Cys Gln Ala Asn Phe Tyr Ala Ser Lys Thr
675                 680                 685
Ser Gly Phe Ala Ala Gly Thr Asp Thr Cys Thr Glu Cys Ser Lys Lys
690                 695                 700
Leu Thr Ser Gly Ala Thr Ala Lys Val Tyr Ala Glu Ala Thr Gln Lys
705                 710                 715                 720
Ala Gln Cys Ala Ser Tyr Pro Tyr Asp Val Pro Asp Tyr Ala
725                 730                 735

740                 745                 750

<210> SEQ ID NO 12
<211> LENGTH: 549
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Ser Asn Lys Lys Leu Leu Val Val Leu Phe Gly Phe Leu Ala
1               5                   10                  15

Leu Ala Ala Ala Thr Asn Gln Ser Glu Glu Glu Gly Ser Tyr Thr Ile
            20                  25                  30

Asp Gln Ala Ala Asn Leu Leu Asn Asp Leu Leu Ala Asp Ser Gln Gln
        35                  40                  45

Asn Leu Ser Asp Leu Gln Ala Ala Trp Ala Asn Lys Glu Pro Leu Leu
    50                  55                  60

Gln Gly Val Ile Ala Gly Leu Glu Ser Asp Leu Ala Asn Lys Gln Ala
65                  70                  75                  80

Glu Cys Ala Asp Leu Gln Gly Thr Leu Asp Ala Asp Gln Ala Ser Leu
                85                  90                  95

Asp Glu Ala Glu Ala Tyr Val Ala Trp Leu Gln Asp Arg Ile Ala Ala
            100                 105                 110

Asn His Lys Gln Ile Asp Asp Leu Leu Asn Arg Arg Cys Gln Gln Asn
        115                 120                 125

Gly Asn Tyr Ile Glu Gly Leu Lys Asn Asp Lys Leu Ala Leu Ala Leu
    130                 135                 140

Leu Gln Phe Leu Glu Ala Gln Ile Gln Asn Lys Glu Ser Phe Ser Phe
145                 150                 155                 160

Leu Gln Lys Lys Asn Phe Met Lys Lys Leu Thr Arg Phe Leu Ser Ile
                165                 170                 175

Tyr Lys Thr Gly Asn Tyr Gln Gln Leu Ala Leu Leu Glu Lys Glu Tyr
            180                 185                 190

Val Asn Ala Asp Asn Thr Glu Lys Val Ile Ser Ser Ile Glu Gly Arg
        195                 200                 205

Ser Ala Met Val His Val Arg Val Leu Lys Tyr Pro His Asn Ile Leu
    210                 215                 220

Phe Thr Asn Leu Thr Asn Asp Leu Phe Thr Tyr Leu Pro Lys Thr Tyr
225                 230                 235                 240

Asn Glu Ser Asn Phe Val Ser Asn Val Leu Glu Val Glu Leu Asn Asp
                245                 250                 255

Gly Glu Leu Phe Val Leu Ala Cys Glu Leu Ile Asn Lys Lys Cys Phe

```
                        260                 265                 270
Gln Glu Gly Lys Glu Lys Ala Leu Tyr Lys Ser Asn Lys Ile Ile Tyr
            275                 280                 285
His Lys Asn Leu Thr Ile Phe Lys Ala Pro Phe Tyr Val Thr Ser Lys
        290                 295                 300
Asp Val Asn Thr Glu Cys Thr Cys Lys Phe Lys Asn Asn Tyr Lys
305                 310                 315                 320
Ile Val Leu Lys Pro Lys Tyr Glu Lys Val Ile His Gly Cys Asn
                325                 330                 335
Phe Ser Ser Asn Val Ser Ser Lys His Thr Phe Thr Asp Ser Leu Asp
            340                 345                 350
Ile Ser Leu Val Asp Asp Ser Ala His Ile Ser Cys Asn Val His Leu
        355                 360                 365
Ser Glu Pro Lys Tyr Asn His Leu Val Gly Leu Asn Cys Pro Gly Asp
        370                 375                 380
Ile Ile Pro Asp Cys Phe Phe Gln Val Tyr Gln Pro Glu Ser Glu Glu
385                 390                 395                 400
Leu Glu Pro Ser Asn Ile Val Tyr Leu Asp Ser Gln Ile Asn Ile Gly
                405                 410                 415
Asp Ile Glu Tyr Tyr Glu Asp Ala Glu Gly Asp Asp Lys Ile Lys Leu
            420                 425                 430
Phe Gly Ile Val Gly Ser Ile Pro Lys Thr Thr Ser Phe Thr Cys Ile
        435                 440                 445
Cys Lys Lys Asp Lys Lys Ser Ala Tyr Met Thr Val Thr Ile Asp His
    450                 455                 460
His His His His Cys Pro Ala Gly Thr Val Val Asp Asp Gly Thr
465                 470                 475                 480
Ser Thr Asn Phe Val Ala Leu Ala Ser Glu Cys Thr Lys Cys Gln Ala
                485                 490                 495
Asn Phe Tyr Ala Ser Lys Thr Ser Gly Phe Ala Ala Gly Thr Asp Thr
            500                 505                 510
Cys Thr Glu Cys Ser Lys Lys Leu Thr Ser Gly Ala Thr Ala Lys Val
        515                 520                 525
Tyr Ala Glu Ala Thr Gln Lys Ala Gln Cys Ala Ser Tyr Pro Tyr Asp
    530                 535                 540
Val Pro Asp Tyr Ala
545

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Tyr Pro Tyr Asp Val Pro Asp Tyr Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Asn Leu Tyr Phe Gln Gly
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 16

His His His His His His His His His His
1               5                   10

<210> SEQ ID NO 17
<211> LENGTH: 906
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Ser Lys Leu Leu Val Val Leu Phe Gly Phe Leu Ala Leu Ala
1               5                   10                  15

Ala Ala Thr Asn Gln Ser Glu Glu Glu Gly Ser Tyr Thr Ile Asp Gln
            20                  25                  30

Ala Ala Asn Leu Leu Asn Asp Leu Leu Ala Asp Ser Gln Gln Asn Leu
        35                  40                  45

Ser Asp Leu Gln Ala Ala Trp Ala Asn Lys Glu Pro Leu Leu Gln Gly
    50                  55                  60

Val Ile Ala Gly Leu Glu Ser Asp Leu Ala Asn Lys Gln Ala Glu Cys
65                  70                  75                  80

Ala Asp Leu Gln Gly Thr Leu Asp Ala Asp Gln Ala Ser Leu Asp Glu
                85                  90                  95

Ala Glu Ala Tyr Val Ala Trp Leu Gln Asp Arg Ile Ala Ala Asn His
            100                 105                 110

Lys Gln Ile Asp Asp Leu Leu Asn Arg Arg Cys Gln Gln Asn Gly Asn
        115                 120                 125

Tyr Ile Glu Gly Leu Lys Asn Asp Lys Leu Ala Leu Ala Leu Leu Gln
    130                 135                 140

Phe Leu Glu Ala Gln Ile Gln Asn Lys Glu Ser Phe Ser Phe Leu Gln
145                 150                 155                 160

Lys Lys Asn Phe Met Lys Lys Leu Thr Arg Phe Leu Ser Ile Tyr Lys
                165                 170                 175

Thr Gly Asn Tyr Gln Gln Leu Ala Leu Leu Glu Lys Glu Tyr Val Asn
            180                 185                 190

Ala Asp Asp Tyr Ser Val Asn Pro Asp Tyr Ser Thr Gly Asp Arg Thr

```
            195                 200                 205
Ala Asp Glu Ile Gly Ser Gly His Ile Asp Asn Asp Lys Gly Asp Ile
210                 215                 220

Asp Val Ala Asp Phe Gln Glu Gly Glu Arg Lys Gly Trp Tyr Gln Val
225                 230                 235                 240

Lys Gln Glu Leu Leu Asp Leu Leu His Asn Leu Glu Gln Thr Ile Glu
                    245                 250                 255

Ala Lys Ile Gln Gln Ala Gln Glu Asp Glu Val Asn Ser Asn Ser Ala
                260                 265                 270

Ala Ala Asp Phe Lys Ser Lys Leu Glu His Glu Ile Gln Val Tyr Glu
            275                 280                 285

Arg Glu Leu Ala Lys Trp Gln Gln Thr Val Ala Ala Leu Thr Ala Thr
        290                 295                 300

Val Ala Gln Asp His Glu Asn Val Asn Asn Cys His Ser Gln Glu Ala
305                 310                 315                 320

Ala Ile Gln Ala Asn Leu Asp Ala Ala Asn Gln Asp Tyr Ala Asn Glu
                325                 330                 335

Lys Ala Thr Phe Glu His Lys Gln Ala Asn Leu Gln Glu Glu Ile Glu
                340                 345                 350

Ile Phe Ile Glu Val Ile Ala Tyr Tyr Asp Asp Asn Val Gln Asn Ala
            355                 360                 365

Gly Glu Asp Leu Lys Glu Arg Val Glu Asp Tyr Ser Asp Gly Asn Phe
        370                 375                 380

Asp Asp Ala Ala Thr Tyr Glu Asn Arg Gln Val Pro Asn Ile Asp Phe
385                 390                 395                 400

Ile Asn Asp Gln Ile Cys Ile Gly Tyr His Ala Asn Asn Ser Thr Glu
                405                 410                 415

Gln Val Asp Thr Ile Met Glu Lys Asn Val Thr Val Thr His Ala Gln
                420                 425                 430

Asp Ile Leu Glu Lys Thr His Asn Gly Lys Leu Cys Asp Leu Asp Gly
            435                 440                 445

Val Lys Pro Leu Ile Leu Arg Asp Cys Ser Val Ala Gly Trp Leu Leu
        450                 455                 460

Gly Asn Pro Met Cys Asp Glu Phe Ile Asn Val Pro Glu Trp Ser Tyr
465                 470                 475                 480

Ile Val Glu Lys Ala Asn Pro Val Asn Asp Leu Cys Tyr Pro Gly Asp
                485                 490                 495

Phe Asn Asp Tyr Glu Glu Leu Lys His Leu Leu Ser Arg Ile Asn His
                500                 505                 510

Phe Glu Lys Ile Gln Ile Ile Pro Lys Ser Ser Trp Ser Ser His Glu
            515                 520                 525

Ala Ser Leu Gly Val Ser Ser Ala Cys Pro Tyr Gln Gly Lys Ser Ser
        530                 535                 540

Phe Phe Arg Asn Val Val Trp Leu Ile Lys Lys Asn Ser Thr Tyr Pro
545                 550                 555                 560

Thr Ile Lys Arg Ser Tyr Asn Asn Thr Asn Gln Glu Asp Leu Leu Val
                565                 570                 575

Leu Trp Gly Ile His His Pro Asn Asp Ala Ala Glu Gln Thr Lys Leu
                580                 585                 590

Tyr Gln Asn Pro Thr Thr Tyr Ile Ser Val Gly Thr Ser Thr Leu Asn
            595                 600                 605

Gln Arg Leu Val Pro Arg Ile Ala Thr Arg Ser Lys Val Asn Gly Gln
        610                 615                 620
```

```
Ser Gly Arg Met Glu Phe Glu Trp Thr Ile Leu Lys Pro Asn Asp Ala
625                 630                 635                 640

Ile Asn Phe Glu Ser Asn Gly Asn Phe Ile Ala Pro Glu Tyr Ala Tyr
            645                 650                 655

Lys Ile Val Lys Lys Gly Asp Ser Thr Ile Met Lys Ser Glu Leu Glu
        660                 665                 670

Tyr Gly Asn Cys Asn Thr Lys Cys Gln Thr Pro Met Gly Ala Ile Asn
    675                 680                 685

Ser Ser Met Pro Phe His Asn Ile His Pro Leu Thr Ile Gly Glu Cys
690                 695                 700

Pro Lys Tyr Val Lys Ser Asn Arg Leu Val Leu Ala Thr Gly Leu Arg
705                 710                 715                 720

Asn Ser Pro Gln Arg Glu Arg Arg Lys Arg Gly Leu Phe Gly
            725                 730                 735

Ala Ile Ala Gly Phe Ile Glu Gly Gly Trp Gln Gly Met Val Asp Gly
            740                 745                 750

Trp Tyr Gly Tyr His His Ser Asn Glu Gln Gly Ser Gly Tyr Ala Ala
        755                 760                 765

Asp Lys Glu Ser Thr Gln Lys Ala Ile Asp Gly Val Thr Asn Lys Val
770                 775                 780

Asn Ser Ile Ile Asp Lys Met Asn Thr Gln Phe Glu Ala Val Gly Arg
785                 790                 795                 800

Glu Phe Asn Asn Leu Glu Arg Arg Ile Glu Asn Leu Asn Lys Lys Met
            805                 810                 815

Glu Asp Gly Phe Leu Asp Val Trp Thr Tyr Asn Ala Glu Leu Leu Val
            820                 825                 830

Leu Met Glu Asn Glu Arg Thr Leu Asp Phe His Asp Ser Asn Val Lys
        835                 840                 845

Asn Leu Tyr Asp Lys Val Arg Leu Gln Leu Arg Asp Asn Ala Lys Glu
850                 855                 860

Leu Gly Asn Gly Cys Phe Glu Phe Tyr His Lys Cys Asp Asn Glu Cys
865                 870                 875                 880

Met Glu Ser Val Arg Asn Gly Thr Tyr Asp Tyr Pro Gln Tyr Ser Glu
            885                 890                 895

Glu Ala Arg Leu Lys Arg Glu Glu Ile Ser
            900                 905

<210> SEQ ID NO 18
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Lys Leu Leu Val Val Leu Phe Gly Phe Leu Ala Leu Ala Ala
1               5                   10                  15

Ala Thr Asn Gln Ser Glu Glu Glu Gly Ser Tyr Thr Ile Asp Gln Ala
            20                  25                  30

Ala Asn Leu Leu Asn Asp Leu Leu Ala Asp Ser Gln Gln Asn Leu Ser
        35                  40                  45

Asp Leu Gln Ala Ala Trp Ala Asn Lys Glu Pro Leu Leu Gln Gly Val
    50                  55                  60

Ile Ala Gly Leu Glu Ser Asp Leu Ala Asn Lys Gln Ala Glu Cys Ala
65                  70                  75                  80
```

-continued

Asp Leu Gln Gly Thr Leu Asp Ala Asp Gln Ala Ser Leu Asp Glu Ala
                85                  90                  95

Glu Ala Tyr Val Ala Trp Leu Gln Asp Arg Ile Ala Ala Asn His Lys
            100                 105                 110

Gln Ile Asp Asp Leu Leu Asn Arg Arg Cys Gln Gln Asn Gly Asn Tyr
        115                 120                 125

Ile Glu Gly Leu Lys Asn Asp Lys Leu Ala Leu Ala Leu Leu Gln Phe
    130                 135                 140

Leu Glu Ala Gln Ile Gln Asn Lys Glu Ser Phe Ser Phe Leu Gln Lys
145                 150                 155                 160

Lys Asn Phe Met Lys Lys Leu Thr Arg Phe Leu Ser Ile Tyr Lys Thr
                165                 170                 175

Gly Asn Tyr Gln Gln Leu Ala Leu Leu Glu Lys Glu Tyr Val Asn Ala
            180                 185                 190

Asp Asp Tyr Ser Val Asn Pro Asp Tyr Ser Thr Gly Asp Arg Thr Ala
        195                 200                 205

Asp Glu Ile Gly Ser Gly His Ile Asp Asn Asp Lys Gly Asp Ile Asp
    210                 215                 220

Val Ala Asp Phe Gln Glu Gly Glu Arg Lys Gly Trp Tyr Gln Val Lys
225                 230                 235                 240

Gln Glu Leu Leu Asp Leu Leu His Asn Leu Glu Gln Thr Ile Glu Ala
                245                 250                 255

Lys Ile Gln Gln Ala Gln Glu Asp Glu Val Asn Ser Asn Ser Ala Ala
            260                 265                 270

Ala Asp Phe Lys Ser Lys Leu Glu His Glu Ile Gln Val Tyr Glu Arg
        275                 280                 285

Glu Leu Ala Lys Trp Gln Gln Thr Val Ala Ala Leu Thr Ala Thr Val
    290                 295                 300

Ala Gln Asp His Glu Asn Val Asn Asn Cys His Ser Gln Glu Ala Ala
305                 310                 315                 320

Ile Gln Ala Asn Leu Asp Ala Ala Asn Gln Asp Tyr Ala Asn Glu Lys
                325                 330                 335

Ala Thr Phe Glu His Lys Gln Ala Asn Leu Gln Glu Glu Ile Glu Ile
            340                 345                 350

Phe Ile Glu Val Ile Ala Tyr Tyr Asp Asp Asn Val Gln Asn Ala Gly
        355                 360                 365

Glu Asp Leu Lys Glu Arg Val Glu Asp Tyr Ser Asp Gly Asn Phe Asp
    370                 375                 380

Asp Ala Ala Thr Tyr Glu Asn Arg Gln Val Pro Asn Ile Asp Phe Ile
385                 390                 395                 400

Asn Gly His His His His His Cys Tyr Pro Tyr Asp Val Pro Asp
                405                 410                 415

Tyr Ala Ser Leu Asp Ile Gln Met Thr Gln Ser Pro Ser Ser Leu Ser
            420                 425                 430

Ala Ser Val Gly Asp Arg Val Thr Ile Thr Cys Arg Ala Ser Gln Asp
        435                 440                 445

Ile Arg Asn Tyr Leu Asn Trp Tyr Gln Gln Lys Pro Gly Lys Ala Pro
    450                 455                 460

Lys Leu Leu Ile Tyr Tyr Thr Ser Arg Leu Leu Pro Gly Val Pro Ser
465                 470                 475                 480

Arg Phe Ser Gly Ser Gly Ser Gly Thr Asp Tyr Thr Leu Thr Ile Ser
                485                 490                 495

Ser Gln Glu Gln Glu Asp Ile Ala Thr Tyr Tyr Cys Gln Gln Gly Asn
            500                 505                 510

```
Thr Leu Pro Trp Thr Phe Gly Gln Gly Thr Lys Val Glu Ile Lys Arg
        515                 520                 525

Thr Gly Gly Gly Ser Gly Gly Gly Ser Gly Gly Gly Gly Ser
530                 535                 540

Gly Gly Gly Gly Ser Glu Val Gln Leu Val Glu Ser Gly Gly Gly Leu
545                 550                 555                 560

Val Gln Pro Gly Gly Ser Leu Arg Leu Ser Cys Ala Asp Ser Gly Tyr
                565                 570                 575

Ala Phe Ser Ser Ser Trp Met Asn Trp Val Arg Gln Ala Pro Gly Lys
            580                 585                 590

Gly Leu Glu Trp Val Gly Arg Ile Tyr Pro Gly Asp Gly Asp Thr Asn
        595                 600                 605

Tyr Asn Gly Lys Phe Lys Gly Arg Ala Thr Ile Ser Ala Asp Lys Ser
        610                 615                 620

Ser Ser Thr Ala Tyr Leu Gln Met Asn Ser Leu Arg Ala Glu Asp Thr
625                 630                 635                 640

Ala Val Tyr Tyr Cys Ala Arg Ser Gly Leu Leu Arg Tyr Ala Met Asp
                645                 650                 655

Tyr Trp Gly Gln Gly Thr Leu Val Thr Val Ser Ser
            660                 665
```